US012564650B2

(12) United States Patent
Fang et al.

(10) Patent No.: US 12,564,650 B2
(45) Date of Patent: Mar. 3, 2026

(54) CARBONIC ANHYDRASE IX-TARGETING RADIOACTIVE DIAGNOSTIC AND THERAPEUTIC MEDICAMENT AND METHOD FOR PREPARING SAME

(71) Applicant: NORROY BIOSCIENCE CO., LTD., Jiangsu (CN)

(72) Inventors: Peng Fang, Jiangsu (CN); Shanyou Yu, Jiangsu (CN); Chenglong Yan, Jiangsu (CN); Wai-si Eng, Jiangsu (CN)

(73) Assignee: NORROY BIOSCIENCE CO., LTD., Jiangsu (CN)

( * ) Notice: Subject to any disclaimer, the term of this patent is extended or adjusted under 35 U.S.C. 154(b) by 0 days.

(21) Appl. No.: 18/805,445

(22) Filed: Aug. 14, 2024

(65) Prior Publication Data

US 2024/0415988 A1 Dec. 19, 2024

Related U.S. Application Data

(63) Continuation of application No. PCT/CN2022/125512, filed on Oct. 14, 2022.

(30) Foreign Application Priority Data

Feb. 15, 2022 (CN) ......................... 202210151238.9

(51) Int. Cl.

| | |
|---|---|
| ***A61K 51/04*** | (2006.01) |
| ***A61K 49/10*** | (2006.01) |
| ***C07D 417/12*** | (2006.01) |
| ***C07D 417/14*** | (2006.01) |

(52) U.S. Cl.

CPC .............. *A61K 51/04* (2013.01); *A61K 49/10* (2013.01); *C07D 417/12* (2013.01); *C07D 417/14* (2013.01)

(58) Field of Classification Search

CPC ...... A61K 51/04; A61K 49/10; C07D 417/12; C07D 417/14

USPC ........................................................ 424/1.65

See application file for complete search history.

(56) References Cited

U.S. PATENT DOCUMENTS

| | | | |
|---|---|---|---|
| 2012/0321563 A1* | 12/2012 | Groves ................ | C07D 209/14 544/298 |
| 2021/0154334 A1 | 5/2021 | Guan et al. | |

FOREIGN PATENT DOCUMENTS

| | | |
|---|---|---|
| CN | 109476655 A | 3/2019 |
| WO | WO2015114171 A1 | 8/2015 |
| WO | WO2016196628 A1 | 12/2016 |
| WO | WO2018154517 A1 | 8/2018 |

OTHER PUBLICATIONS

Krall et al. J. Nucl Med 2016, 57, 9430949. (Year: 2016).*
Baumhover et al. Bioorg. Med. Chem. Lett. 21 (2011) 5757-5761. (Year: 2011).*
Chen et al. Molecules 2019, 24, 1-13. (Year: 2019).*
Cazzamalli, et al., "Acetazolamide Serves as Selective Delivery Vehicle for Dipeptide-Linked Drugs to Renal Cell Carcinoma," Molecular Cancer Therapeutics, vol. 15, No. 12, Dec. 2016, pp. 2926-2935.
Chen, et al., "A Flexible Synthesis of 68Ga-Labeled Carbonic Anhydrase IX (CAIX)-Targeted Molecules via CBT/1,2-Aminothiol Click Reaction," Molecules, vol. 24, No. 1, Dec. 2018, 13 pages.
Search Report and Written Opinion in International Application No. PCT/CN2022/125512, Dated Dec. 20, 2022, 23 pages.
Krall, et al., "A Technetium 99m-Labeled Ligand of Carbonic Anhydrase IX Selectively Targets Renal Cell Carcinoma In Vivo," Journal of Nuclear Medicine, vol. 57, No. 6, Feb. 2016, pp. 943-949.
Pellegrino, et al., "Impact of Ligand Size and Conjugation Chemistry on the Performance of Universal Chimeric Antigen Receptor T-Cells for Tumor Killing," Bioconjugate Chemistry, vol. 31, No. 7, Jun. 2020, pp. 1775-1783.
Wichert, et al., "Dual-Display of Small Molecules Enables the Discovery of Ligand Pairs and Facilitates Affinity Maturation," Nature Chemistry, vol. 7, No. 3, Jan. 2015, pp. 241-249.

* cited by examiner

*Primary Examiner* — Michael G. Hartley
*Assistant Examiner* — Sean R Donohue
(74) *Attorney, Agent, or Firm* — Lee & Hayes, P.C.

(57) ABSTRACT

The present application relates to a carbonic anhydrase IX-targeting radioactive diagnostic and therapeutic medicament and a preparation method thereof. Specifically, the present disclosure relates to a compound, or a pharmaceutically acceptable salt, ester, or solvate thereof. The compound has a structure represented by Formula (I). The compound can be used for diagnosing and/or treating one or more tumors, cancers, or cells expressing carbonic anhydrase IX.

(I)

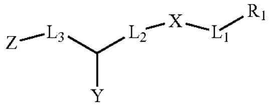

7 Claims, 18 Drawing Sheets

CARBONIC ANHYDRASE IX-TARGETING RADIOACTIVE DIAGNOSTIC AND THERAPEUTIC MEDICAMENT AND METHOD FOR PREPARING SAME

CROSS-REFERENCE TO RELATED APPLICATIONS

This application is a continuation of International Application No. PCT/CN2022/125512, filed on Oct. 14, 2022, which claims the priority and benefit of patent application No. 202210151238.9 filed with the China National Intellectual Property Administration on Feb. 15, 2022. The disclosures of the aforementioned applications are hereby incorporated by reference in their entireties.

FIELD

The present disclosure relates to the field of medicine. Particularly, the present disclosure relates to a carbonic anhydrase (CA) IX-targeting radioactive diagnostic and therapeutic medicament and a preparation method thereof. More particularly, the present disclosure relates to a compound represented by Formula (I) or Formula (II), or a pharmaceutically acceptable salt, ester, solvate, complex, or pharmaceutical composition thereof as well as use thereof.

BACKGROUND

Renal cell carcinoma (RCC) is the most common renal neoplasm. Among cases of RCC, a clear cell renal cell carcinoma subtype (ccRCC) is the most prevalent, accounting for up to 70% of RCC cases, ccRCC commonly loses Von Hippel-Lindau (VHL) tumor suppressor gene. The loss of VHL subsequently leads to the overexpression of carbonic anhydrase IX (CAIX) (Bragmaier et al., 2004). CAIX is a membrane-associated enzyme responsible for catalyzing a reversible hydrosynthesis of carbon dioxide into bicarbonate anions and protons. The overexpression of CAIX has been verified in approximately 95% of ccRCC tumor samples, and accordingly, it has been confirmed as a useful biomarker for ccRCC.

CAIX has limited expression in normal tissues and organs other than gastrointestinal tract, gall bladder, and pancreatic duct. There are no reports demonstrating the expression of CAIX in normal renal parenchyma or benign renal masse. The feasibility of non-invasive diagnosis of ccRCC based on the expression of CAIX has been verified with a radiolabeled antibody G250. However, antibodies, as molecular imaging agents, are subject to limitations in terms of pharmacokinetics, including their slow blood and non-target tissue clearance (usually 2 to 5 days or even longer) and uptake of nonspecific organ. Low molecular weight (LMW) agents demonstrate faster pharmacokinetics and higher specific signals within a clinically convenient time after administration. They also provide site-specific radiolabeling that is typically performed through a broader range of radiochemical methods and radioactive nuclides, and can provide a shorter path to regulatory approval.

Therefore, more targeted radioactive diagnostic and therapeutic medicaments targeting CAIX are being currently developed and put into use.

SUMMARY

In a first aspect, the present disclosure provides a compound, or a pharmaceutically acceptable salt, ester, or solvate thereof. The compound has a structure represented by Formula (I),

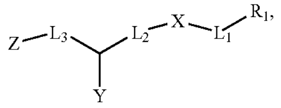

(I)

wherein:

X is an optionally substituted 5 to 6 membered heterocyclic group, cycloalkyl, diazolyl, triazolyl, or acylamino;

Y is

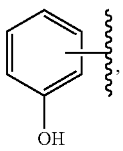

,

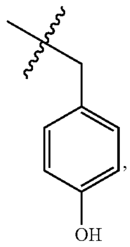

, optionally substituted

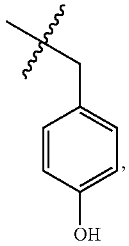

,

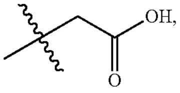

—COOH,

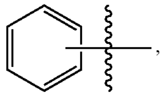

optionally substituted

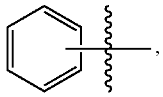

—OH, —$CH(CH_3)OH$, a water-soluble amino acid, a chelating group, or a fluorescent group;

Z is H, a chelating group, or a fluorescent group;

at least one of Y and Z is a chelating group or a fluorescent group;

$L_1$, $L_2$, and $L_3$ are each selected from a polyethylene glycol chain, hydrophilic amino acid chain, carbon chain, or —$(CH_2)$nCONH—;

$R_1$ is selected from a 5 to 12 membered heteroaryl group substituted with sulfonic acid amino, and n is an integer between 1 and 6.

In a second aspect, the present disclosure further provides a compound, or a pharmaceutically acceptable salt, ester, or solvate thereof. The compound has a structure represented by Formula (II), (II)

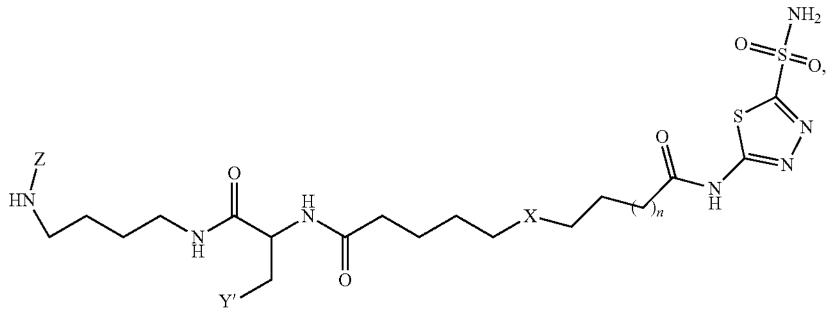

wherein:

n is 1 or 2;

X is a 5 to 6 membered heterocyclic group, cycloalkyl, diazolyl, triazolyl, or acylamino;

Y' is

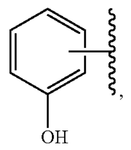

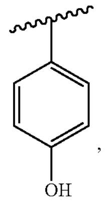

optionally substituted

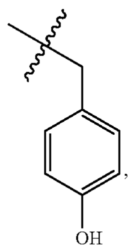

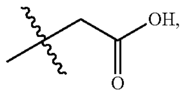

—COOH,

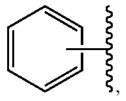

optionally substituted

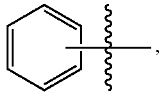

—OH, —$CH(CH_3)OH$, a water-soluble amino acid, a chelating group, or a fluorescent group;

Z is H, a chelating group, or a fluorescent group; and at least one of Y' and Z is a chelating group or a fluorescent group.

In a third aspect, the present disclosure further provides a compound, or a pharmaceutically acceptable salt, ester, or solvate thereof. The compound has a structure selected from any one of the following:

(1)

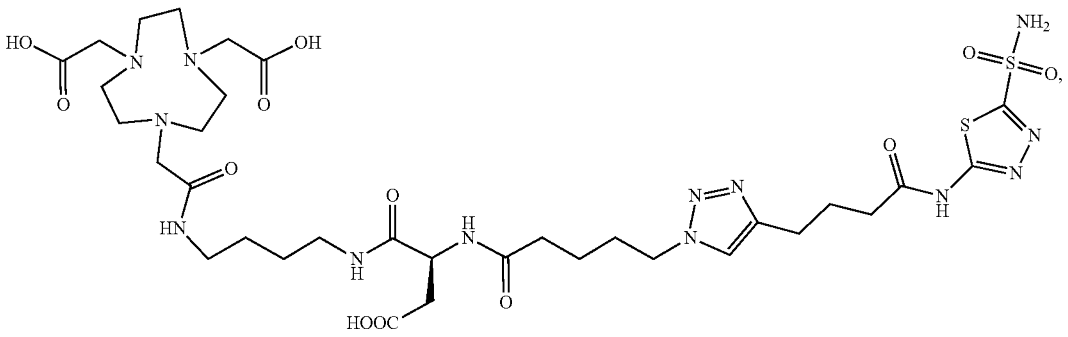

-continued
(2)
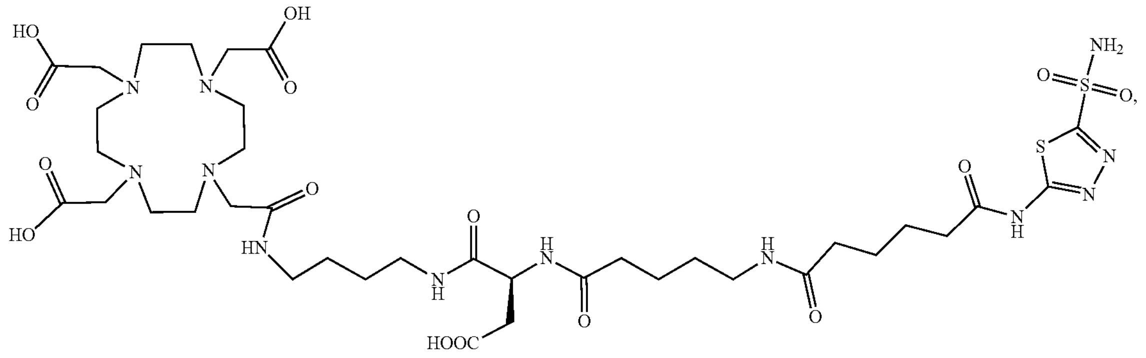
(3)
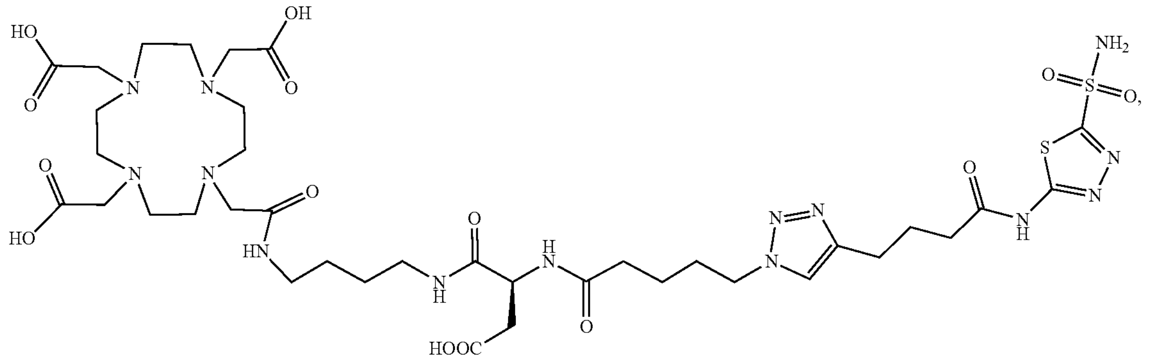
(4)
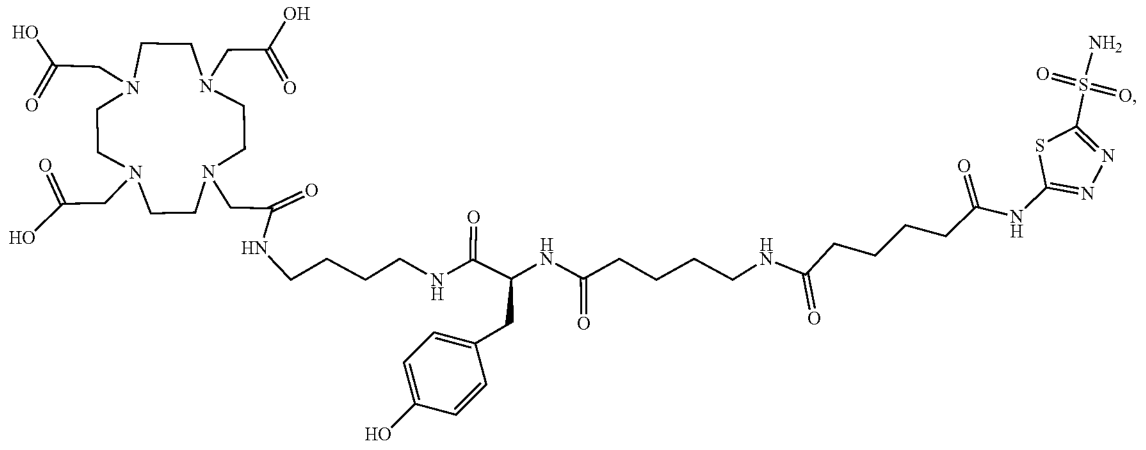
(5)
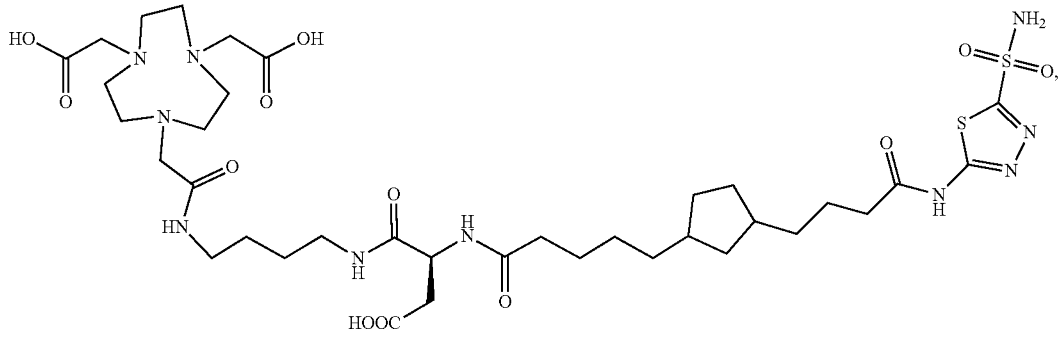

-continued
(6)
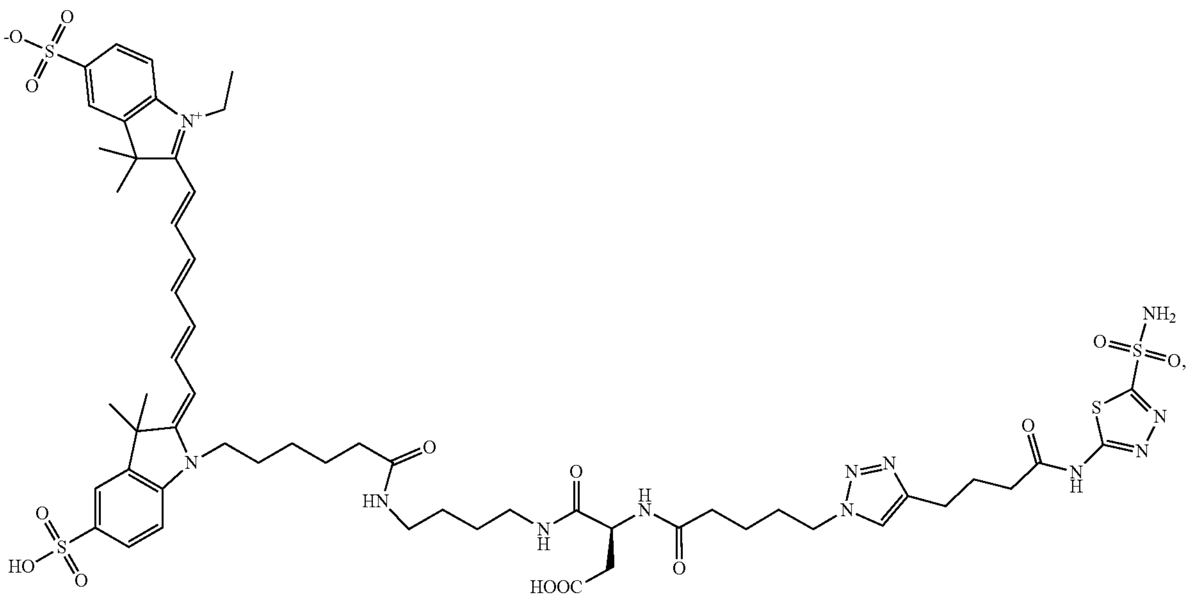
(7)
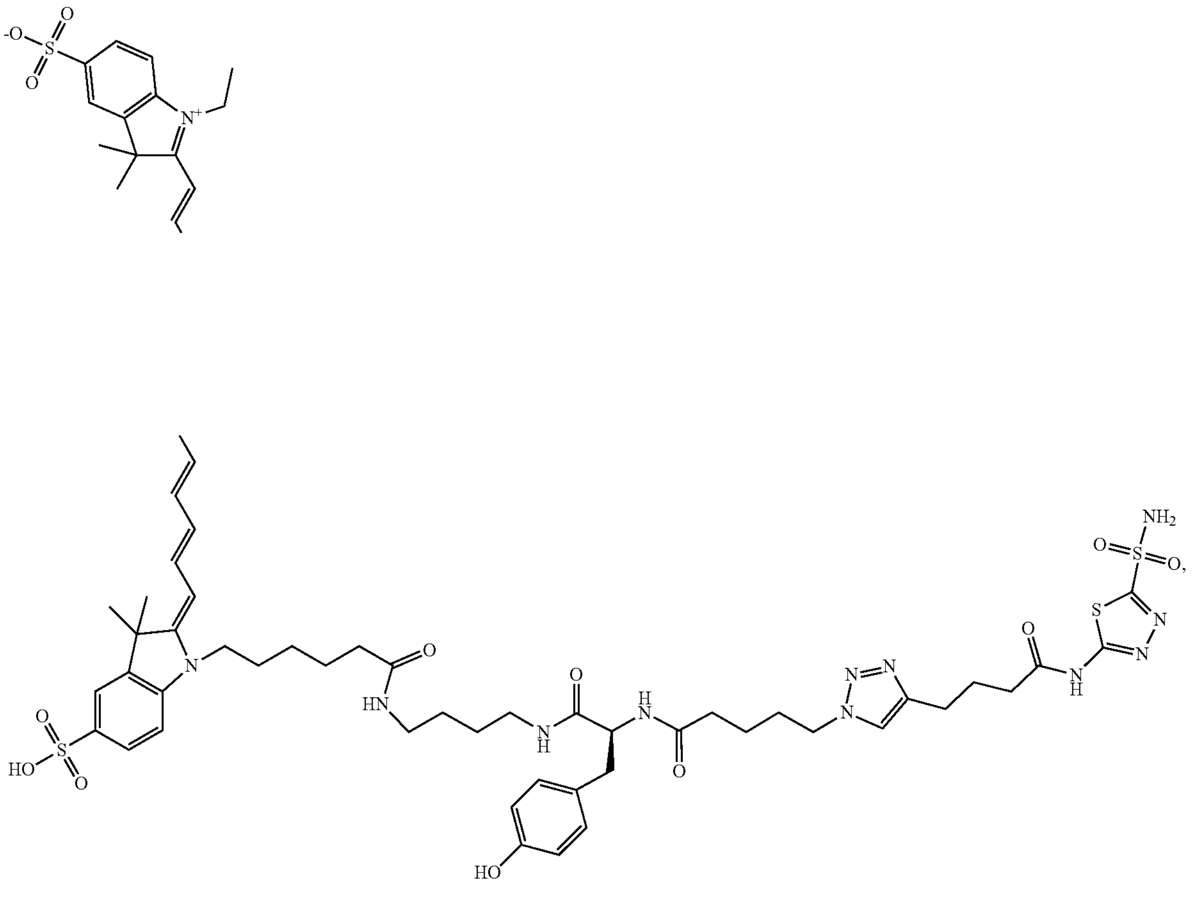

-continued
(8)
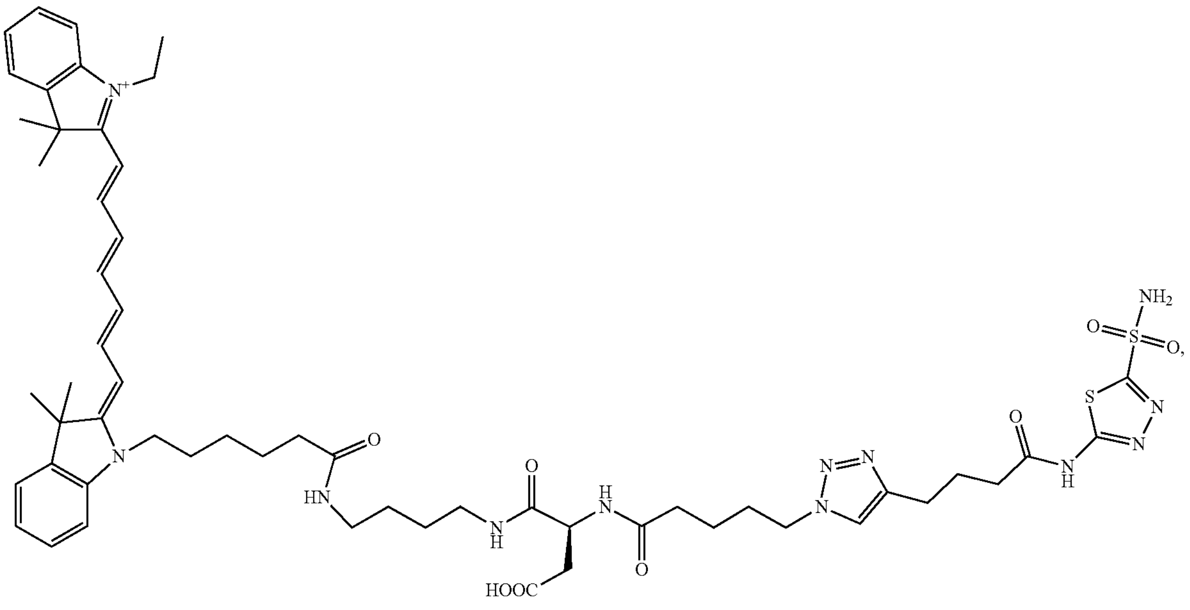
(9)
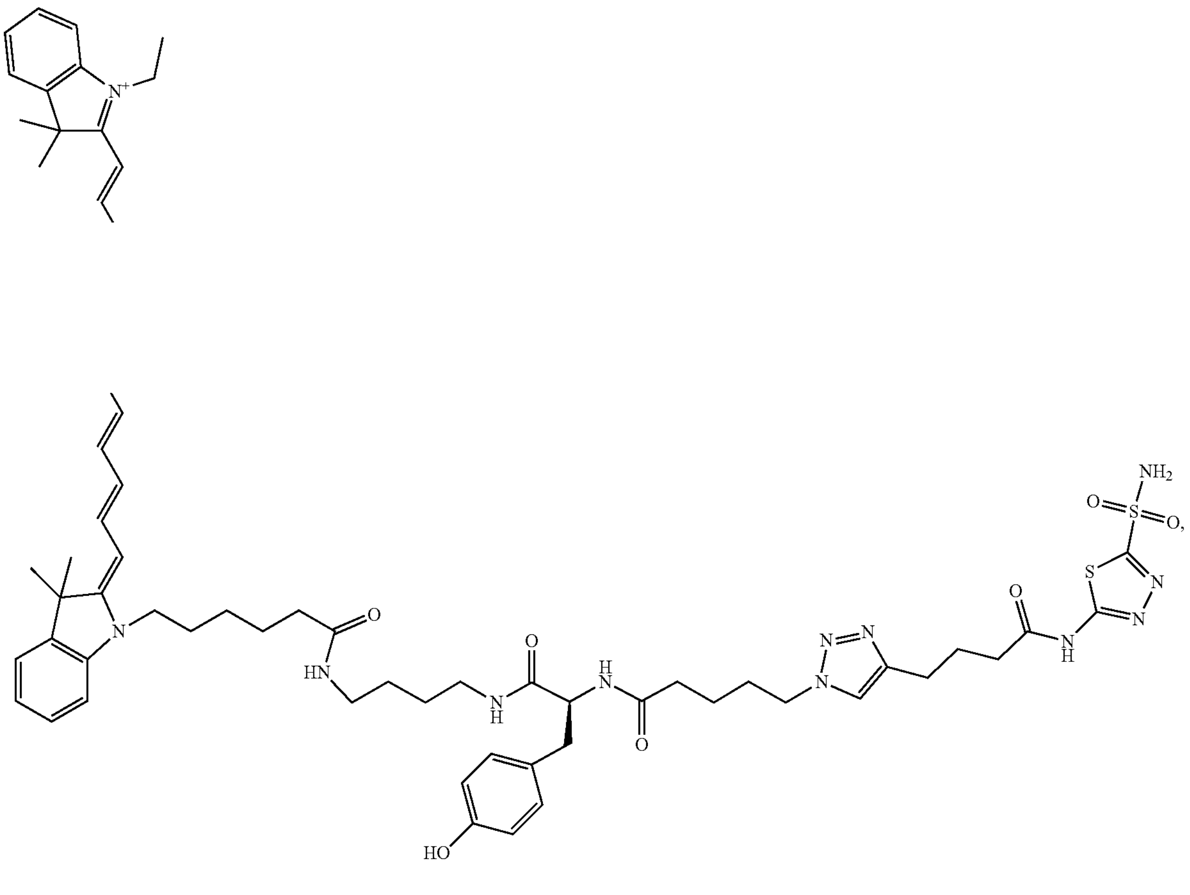

-continued
(10)
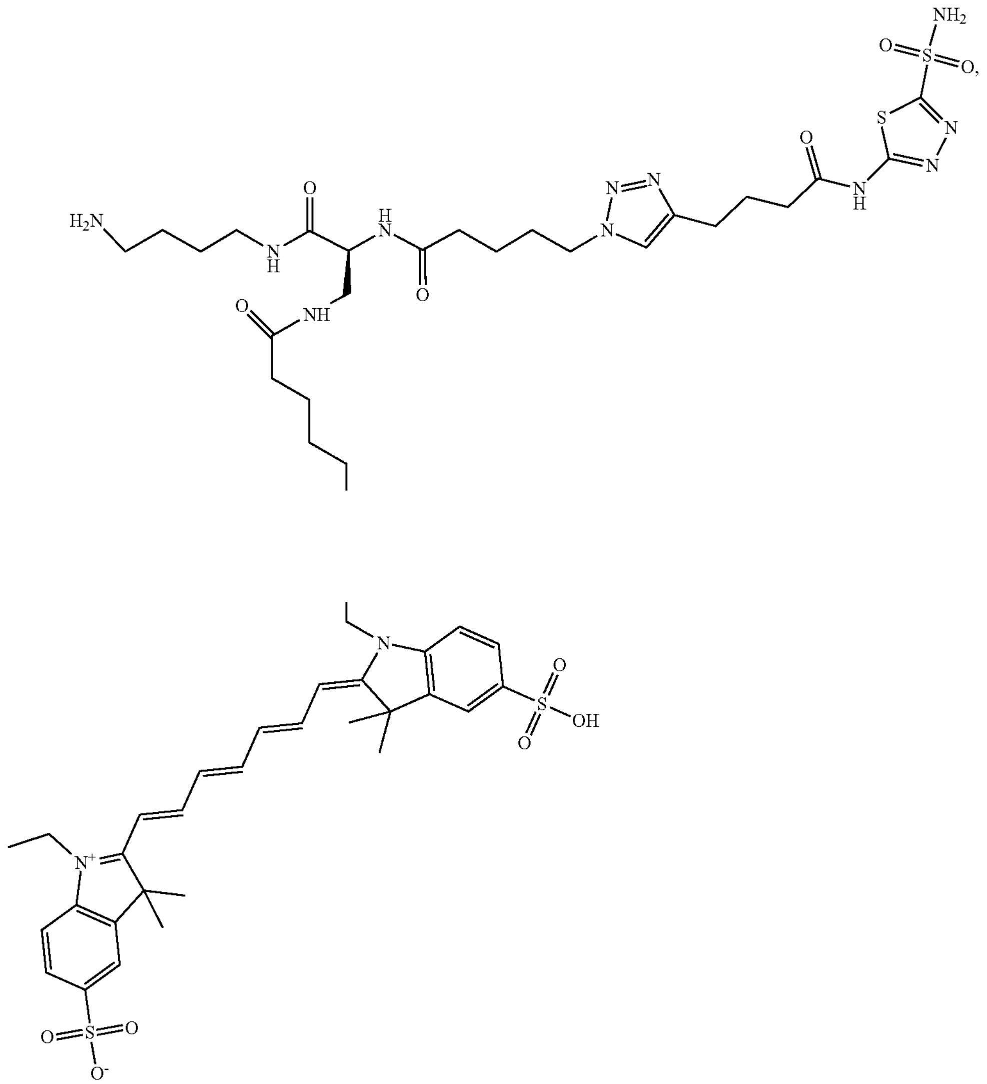
and
(11)
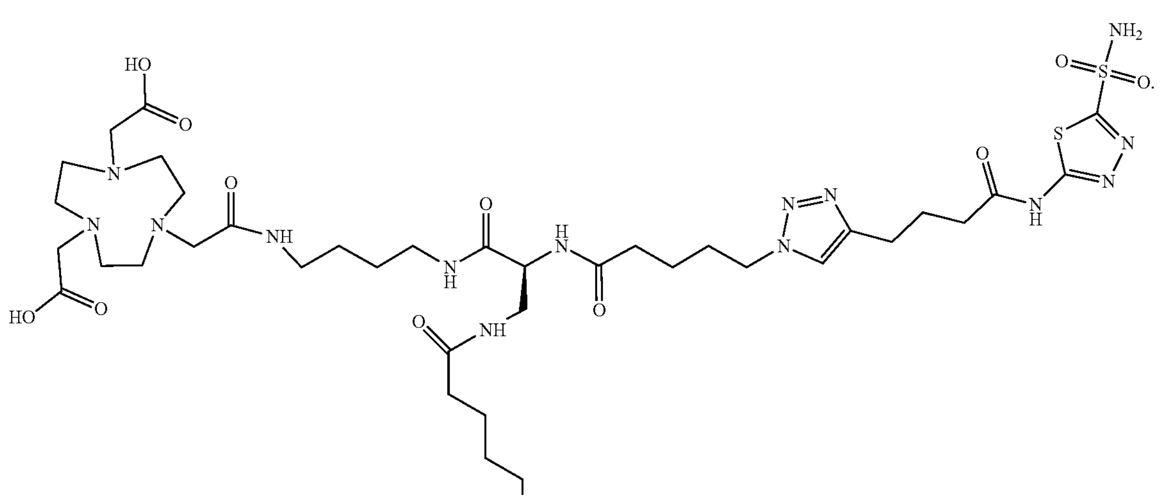

-continued

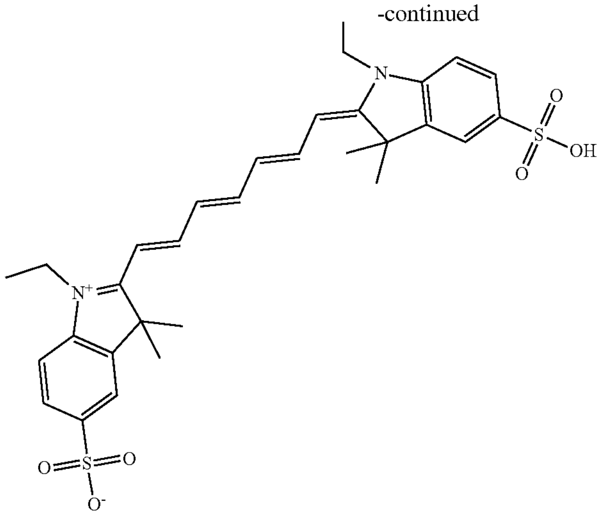

In a fourth aspect, the present disclosure further provides a compound. The compound is formed by binding the above-mentioned compound, or the pharmaceutically acceptable salt, ester, or solvate thereof to a radioactive nuclide or a non-radioactive element.

In a fifth aspect, the present disclosure further provides a pharmaceutical composition. The pharmaceutical composition includes: the above-mentioned compound, or the pharmaceutically acceptable salt, ester, or solvate thereof; and a pharmaceutically acceptable carrier, excipient, and the like.

In a sixth aspect, the present disclosure further provides a method for diagnosing and/or treating tumors, cancers, or cells expressing carbonic anhydrase IX. The method includes administering a pharmaceutically acceptable dose of the above-mentioned compound, pharmaceutically acceptable salt, ester, or solvate thereof, or the above-mentioned pharmaceutical composition to a patient.

In a seventh aspect, the present disclosure further provides a kit. The kit includes the above-mentioned compound, pharmaceutically acceptable salt, ester, or solvate thereof, or the above-mentioned pharmaceutical composition.

BRIEF DESCRIPTION OF THE DRAWINGS

The foregoing and/or additional aspects and advantages of the present disclosure will become apparent and more readily appreciated from the following descriptions made with reference to the accompanying drawings, in which.

DETAILED DESCRIPTION

Figure 1:
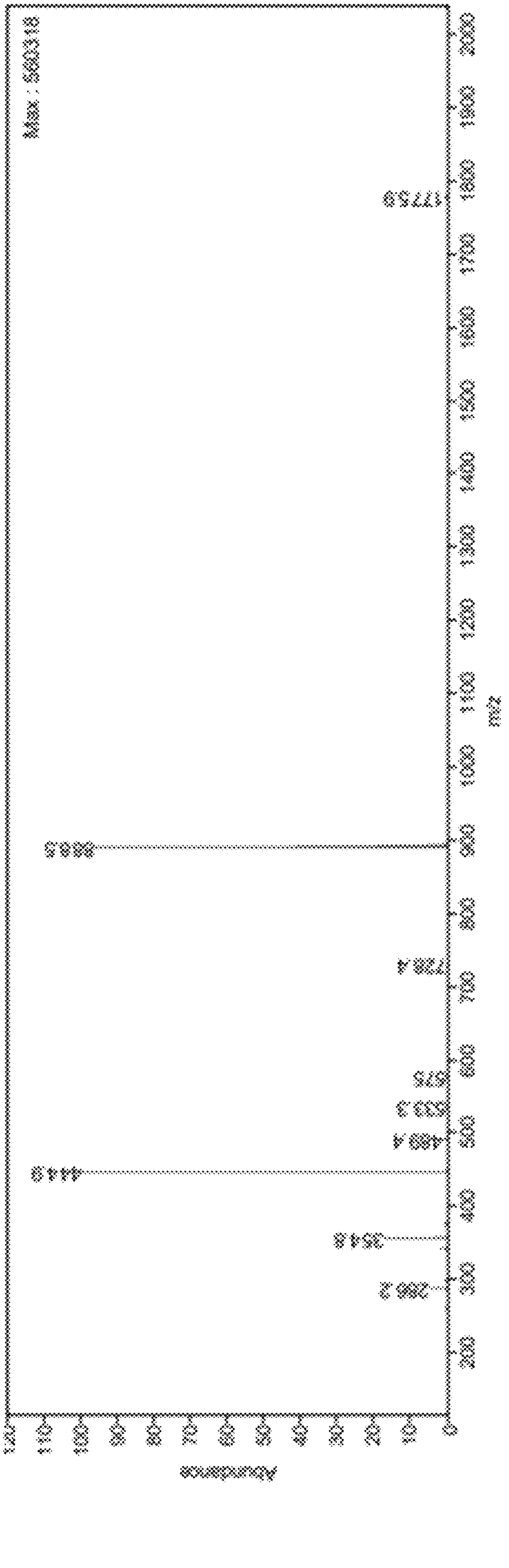
FIG. 1 is a Liquid Chromatograph Mass Spectrometer (LC-MS) spectrum of NYM005 molecule according to an embodiment of the present disclosure.

The present disclosure is described below with reference to specific embodiments. It should be noted that these embodiments are merely illustrative and do not limit the present disclosure in any way.

In a first aspect, the present disclosure provides a compound, or a pharmaceutically acceptable salt, ester, or solvate thereof. The compound has a structure represented by Formula (I), (I)

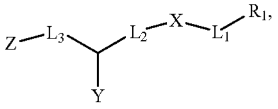

wherein:

X is an optionally substituted 5 to 6 membered heterocyclic group, cycloalkyl, diazolyl, triazolyl, or acylamino;

Y is

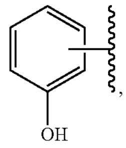,

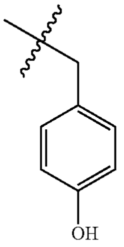, optionally substituted

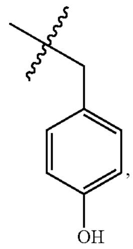,

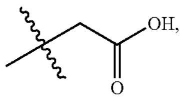

—COOH,

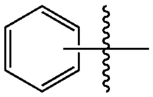, optionally substituted

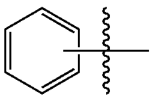,

—OH, —CH($CH_3$)OH, a water-soluble amino acid, a chelating optionally substituted group, or a fluorescent group;

Z is H, a chelating group, or a fluorescent group;

at least one of Y and Z is a chelating group or a fluorescent group;

$L_1$, $L_2$, and $L_3$ are each selected from polyethylene glycol chain, hydrophilic amino acid chain, carbon chain, or —($CH_2$)nCONH—;

$R_1$ is selected from a 5 to 12 membered heteroaryl group substituted with sulfonic acid amino, and n is an integer between 1 and 6.

The present disclosure provides a compound, or a pharmaceutically acceptable salt, ester, or solvate thereof. The compound has a structure represented by Formula (I), (I)

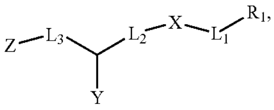

wherein:

X is selected from a 5 to 6 membered heterocyclic group, diazolyl, triazolyl, and acylamino;

Y is selected from

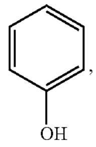,

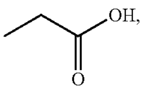

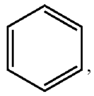,

—OH, —CH($CH_3$)OH, a water-soluble amino acid, a chelating group, and a fluorescent group;

Z is selected from H, a chelating group, and a fluorescent group;

$L_1$, $L_2$, and $L_3$ are each selected from a polyethylene glycol chain, hydrophilic amino acid chain, and carbon chain; and $R_1$ is selected from a 5 to 12 membered heteroaryl group substituted with sulfonic acid amino.

In some embodiments of the present disclosure, the above-mentioned polyethylene glycol chain is a chain formed by one or more polyethylene glycol units (—O—$(CH_2)_2$—O—), such as a chain formed by 1, 2, 3, 4, 5, 6, 7, or 8 polyethylene glycol units (—O—$(CH_2)_2$—O—), and the remaining variables are as defined in the present disclosure.

In some embodiments of the present disclosure, the above-mentioned hydrophilic amino acid chain is a chain formed by condensation of one or more identical or different

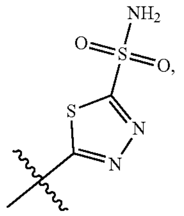

and the remaining variables are as defined in the present disclosure.

In another aspect, the present disclosure further provides a compound, or a pharmaceutically acceptable salt, ester, or solvate thereof. The compound has a structure represented by Formula (II), (II)

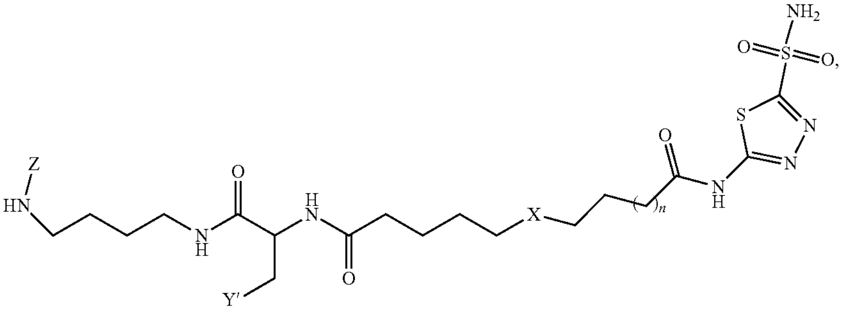

hydrophilic amino acids, such as a chain formed by condensation of 1, 2, 3, 4, 5, 6, 7, or 8 hydrophilic amino acids. The hydrophilic amino acid is a generic term for amino acids with high hydrophilicity in the side chain. For example, the hydrophilic amino acids include threonine (Thr), serine (Ser), cysteine (Cys), asparagine (Asn), glutamine (Gln), tyrosine (Tyr), lysine (Lys), arginine (Arg), histidine (His), aspartic acid (Asp), or glutamic acid (Glu), and the remaining variables are as defined in the present disclosure.

In some embodiments of the present disclosure, the above-mentioned carbon chain refers to a carbon chain formed by one or more substituted or unsubstituted straight-chain alkyl groups or branched-chain alkyl groups, such as a carbon chain formed by a substituted or unsubstituted straight-chain alkyl group or branched-chain alkyl group consisting of 1, 2, 3, 4, 5, 6, 7, or 8 carbon atoms, and the remaining variables are as defined in the present disclosure.

In some embodiments of the present disclosure, the above-mentioned $R_1$ is selected from

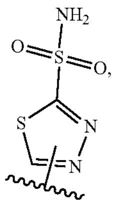

such as wherein:

n is 1 or 2;

X is a 5 to 6 membered heterocyclic group, cycloalkyl, diazolyl, triazolyl, or acylamino;

Y' is

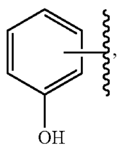

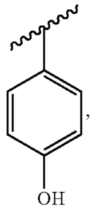

optionally substituted

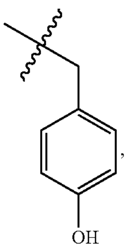

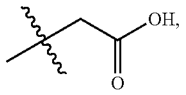

—COOH,

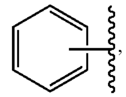

optionally substituted

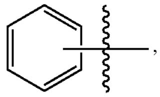

—OH, —$CH(CH_3)OH$, a water-soluble amino acid, a chelating group, or a fluorescent group;

Z is H, a chelating group, or a fluorescent group; and at least one of Y' and Z is a chelating group or a fluorescent group.

In another aspect, the present disclosure further provides a compound, or a pharmaceutically acceptable salt, ester, or solvate thereof. The compound has a structure represented by Formula (II), -continued

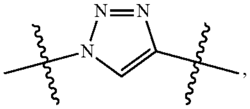

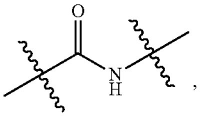

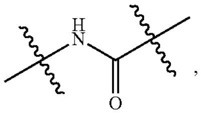

, or

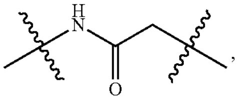

and the remaining variables are as defined in the present disclosure.

In some embodiments of the present disclosure, the above-mentioned X is selected from

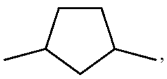

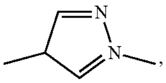

(II)

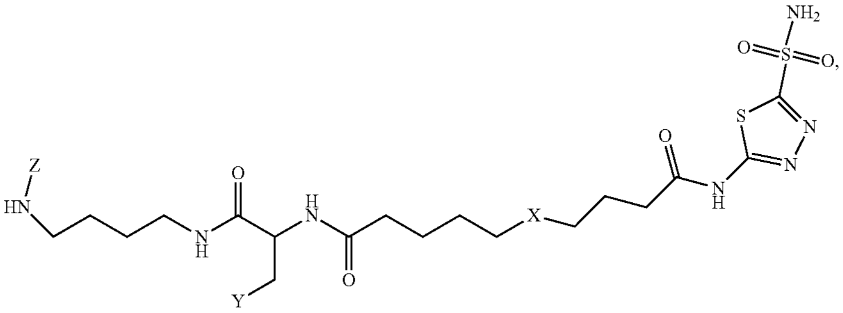

wherein:

X is selected from an optionally substituted 5 to 6 membered heterocyclic group, diazolyl, triazolyl, and acylamino;

Y is selected from

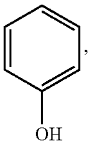

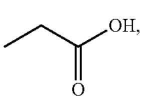

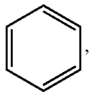

—OH, —$CH(CH_3)OH$, water-soluble amino acid, a chelating group, and a fluorescent group; and Z is selected from H, a chelating group, or a fluorescent group.

In some embodiments of the present disclosure, the above-mentioned X is selected from

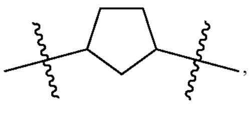

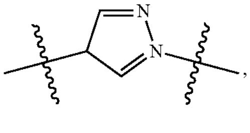

-continued

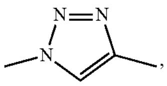

and

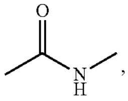

and the remaining variables are as defined in the present disclosure.

In some embodiments of the present disclosure, the above-mentioned chelating group is selected from 1,4,7,10-tetraazacyclododecane-N,N',N",N"",-tetraacetic acid, 1,4,7-triazacyclononane-1,4,7-triacetic acid, 2-(4,7-bis (carboxymethyl)-1,4,7-triazonon-1-yl) pentanedioic acid, 2-(4,7,10-tris (carboxymethyl)-1,4,7,10-tetraazacyclododecan-1-yl) pentanedioic acid, 1,4,7-triazacyclononane phosphinic acid, 1,4,7-triazacyclononane-1-[methyl (2-carboxyethyl) phosphinic acid]-4,7-bis [methyl (2-carboxymethyl) phosphinic acid], N'-{5-[acetyl (hydroxy) amino]pentyl}-N-[5-({4-[5-amino pentyl) (hydroxy) amino]-4-oxobutanoyl}amino) pentyl]-N-hydroxysuccinamide, diethylenetriaminepentaacetic acid, trans-cyclohexyl-diethylenetriaminepentaacetic acid, p-isothiocyanatobenzyl-diethylenetriaminepentaacetic acid, 1-(isothiocyanatobenzyl)-3-methyl-diethylenetriaminepentaacetic acid, 1-(isothiocyanatobenzyl)-4-methyl-diethylenetriaminepentaacetic acid, 1-(2)-methyl-4-isocyanatobenzyl-diethylenetriaminepentaacetic acid, 1-oxa-4,7,10-triazacyclododecane-4,7,10-triacetic acid, succinimidyl 6-hydraziniu- mnicotinate hydrochloride, and mercaptoacetyl triglycine, and the remaining variables are as defined in the present disclosure.

In some embodiments of the present disclosure, the above-mentioned fluorescent group is selected from anthocyanin fluorescent dye, including non-sulfonated anthocyanin dye and sulfonated anthocyanin dye, and the remaining variables are as defined in the present disclosure.

In some embodiments of the present disclosure, the anthocyanin fluorescent dye is selected from Cy3, Cy3.5, Cy5, Cy5.5, Cy7, Cy7.5, sulfonated-Cy3, sulfonated-Cy5, or sulfonated-Cy7, or ICG, etc., and the remaining variables are as defined in the present disclosure.

In some embodiments of the present disclosure, the above-mentioned fluorescent group is selected from

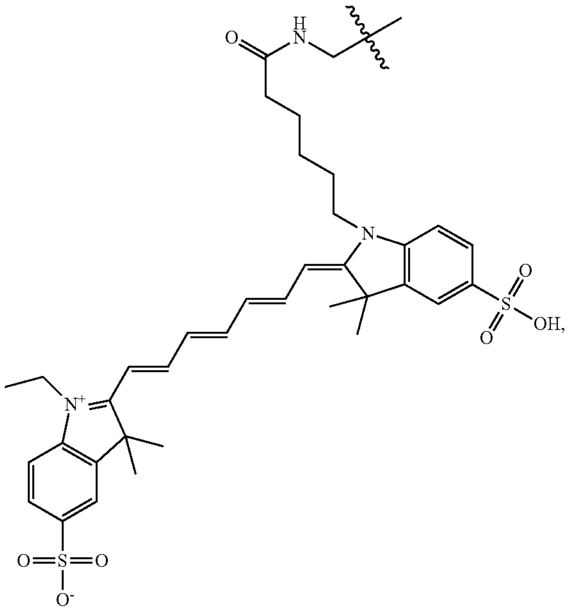

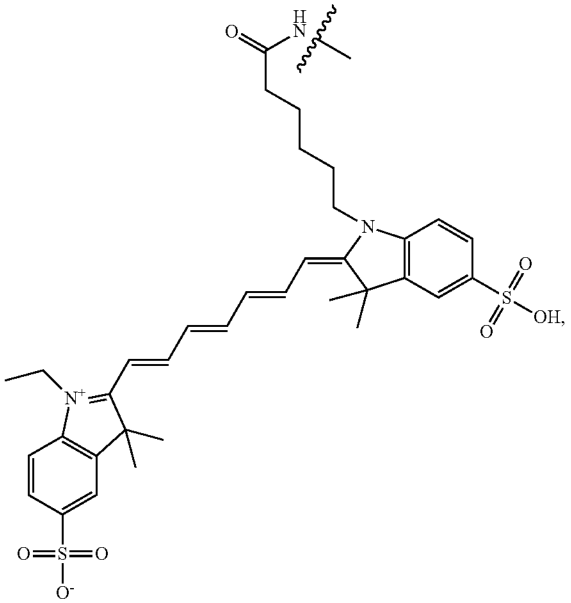

-continued

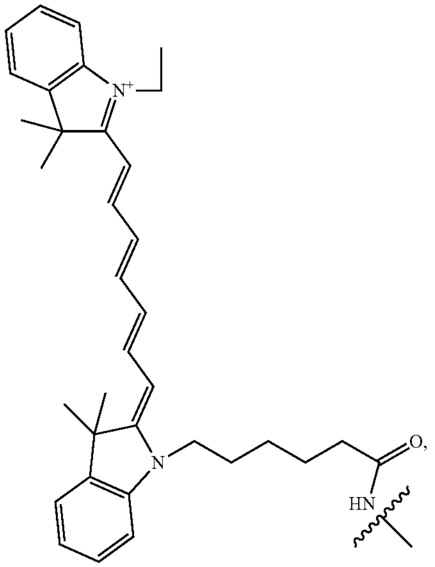

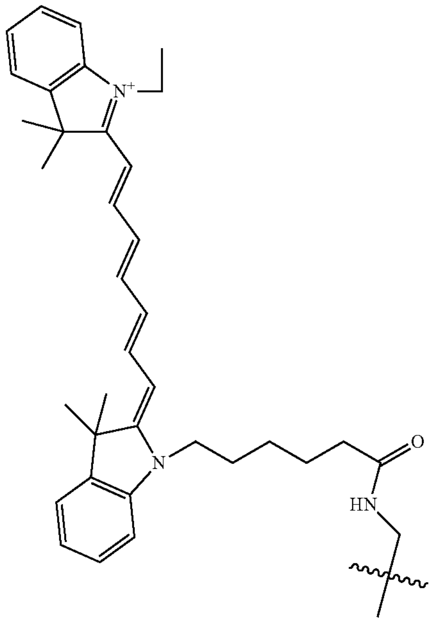

,

-continued
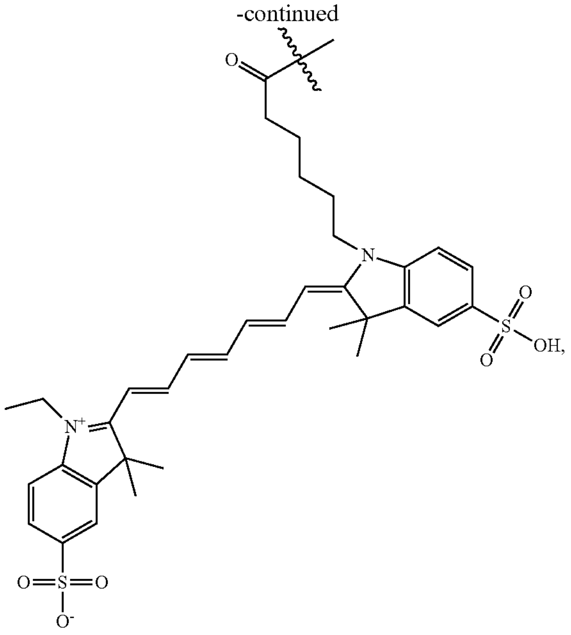
or
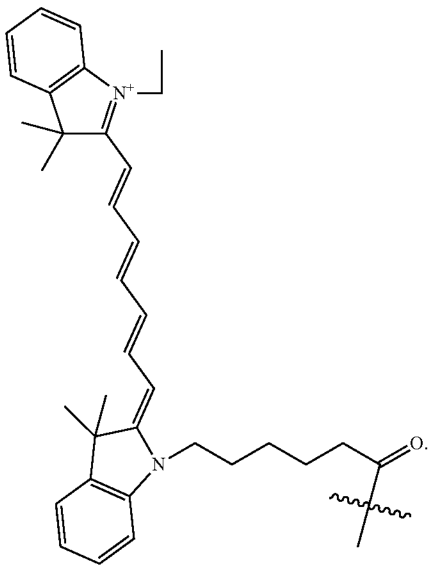
In another aspect, the present disclosure further provides a compound, or a pharmaceutically acceptable salt, ester, or solvate thereof. The compound has a structure selected from any one of the following:
(1)
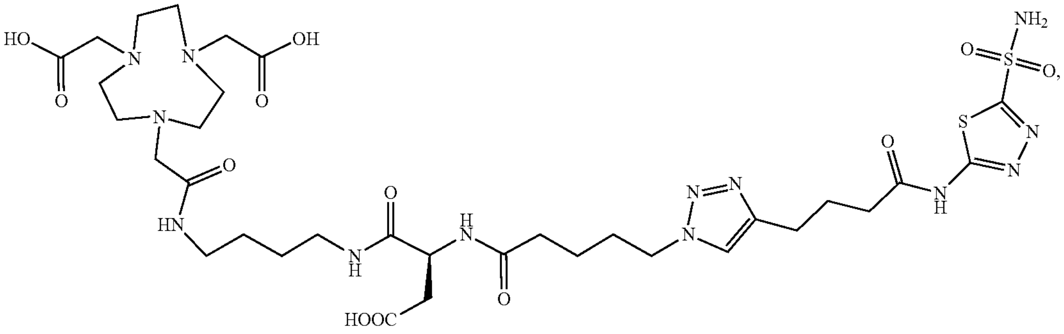

-continued
(2)
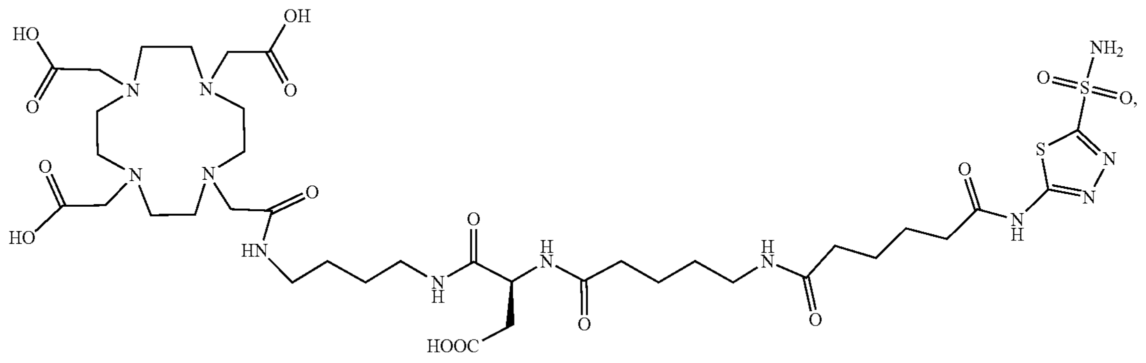
(3)
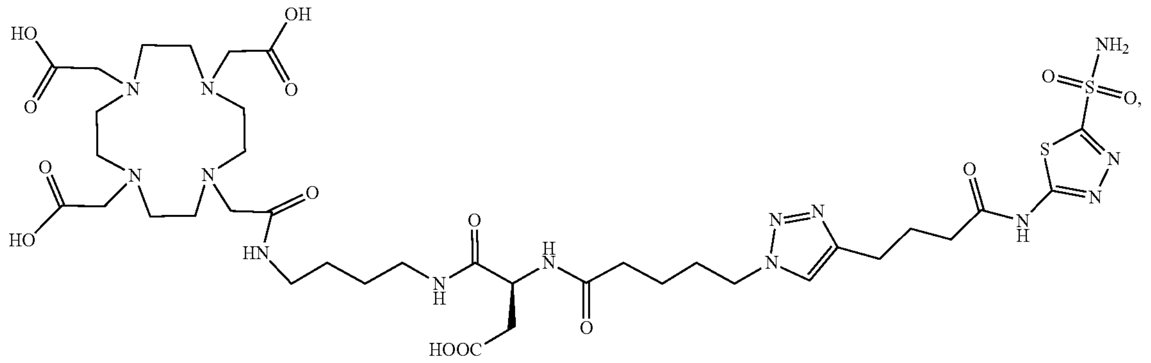
(4)
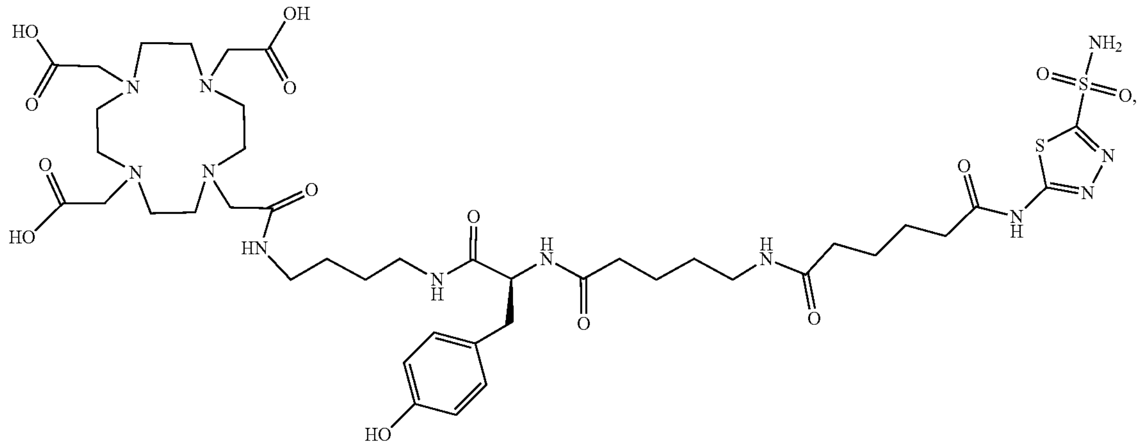
(5)
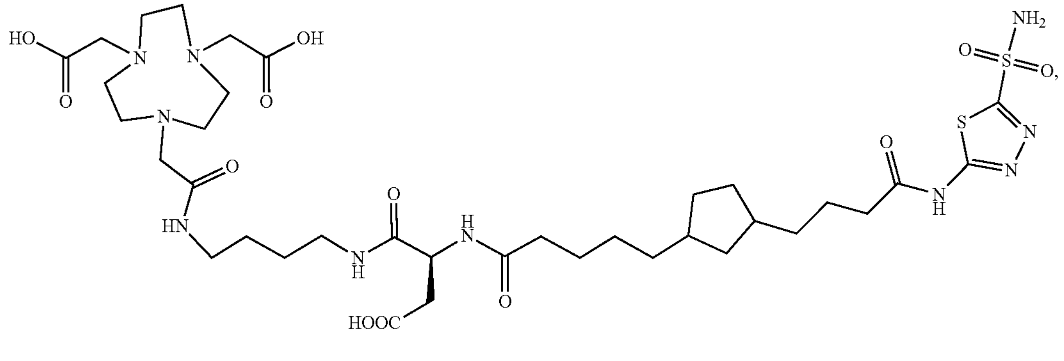

-continued
(6)
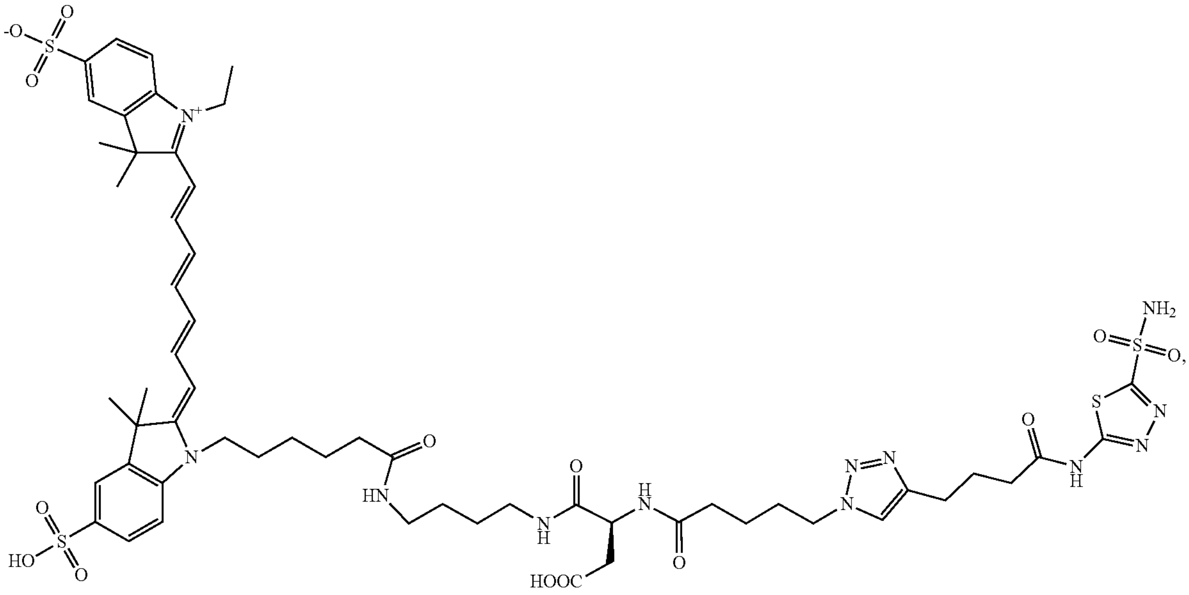
(7)
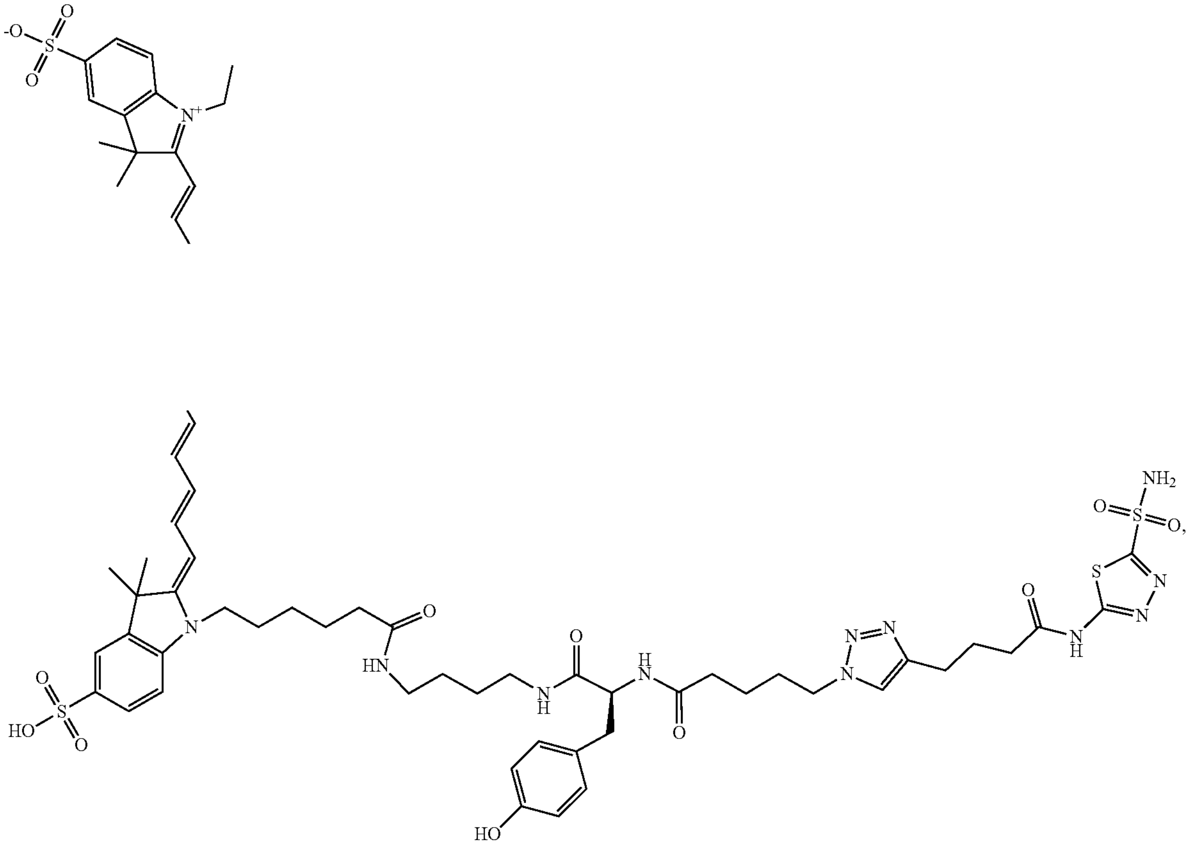

-continued
(8)
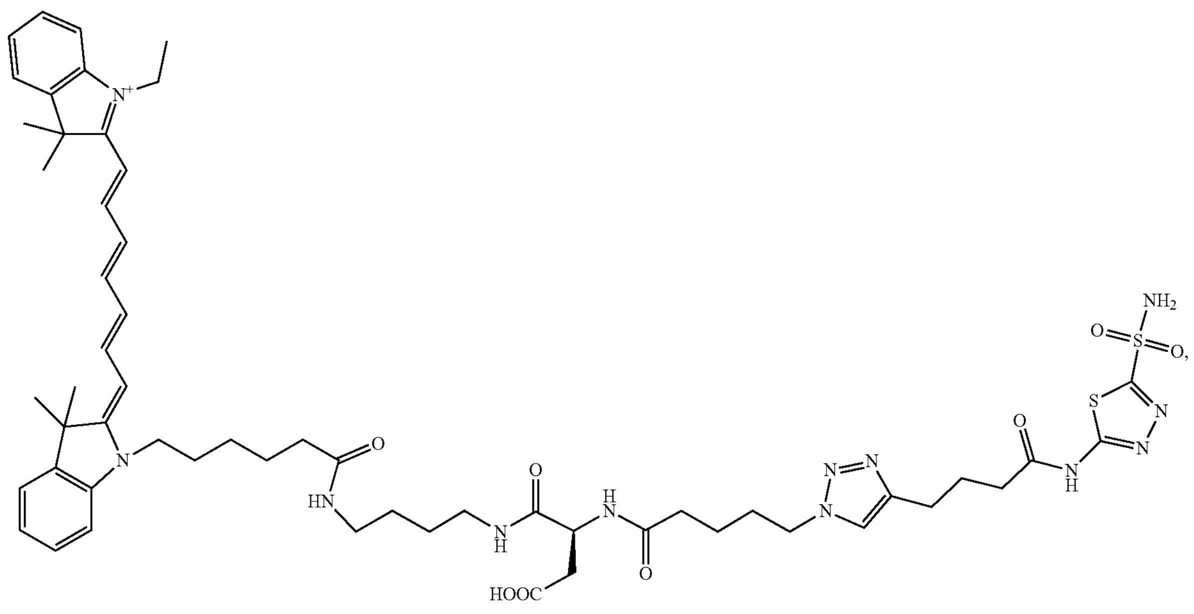
(9)
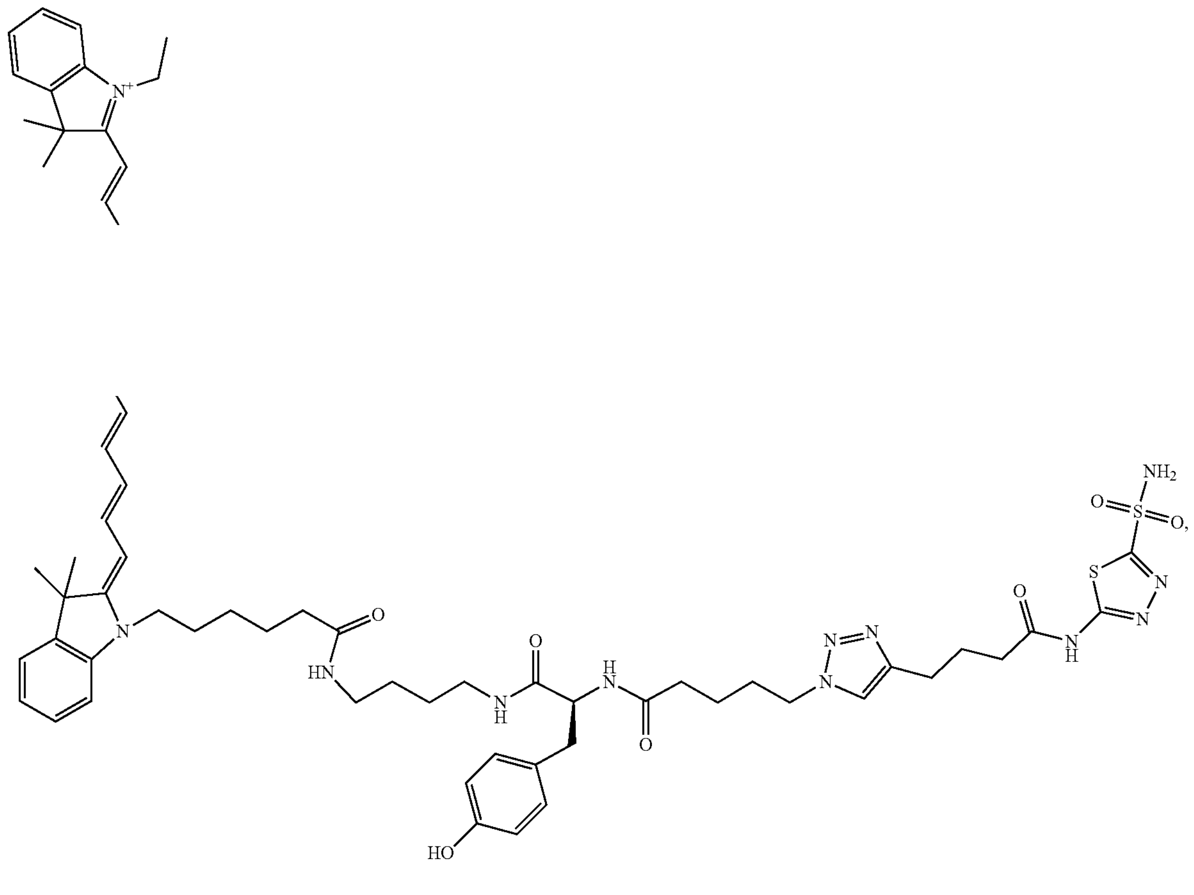

-continued
(10)
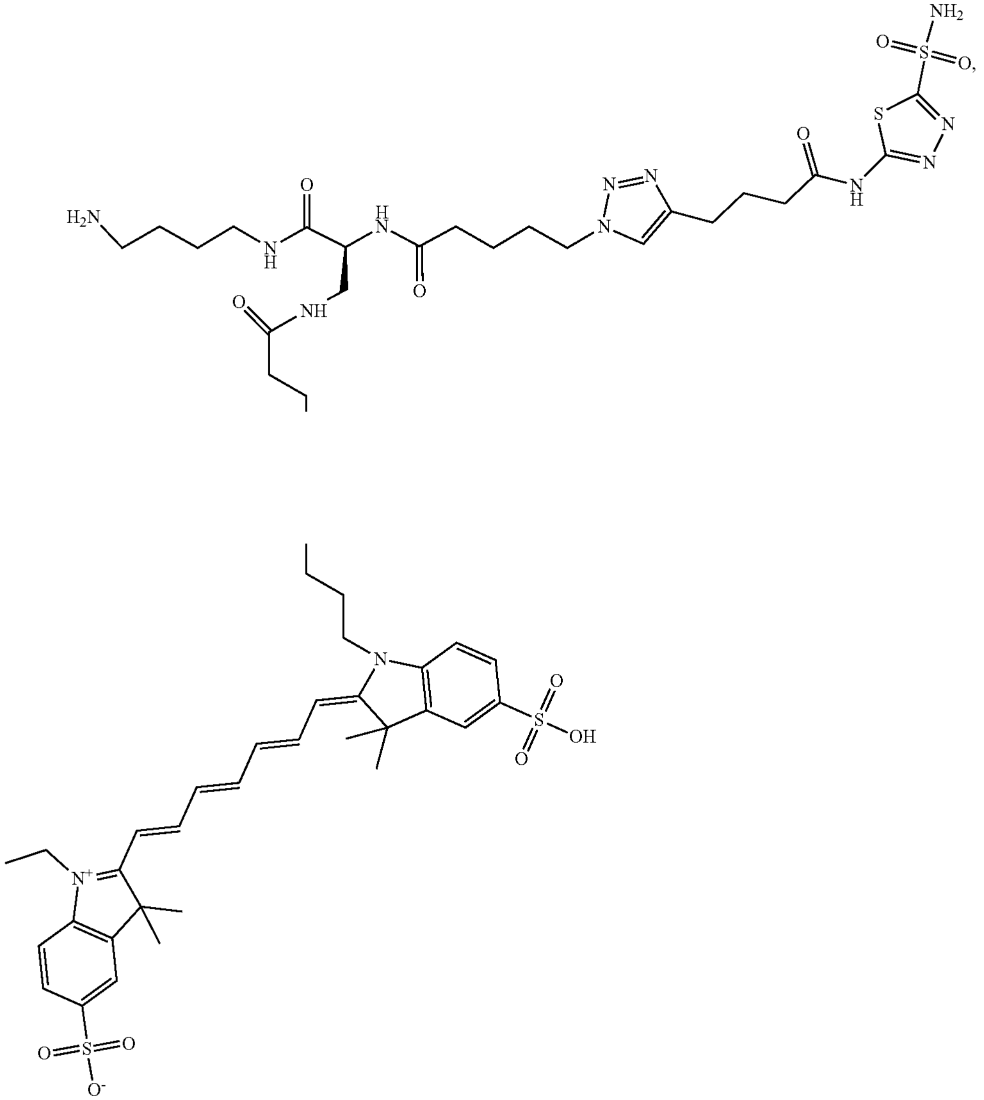
and
(11)
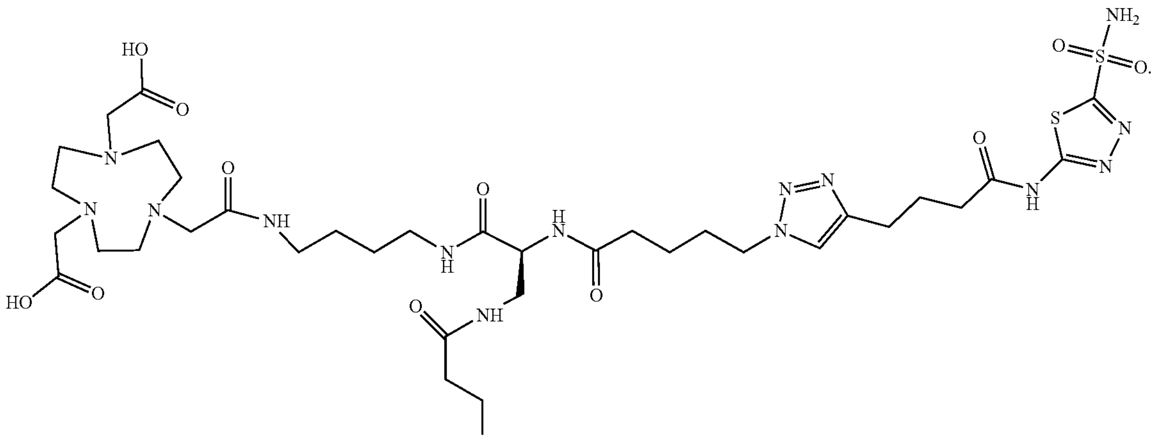

-continued

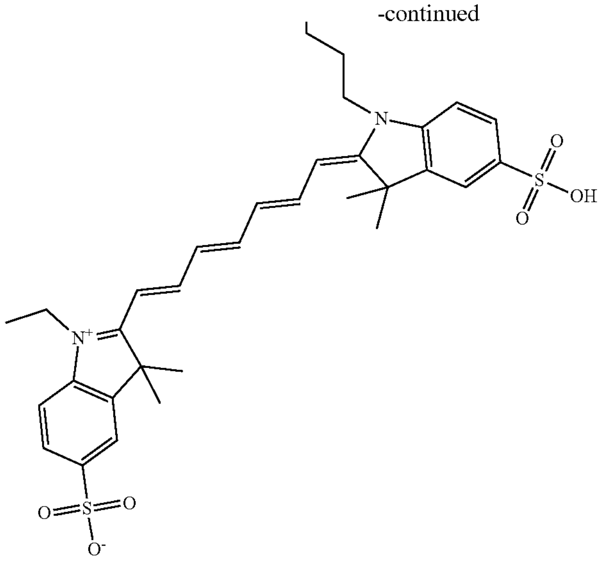

In yet another aspect, the present disclosure further provides a compound. According to an embodiment of the present disclosure, the compound is formed by binding the above-mentioned compound, or the pharmaceutically acceptable salt, ester, or solvate thereof to a radioactive nuclide or a non-radioactive element.

In some embodiments of the present disclosure, the radioactive nuclide is selected from $^{68}$Ga, $^{18}$F, $^{99m}$Tc, $^{89}$Zr, $^{111}$In, $^{45}$Ti, $^{59}$Fe, $^{64}$Cu, $^{94m}$Tc, $^{67}$Ga, $^{71/72/74}$ As, $^{43/44}$ Sc, $^{82m}$Rb, $^{52}$Mn, $^{86}$Y, $^{125}$I, $^{124}$I, $^{76}$Br, $^{177}$Lu, $^{90}$Y, $^{131}$I, $^{153}$Sm, $^{67}$Cu, $^{89}$Sr, $^{137}$Cs, $^{166}$Ho, $^{177}$Yb, $^{105}$Rh, $^{186/188}$Re, $^{47}$Sc, $^{212/213}$Bi, $^{225}$ Ac, $^{212}$Pb, $^{149}$Pm, $^{211}$ At, $^{223}$Ra, and $^{227}$Th.

In some embodiments of the present disclosure, the radioactive nuclide is selected from $^{131}$I. According to an embodiment of the present disclosure, a labeling site of $^{131}$I is on a phenolic hydroxyl of tyrosine, and $^{131}$I is labeled simultaneously with other nuclides (such as $^{68}$Ga), enabling simultaneous diagnosis function and treatment function to be achieved on one molecule.

In some embodiments of the present disclosure, the non-radioactive element is selected from Ga, Fe, and Gd.

In some embodiments of the present disclosure, the radioactive nuclide is selected from $^{18}$F.

In some embodiments of the present disclosure, the radioactive nuclide $^{18}$F is bound to the above-mentioned compound, or the pharmaceutically acceptable salt, ester, or solvate thereof via aluminum.

In yet another aspect, the present disclosure further provides a compound. According to an embodiment of the present disclosure, the compound has a structure selected from one of the following:

(12)

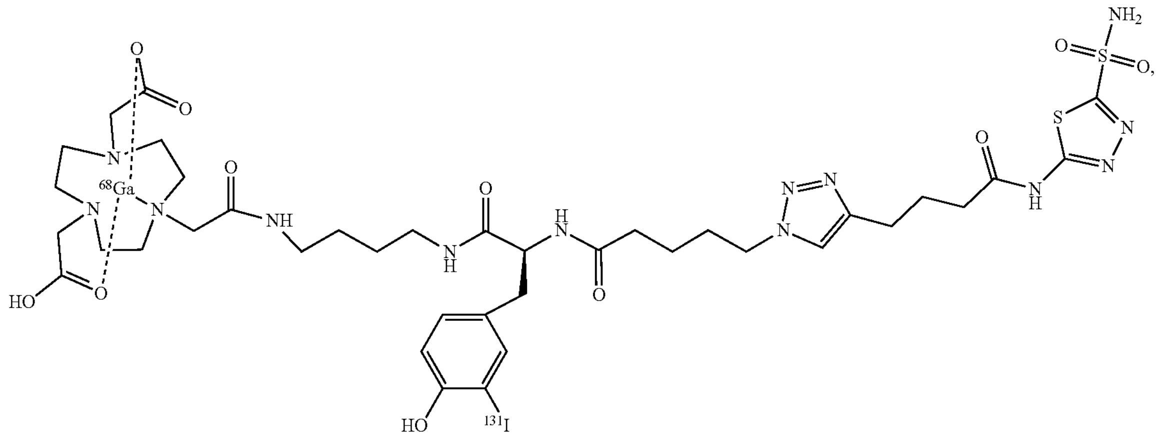

-continued
(13)
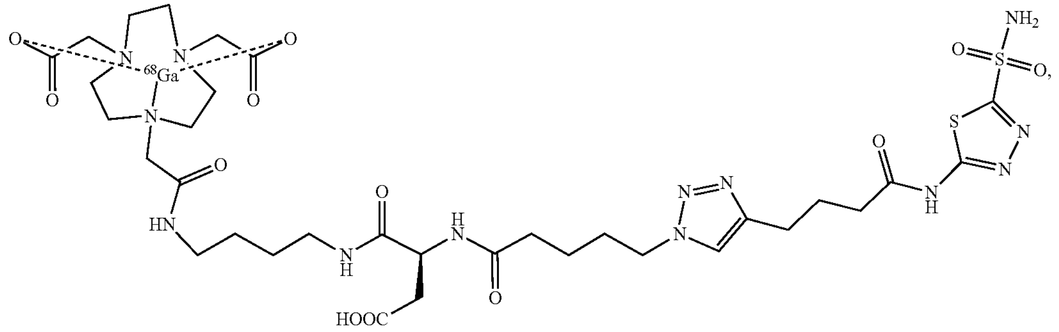
(14)
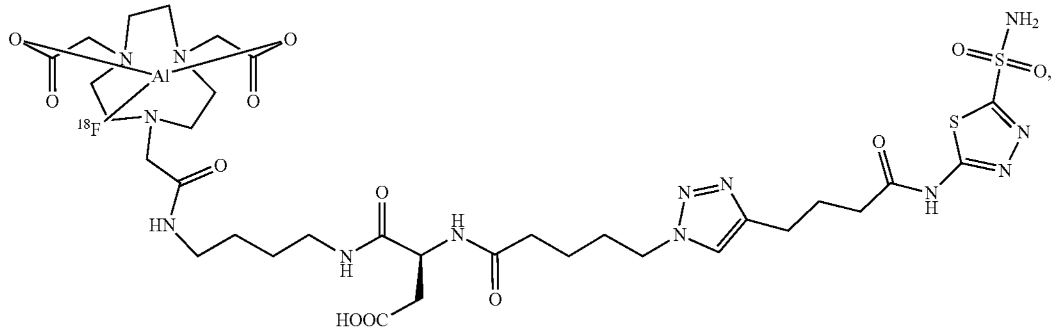
(15)
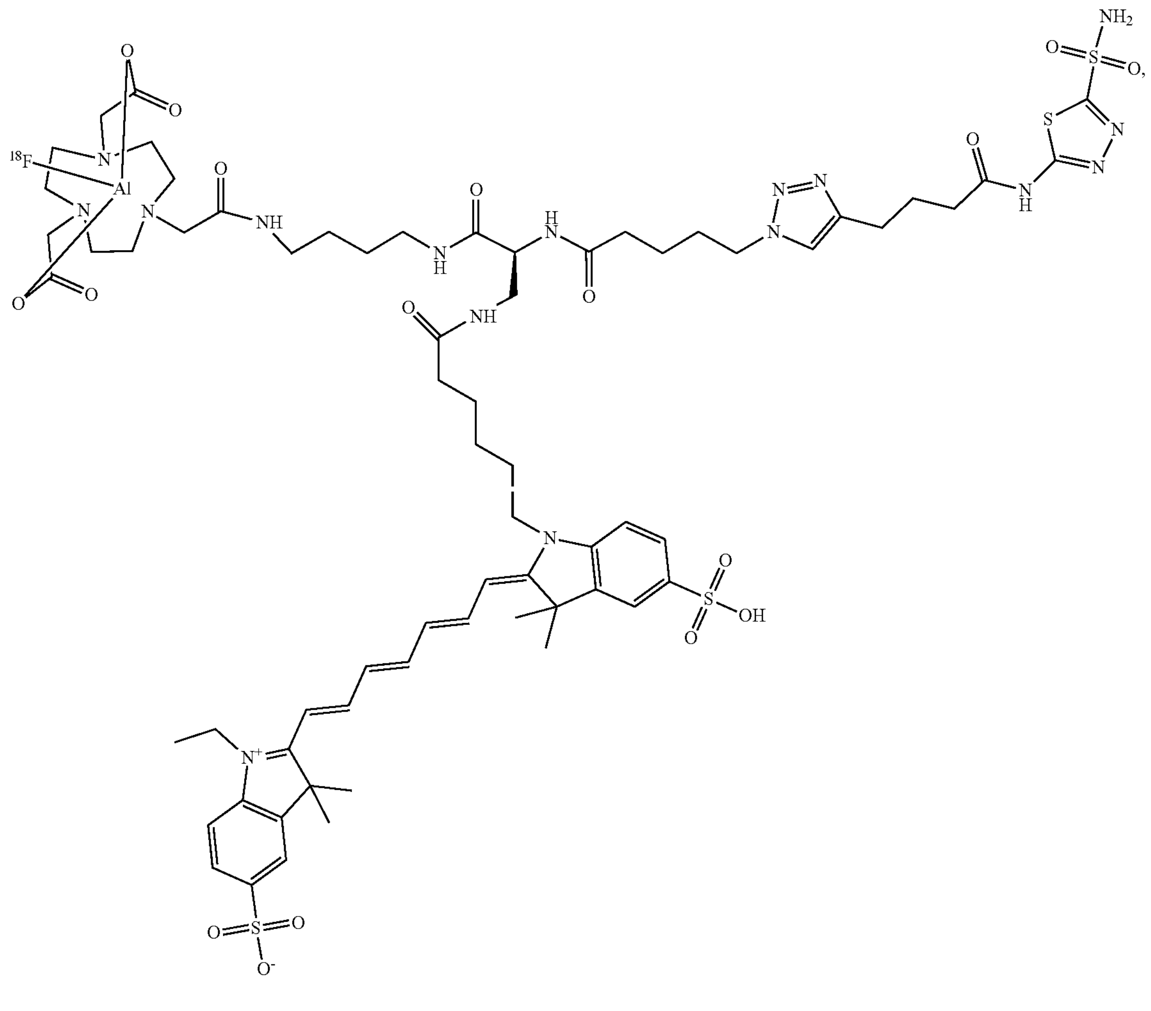

-continued
(16)
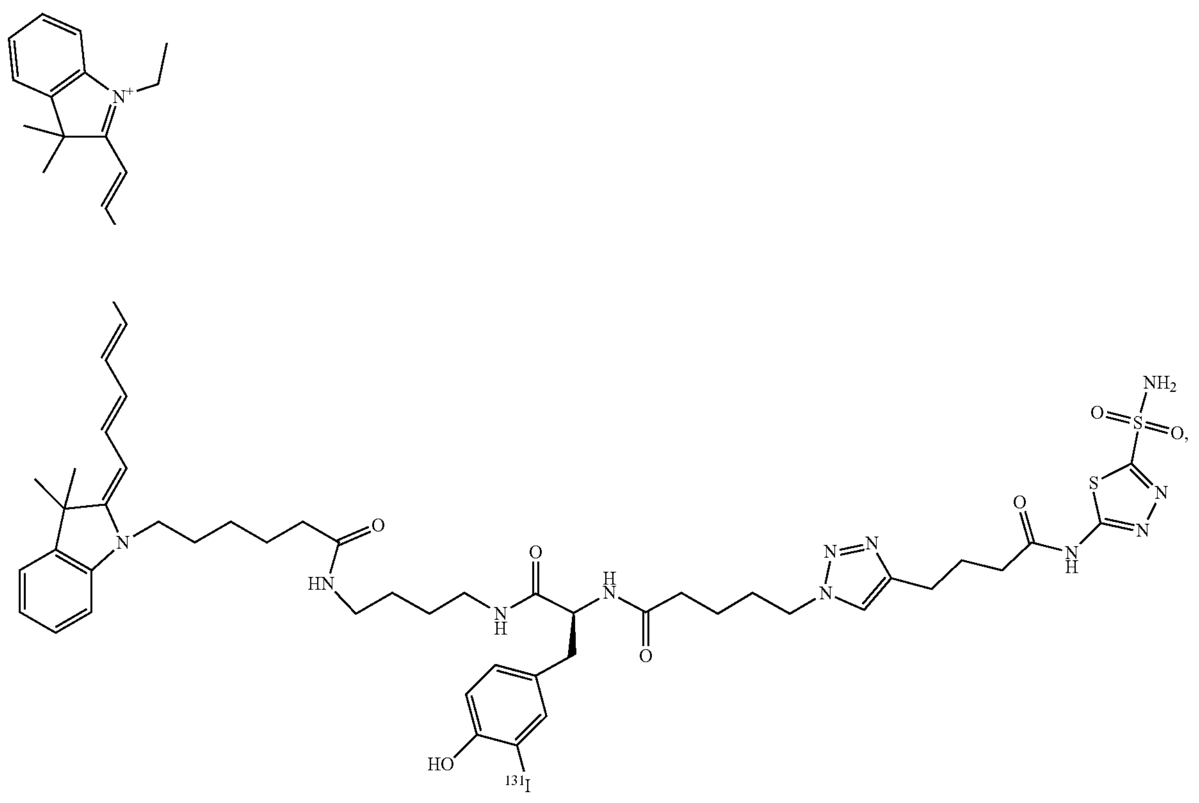
(17)
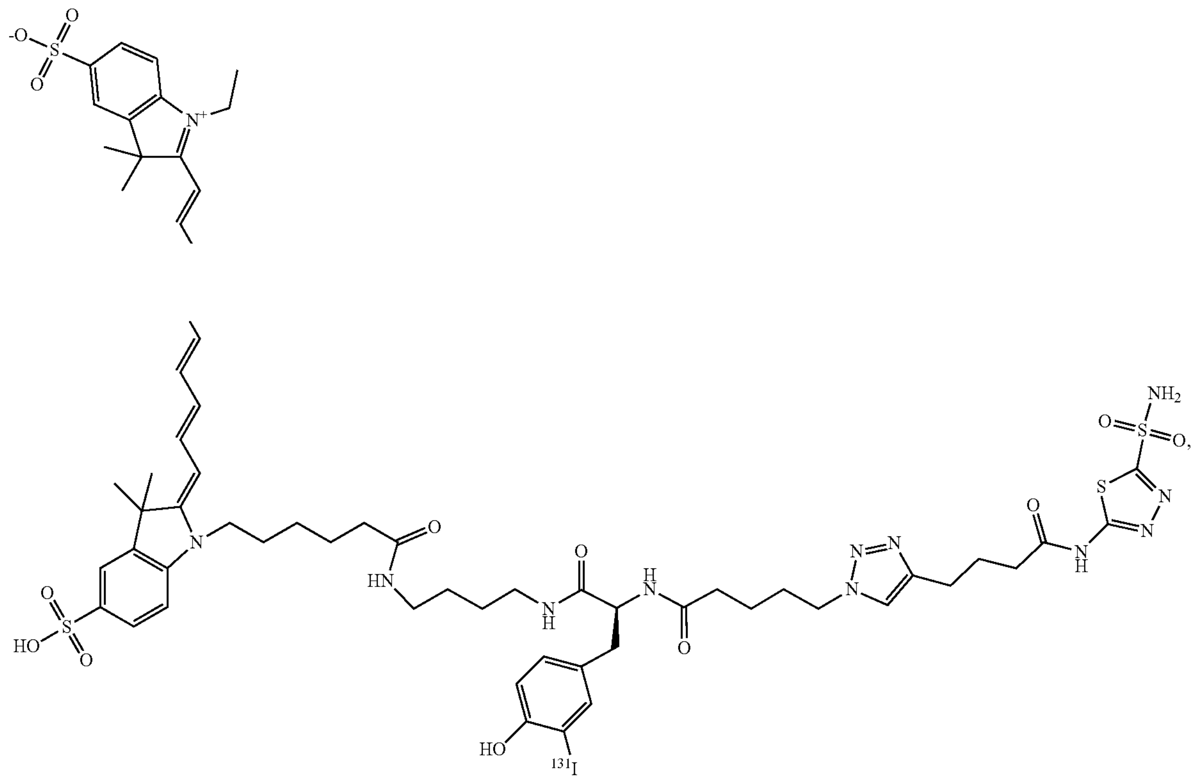

-continued
(18)
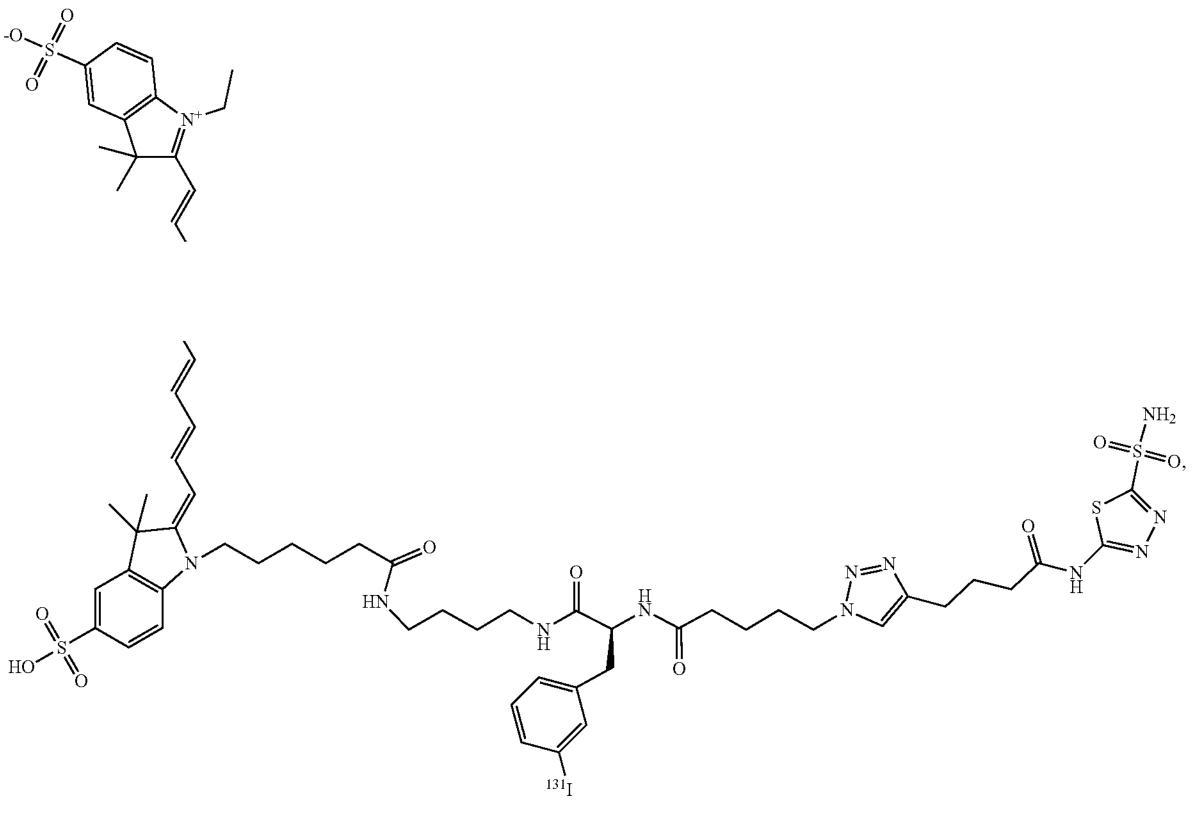
(19)
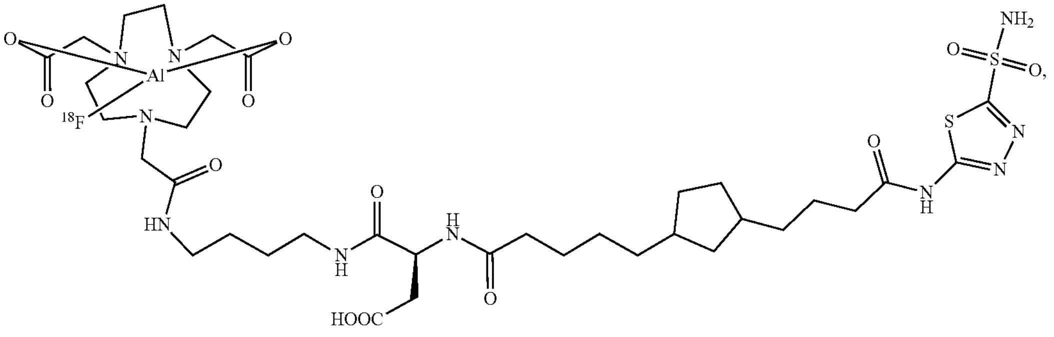
(20)
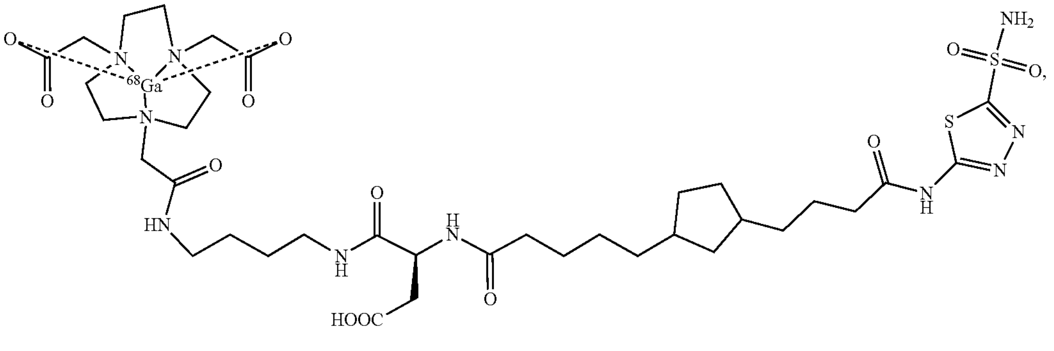

-continued
(21)
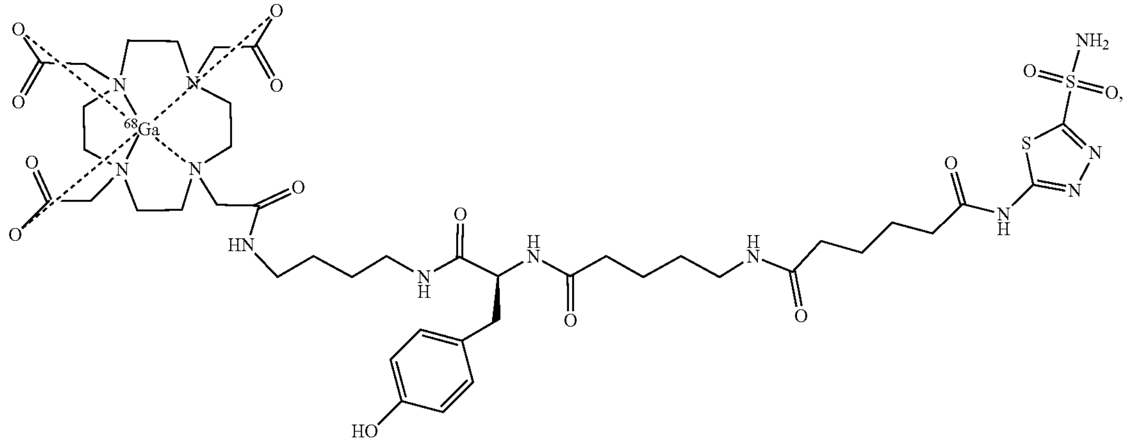
(22)
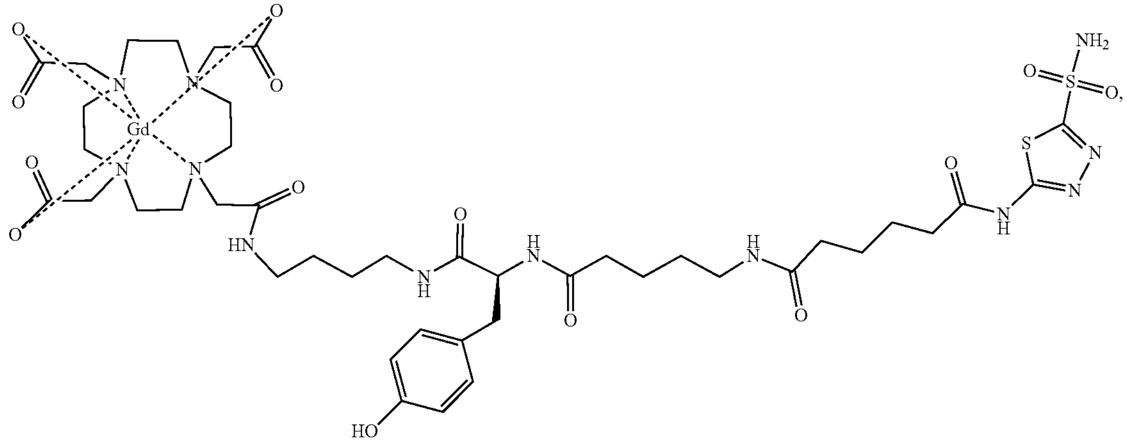
(23)
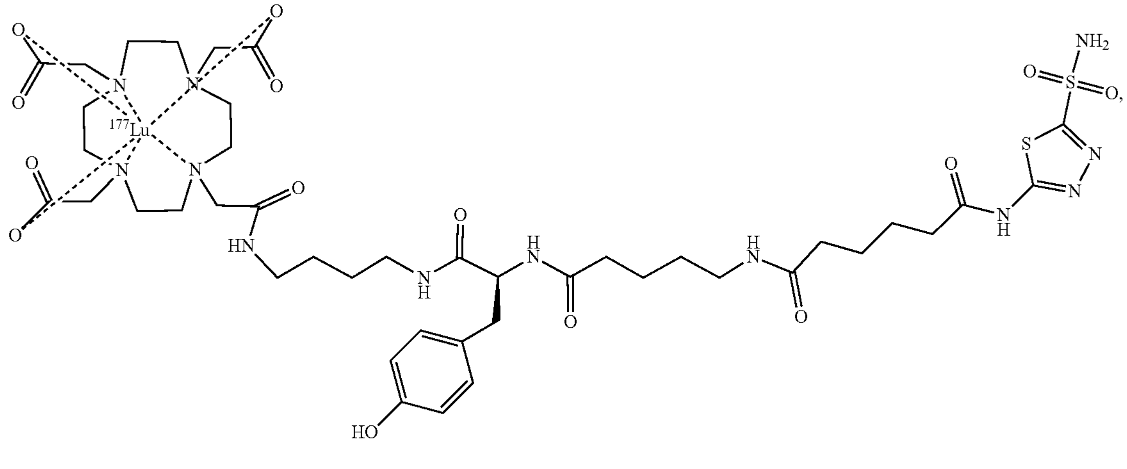

-continued
(24)
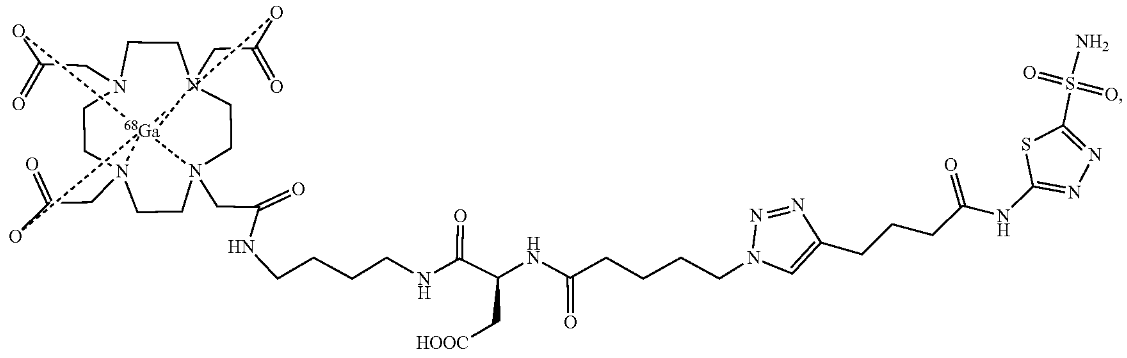
(25)
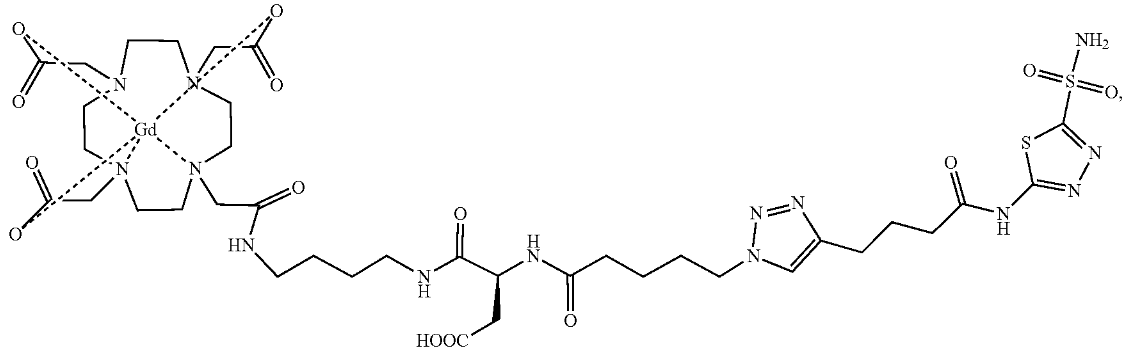
(26)
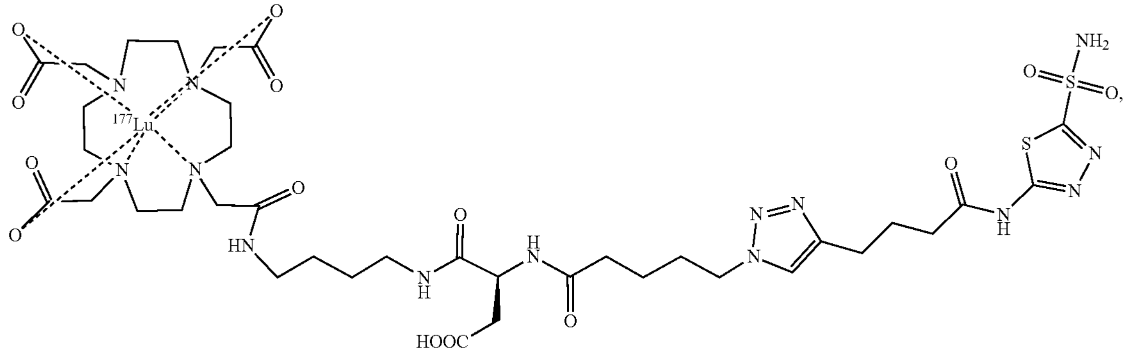
and
(27)
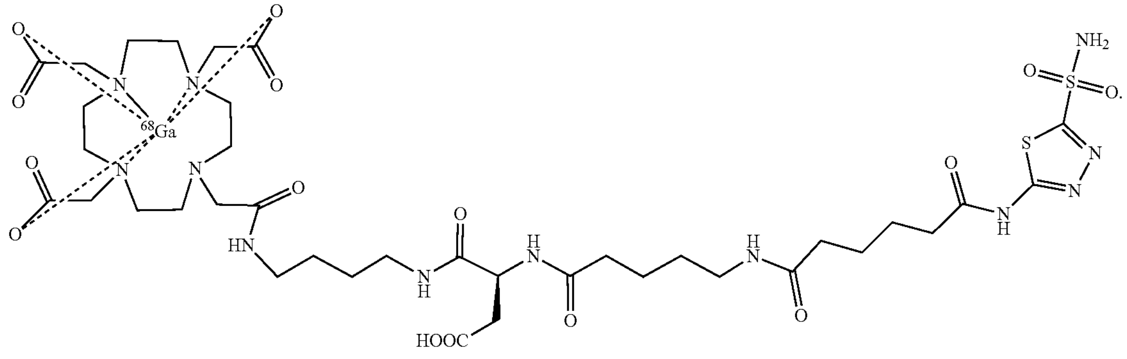

In yet another aspect, the present disclosure further provides a pharmaceutical composition. According to an embodiment of the present disclosure, the pharmaceutical composition includes: the above-mentioned compound, or the pharmaceutically acceptable salt, ester, or solvate thereof; and a pharmaceutically acceptable carrier, excipient, and the like.

In yet another aspect, the present disclosure further provides use of the above-mentioned compound, or the pharmaceutically acceptable salt, ester, or solvate thereof, or the above-mentioned pharmaceutical composition in the preparation of an agent and/or a medicament for diagnosis and/or treatment of one or more tumors, cancers, or cells expressing carbonic anhydrase IX.

In some embodiments of the present disclosure, the above-mentioned diagnosis is in a form selected from optical imaging and/or nuclide imaging.

In some embodiments of the present disclosure, the above-mentioned diagnosis is in a form selected from fluorescence imaging, PET imaging, and/or SPECT imaging.

In some embodiments of the present disclosure, the above-mentioned treatment is selected from radiotherapy and/or surgery assisted by fluorescent surgical navigation.

In some embodiments of the present disclosure, the above-mentioned tumor or cancer is selected from kidney cancer, brain glioma, and other solid tumors, and/or metastatic lesions thereof.

In yet another aspect, the present disclosure further provides use of the above-mentioned compound, pharmaceutically acceptable salt, ester, or solvate thereof, or the above-mentioned pharmaceutical composition in diagnosis and/or treatment of tumors, cancers, or cells expressing carbonic anhydrase IX.

In yet another aspect, the present disclosure further provides use of the above-mentioned compound, pharmaceutically acceptable salt, ester, or solvate thereof, or the above-mentioned pharmaceutical composition in diagnosis and/or treatment of kidney cancer, brain glioma, and other solid tumors, and/or metastatic lesions thereof.

In yet another aspect, the present disclosure further provides a method for diagnosing and/or treating tumors, cancers, or cells expressing carbonic anhydrase IX. According to an embodiment of the present disclosure, the method includes administering a pharmaceutically acceptable dose of the above-mentioned compound, pharmaceutically acceptable salt, ester, or solvate thereof, or the above-mentioned pharmaceutical composition to a patient.

According to an embodiment of the present disclosure, associated disease expressing carbonic anhydrase IX is kidney cancer, brain glioma, and other solid tumors, and/or metastatic lesions thereof.

In yet another aspect, the present disclosure further provides a kit. According to an embodiment of the present disclosure, the kit includes, among other ingredients, the above-mentioned compound, pharmaceutically acceptable salt, ester, or solvate thereof, or the above-mentioned pharmaceutical composition.

In some embodiments of the present disclosure, the kit further includes a pharmaceutically acceptable carrier and excipient, and the remaining variables are as defined in the present disclosure.

In some embodiments of the present disclosure, the above-mentioned pharmaceutically acceptable carrier and excipient include sterile water for injection, acetic acid/sodium acetate buffer solution, and sodium ascorbate.

In some embodiments of the present disclosure, the kit is prepared by the following method: 1) preparing a precursor solution of the above-mentioned compound at a concentration ranging from 0.15 mg/mL to 10 mg/mL using sterile water for injection as a solvent, and dispensing the solution into bottles in amounts from 5 μg/bottle to 50 μg/bottle; 2) preparing an acetic acid/sodium acetate buffer solution (pH 3.5 to 4.5) ranging from 0.2 mol/L to 0.5 mol/L using sterile water for injection as a solvent, and dispensing the solution into bottles in amounts from 0.2 mL/bottle to 2 mL/bottle; and 3) preparing a sodium ascorbate solution ranging from 20 mg/mL to 80 mg/mL using sterile water for injection as a solvent, and dispensing the solution into bottles in amounts from 0.1 mL/bottle to 1 mL/bottle.

In some embodiments of the present disclosure, all of the above-mentioned solutions are prepared in an ultra-clean bench that is overall Class C and partially Class A.

In yet another aspect, the present disclosure further provides use of the above-mentioned kit in diagnosis and/or treatment of tumors, cancers, or cells expressing carbonic anhydrase IX. According to an embodiment of the present disclosure, the diagnosis is in a form selected from optical imaging and/or nuclide imaging.

In some embodiments of the present disclosure, the above-mentioned diagnosis is in a form selected from fluorescence imaging, PET imaging, and/or SPECT imaging.

In some embodiments of the present disclosure, the above-mentioned treatment is selected from radiotherapy and/or surgery assisted by fluorescent surgical navigation.

In some embodiments of the present disclosure, the above-mentioned tumor or cancer is selected from kidney cancer, brain glioma, and other solid tumors, and/or metastatic lesions thereof.

According to the embodiments of the present disclosure, the present disclosure has at least one of the following advantages over the prior art.

1. Source materials for synthesizing the compounds according to the present disclosure are easier to obtain, the synthesis process is simpler and has higher yield.

2. The compound according to the present disclosure adopts water-soluble amino acid having a simple molecular structure and a small molecular weight, which can be easily cleared from normal tissues and organs. In this way, the internal radiation dose of patients during clinical application is decreased, and the process is simpler.

3. In the molecular structures of the compounds according to the present disclosure, linkages with amide bonds and amino acids are mainly used, allowing the molecule to be synthesized using polypeptide solid phase synthesis technology. The resulting smaller molecular weights and fewer synthesis steps greatly reduce the difficulties in terms of the production and control of the chemical composition (CMC) of the molecules in the new drug application process, and further reduce the difficulties of impurity removal.

4. According to the present disclosure, the radioactive nuclide chelating group is combined with the carbonic anhydrase IX-targeting group through optimizing the structure of the molecule According to the current pre-clinical and clinical experimental results, the molecule thus obtained shows good results in radioactive diagnostic imaging (PET/CT or SPECT/CT) and has a good safety profile.

5. The structures of the compounds according to the present disclosure further contain suitable fluorescent groups, through which fluorescent imaging can be achieved, and the fluorescent groups can further assist physicians to carry out fluorescent surgical navigation (after the compound with the fluorescent group is localized to the tumor region, the tumor can emit fluorescent light, while normal tissues do not, allowing the doctors to easily distinguish the tumor tissue from the surrounding healthy tissue during surgery, thereby greatly improving the surgical effect).

Definitions and General Terms

The literature corresponding to the specific contents is listed in detail in the present disclosure, and the embodiments are accompanied by diagrams of structural formulas and chemical formulas. The present disclosure is intended to include all alternatives, modifications, and equivalents, which may be included within the scope of the present disclosure as defined by the claims. Those skilled in the art would know that many methods and materials similar or equivalent to those described herein can be used in the practice of the present disclosure. The present disclosure is not limited to the described methods and materials. Some literature and similar materials may differ from or conflict with the present disclosure, including but not limited to definitions of terms, usage of terms, technology described, which shall be limited within the scope of the present disclosure.

The following definitions are applied in the present disclosure unless otherwise indicated. According to the purposes of the present disclosure, the chemical elements are defined according to the Periodic Table of the Elements, CAS version, and Handbook of Chemical Physics, $75^{th}$ Ed., 1994. In addition, general principles of organic chemistry may refer to "*Organic Chemistry*", Thomas Sorrell, University Science Books, Sausalito, 1999, and "*March's Advanced Organic Chemistry*", Michael B. Smith and Jerry March, John Wiley & Sons, New York, 2007, all of which are incorporated herein by reference.

As described herein, the compounds of the present disclosure may be optionally substituted with one or more substituents, for example the compounds represented by the above general formula, or specific examples, subclasses in the embodiments, and classes of compounds included in the present disclosure. It can be understood that the term "optionally substituted" is used interchangeably with the term "substituted or unsubstituted." In general, the term "optionally", whether the term "substituted" is preceded thereby or not, means that one or more hydrogen atoms in a given structure may or may not be substituted with a specified substituent. Unless otherwise indicated, an optionally substituted group may be a substituent at each substitutable position of the group. When more than one position in a given formula is substituted with one or more substituents selected from a specified group, the substituents may be the same or different at each position. The substituents may include, but are not limited to, deuterium, hydroxyl, amino, halogen, cyano, aryl, heteroaryl, alkoxy, alkylamino, alkylthio, alkyl, alkenyl, alkynyl, heterocyclic, sulfhydryl, nitro, aryloxy, heteroaryloxy, oxo (═O), carboxyl, hydroxy-substituted alkoxy, hydroxy-substituted alkyl-C(═O)—, alkyl-C(═O)—, alkyl —S(═O)—, alkyl-S(═O)$_2$—, hydroxy-substituted alkyl-S(—O)—, hydroxy-substituted alkyl-S(═O)$_2$—, carboxyl-substituted alkoxy, and the like.

Unless otherwise indicated, the term "alkyl" refers to a saturated straight or branched monovalent hydrocarbon group of 1 to 20 carbon atoms, or 1 to 10 carbon atoms, or 1 to 8 carbon atoms, or 1 to 6 carbon atoms, or 1 to 4 carbon atoms, or 1 to 3 carbon atoms. The alkyl may be independently and optionally substituted with one or more substituents described herein, including, but not limited to, deuterium, amino, hydroxyl, cyano, F, Cl, Br, I, mercapto, nitro, oxo (═O), and the like. Examples of alkyl include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)$ $CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2CH_2CH_2CH_3$), 3-methyl-2-pentyl (—$CH(CH_3)$ $CH(CH_3)$ $CH_2CH_3$), 4-methyl-2-pentyl (—$CH(CH_3)$ $CH_2CH(CH_3)_2$), 3-methyl-3-pentyl (—$C(CH_3)$ $(CH_2CH_3)_2$), 2-methyl-3-pentyl (—$CH(CH_2CH_3)$ $CH(CH_3)_2$), 2,3-dimethyl-2-butyl (—$C(CH_3)_2CH(CH_3)_2$), 3,3-dimethyl-2-butyl (—$CH(CH_3)$ $C(CH_3)_3$), n-heptyl, n-octyl, and the like. The term "alkyl" and its prefix "alkane" as used herein include both straight and branched saturated carbon chains. The term "alkylene" as used herein refers to a saturated divalent hydrocarbon group obtained by eliminating two hydrogen atoms from a straight or branched chain saturated hydrocarbon. Examples of "alkylene" include, but are not limited to, methylene, ethylene, iso-propylidene, and the like.

The term "cycloalkyl" refers to a monocyclic, bicyclic, or tricyclic system containing 3 to 12 ring carbon atoms, saturated with one or more points of attachment to the rest of the molecule. In some embodiments, the cycloalkyl is a ring system containing 3 to 10 ring carbon atoms. In other embodiments, the cycloalkyl is a ring system containing 3 to 8 ring carbon atoms. In other embodiments, the cycloalkyl is a ring system containing 3 to 6 ring carbon atoms. In other embodiments, the cycloalkyl is a ring system containing 5 to 6 ring carbon atom. The cycloalkyl groups may be independently unsubstituted or substituted with one or more substituents described herein.

The term "aryl" may be used alone or as a large part of an "arylalkyl", "arylalkoxy", or "aryloxyalkyl" to refer to monocyclic, bicyclic, and tricyclic carbon ring systems containing a total of 6 to 14 membered rings. At least one ring system is aromatic, wherein each ring system contains 3 to 7 membered rings, and has one or more points of attachment to the rest of the molecule. The term "aryl" may be used interchangeably with the term "aromatic ring", for example, aromatic rings may include phenyl, naphthyl, and anthracenyl. The aryl may be substituted or unsubstituted. The substituent may include, but is not limited to, deuterium, hydroxyl, amino, halogen, cyano, aryl, heteroaryl, alkoxy, alkylamino, alkyl, alkenyl, alkynyl, heterocyclic, thiol, nitro, aryloxy, hydroxy-substituted alkoxy, hydroxy-substituted alkyl-C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxyl-substituted alkoxy, and the like.

The term "heteroaryl" may be used alone or as a large part of "heteroarylalkyl" or "heteroarylalkoxy" to refer to monocyclic, bicyclic, and tricyclic ring systems containing a total of 5 to 14 membered rings. At least one ring system is aromatic and at least one ring system contains one or more heteroatoms, wherein the heteroatoms have the meanings described herein. Each ring system contains 3 to 7 membered rings, and has one or more points of attachment to the rest of the molecule. The term "heteroaryl" may be used interchangeably with the terms "heteroaromatic cycle" or "heteroaromatic compound". The heteroaryl may be substituted or unsubstituted, wherein the substituent may include, but is not limited to, deuterium, hydroxyl, amino, halogen, cyano, aryl, heteroaryl, alkoxy, alkylamino, alkyl, alkenyl, alkynyl, heterocyclyl, thiol, nitro, aryloxy, hydroxy-substituted alkoxy, hydroxy-substituted alkyl-C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxyl-substituted alkoxy, and the like.

In other embodiments, the aromatic heterocycle includes, but is not limited to, the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, pyrimidin-5-yl, pyridazinyl (such as 3-pyridazinyl), 2-thiazolyl, 4-thiazolyl, 5-thiazolyl, tetrazolyl (such as 5-tetrazolyl), triazolyl (such as 2-triazolyl and 5-triazolyl), 2-thienyl, 3-thienyl, pyrazolyl (such as 2-pyrazolyl), isothiazolyl, 1,2,3-oxadiazolyl, 1,2,5-oxadiazolyl, 1,2,4-oxadiazolyl, 1,2,3-triazolyl, 1,2,3-thiodiazolyl, 1,3,4-thiodiazolyl, 1,2,5-thiodiazolyl, 1,3,4-thiadiazol-2-yl, pyrazinyl, pyrazin-2-yl, 1,3,5-triazinyl, benzo[d]thiazolyl oxazol-2-yl, imidazo[1,5-a]pyridin-6-yl. The aromatic heterocycle also includes, but is in no way limited to, the following bicycles: benzimidazolyl, benzofuranyl, benzothiophenyl, indolyl (such as 2-indolyl), purinyl, quinolyl (such as 2-quinolyl, 3-quinolyl, and 4-quinolyl), and isoquinolyl (such as 1-isoquinolyl, 3-isoquinolyl, or 4-isoquinolyl).

The term "halogen" refers to F, Cl, Br, and I.

In addition, it should be noted that, unless otherwise explicitly stated, the description method used throughout herein "each of . . . is independently . . . " and " . . . and . . . are each independently . . . " are interchangeable, and should be understood in a broad sense. It may mean that in different groups, the specific options expressed by the same symbols do not affect each other, or in the same group, the specific options expressed by the same symbols do not affect each other. For example, in structure

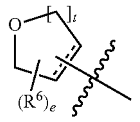

and structure

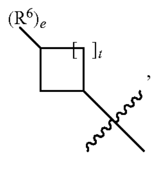

, the specific options of $R_6$ in the two do not affect each other. At the same time, if multiple $R_6$ appear in the same structure, the specific options of multiple $R_6$ do not affect each other, that is, the specific options of $R_6$ may be the same or different.

The definitions and rules of stereochemistry used in the present disclosure generally follow "S. P. Parker, Ed., McGraw-Hill Dictionary of Chemical Terms (1984) McGraw-Hill Book Company, New York; and Eliel, E. and Wilen, S., "*Stereochemistry of Organic Compounds*", John Wiley&Sons, Inc., New York, 1994". The compounds of the present disclosure may contain an asymmetric center or chiral center, and thus different stereoisomeric forms may exist. All stereoisomeric forms of the compound of the present disclosure, including, but not limited to, diastereoisomers, enantiomers, atropisomers, and mixtures thereof such as racemic mixtures, shall be fall within the scope of the present disclosure. Many organic compounds exist in optically active forms, i.e., they are capable of rotating a plane of plane-polarized light. When describing optically active compounds, the prefixes/) and L, or R and S are used to denote the absolute configurations of the molecular chiral centers. The prefixes/) and I, or (+) and (−) are symbols used to specify a rotation of plane-polarized light caused by a compound, where (−) or L indicates that the compound is levorotatory, and the prefix (+) or D indicates that the compound is dextrorotatory. These stereoisomers have identical chemical structure but have different stereo-structures. The specific stereoisomers may be enantiomers, and a mixture of such isomers is generally called an enantiomeric mixture. A mixture of enantiomers in 50:50 is called a racemic mixture or a racemate, which may cause there to be no stereoselectivity or stereospecificity in a chemical reaction process. The terms "racemic mixture" and "racemate" refer to an equimolar mixture of two enantiomers that lack optical activity.

The term "tautomer" or "tautomeric form" refers to structural isomers of different energies that are interconvertible via a low energy barrier. For example, proton tautomers (i.e., prototropic tautomers) include interconversions via migration of a proton, such as keto-enol and imine-enamine isomerizations. Atomic valence (chemical valence) tautomers include interconversions that reorganize bonding electrons.

As used herein, the term "pharmaceutically acceptable salt" refers to an organic and inorganic salt of the compound of the present disclosure. Pharmaceutically acceptable salts are well known in the art, such as recorded in S. M. Berge et al., *J. Pharmaceutical Sciences,* 66,1-19, 1977. Non-toxic acid form of the pharmaceutically acceptable salt includes, but is not limited to, inorganic acid salts formed by reaction with amino groups, such as hydrochlorides, hydrobromides, phosphates, sulfates, perchlorates, and organic acid salts, such as acetates, oxalates, maleates, tartrates, citrates, succinates, malonates, or salts obtained by other methods described in the literature, such as ion exchange method. Other pharmaceutically acceptable salts include adipate, alginate, ascorbate, aspartate, benzenesulfonate, benzoate, bisulfate, borate, butyrate, camphorate, camphorsulfonate, cyclopentylpropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, etc. Salts derived from appropriate bases include alkali metal, alkaline earth metal, ammonium, and salts of $N^+(C_{1\ to\ 4}\ alkyl)_4$. The present disclosure also contemplates quaternary ammonium salts formed by any compound containing a N group. Water-soluble, or oil-soluble, or dispersible products may be obtained by quaternization. Alkali metal or alkaline earth metal salts include sodium, lithium, potassium, calcium, magnesium, etc. Pharmaceutically acceptable salts further include suitable, non-toxic ammonium/quaternary ammonium salts and amine cations resistant to the formation of equilibrium ions, such as halides, hydroxides, carboxylates, sulfates, phosphates, nitrates, $C_{1\ to\ 8}$ sulfonates, and aromatic sulfonates.

The "solvate" in the present disclosure refers to an association formed by one or more solvent molecules with the compound of the present disclosure. Solvents for forming the solvates include, but are not limited to, water, isopropanol, ethanol, methanol, dimethyl sulfoxide, ethyl acetate, acetic acid, and aminoethanol. The term "hydrate" refers to an association in which the solvent molecule is water.

As used herein, the term "treating" or "treatment" may include reversing, alleviating, inhibiting the development of the disease, preventing or reducing the disease or condition to which the term applies, or one or more symptoms or manifestations of the disease or condition.

The term "preventing" or "prevention" means not causing a disease, condition, symptom, or manifestation, or worsening of severity. Thus, the multiple compounds of the present disclosure may be administered prophylactically to prevent or reduce the occurrence or recurrence of the disease or condition.

As used herein, the term "treating" any disease or disorder refers to all measures that can slow down, interrupt, prevent, control, or stop the progression of the disease or disorder, but does not necessarily mean that all symptoms of the disease or disorder disappear. It also includes preventive treatment of the symptoms, especially in patients who are prone to such diseases or disorders. In some of these embodiments, "treating" refers to improve the disease or condition (i.e., the progression of the disease or at least one clinical symptom thereof is slowed, or arrested, or alleviated). In other embodiments, "treating" or "treatment" refers to alleviating or ameliorating at least one physical parameter, including physical parameters that may not be noticeable to the patient. In other embodiments, "treating" refers to modulating the disease or condition physically (e.g., stabilization of observable symptoms) or physiologically (e.g., stabilization of a bodily parameter), or both. In other embodiments, "treating" or "treatment" refers to preventing or delaying the onset, occurrence, or worsening of a disease or condition.

As used herein, the term "therapeutically effective amount" or "therapeutically effective dose" refers to the amount of the compound of the present disclosure that can trigger a biological or medical response in an individual (e.g., reducing or inhibiting enzyme or protein activity, or alleviating symptoms, alleviating disorders, slowing or delaying disease progression, or preventing disease, etc.). In a non-limiting embodiment, the term "therapeutically effective amount" refers to an amount of a compound of the present disclosure that, when administered to an individual, is effective in the following aspects: (1) at least partially alleviating, inhibiting, preventing, and/or ameliorating (i) a condition or disease mediated by carbonic anhydrase IX, or (ii) a condition or disease associated with activity of carbonic anhydrase IX, or (iii) a condition or disease characterized by abnormal activity of carbonic anhydrase IX; (2) reducing or inhibiting the activity of carbonic anhydrase IX; or (3) reducing or inhibiting the expression of carbonic anhydrase IX. In another embodiment, the term "therapeutically effective amount" refers to an effective amount of a compound of the present disclosure that, when administered to a cell, or an organ, or a non-cellular biological substance, or a medium, may at least partially reduce or inhibit the activity of carbonic anhydrase IX; or at least partially reduce or inhibit the expression of carbonic anhydrase IX.

As used herein, the terms "administration" of a compound and "administering" a compound should be understood as providing a compound of the present disclosure, or a salt, ester, or solvate thereof to an individual in need thereof. It should be appreciated that one skilled in the art may treat a patient currently suffering from a disease expressing carbonic anhydrase IX, such as renal cancer, brain glioma, and other solid tumors and/or metastatic lesions thereof, by using an effective amount of the compound of the present disclosure.

The following abbreviations are used throughout the present disclosure:

DOTA represents 1,4,7,10-tetraazacyclododecane-N,N',N'',N''',-tetraacetic acid; NOTA represents 1,4,7-triazacyclononane-1,4,7-triacetic acid; NODAGA represents 2-(4,7-bis (carboxymethyl)-1,4,7-triazonon-1-yl) pentanedioic acid; DOTAGA represents 2-(4,7,10-tris (carboxymethyl)-1,4,7,10-tetraazacyclododecan-1-yl) pentanedioic acid; TRAP represents 1,4,7-triazacyclononane phosphinic acid; NOPO represents 1,4,7-triazacyclononane-1-[methyl (2-carboxyethyl) phosphinic acid]-4,7-bis [methyl (2-carboxymethyl) phosphinic acid]; DFO represents N'-{5-[acetyl (hydroxy) amino]pentyl}-N-[5-({4-[5-amino pentyl) (hydroxy) amino]-4-oxobutanoyl}amino) pentyl]-N-hydroxysuccinamide; DTPA represents diethylenetriaminepentaacetic acid; CHX-DTPA represents trans-cyclohexyl-diethylenetriaminepentaacetic acid; SCN-Bz-DTPA represents p-isothiocyanatobenzyl-DTPA; 1B3M represents 1-(isothiocyanatobenzyl)-3-methyl-DTPA; 1B3B represents 1-(isothiocyanatobenzyl)-4-methyl-DTPA; MX-DTPA represents 1-(2)-methyl-4-isocyanatobenzyl-DTPA; OXY-Do3A represents 2-oxa-4,7,10-triazacyclododecane-4,7,10-triacetic acid; HYNIC represents succinimidyl 6-hydraziniumnicotinate hydrochloride; and MAG3 represents mercaptoacetyl triglycine.

The sulfonated-Cy7 fluorescent group has a structure as follows:

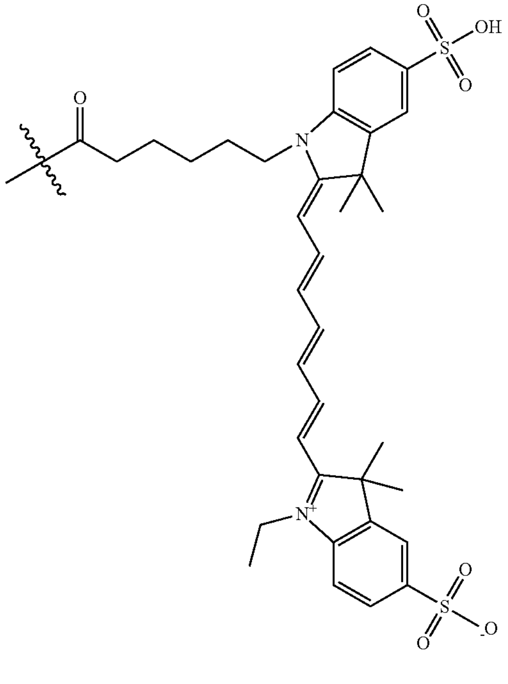

or

-continued
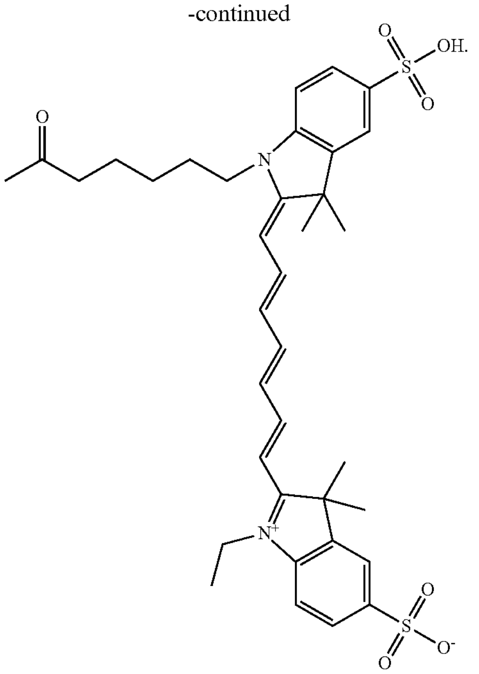
Example 1
Formula (II)
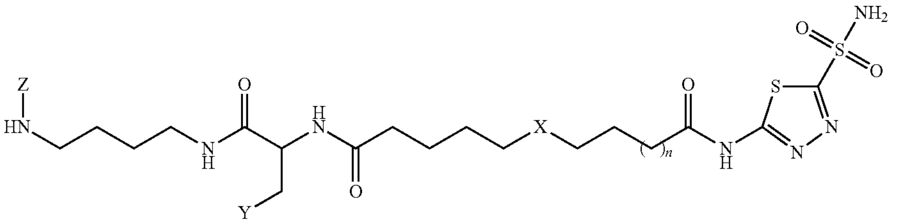
Synthetic Scheme:
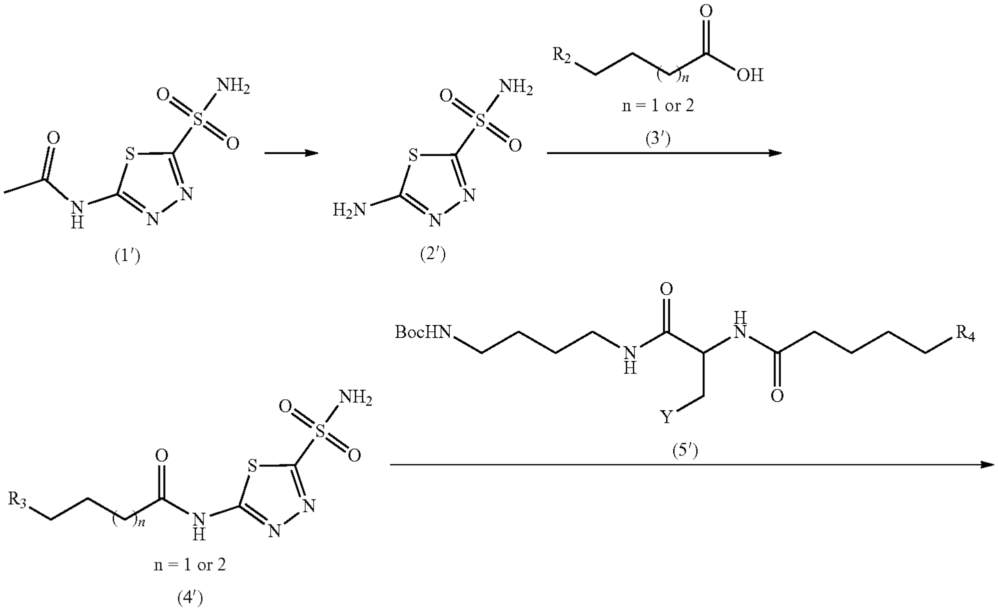

-continued

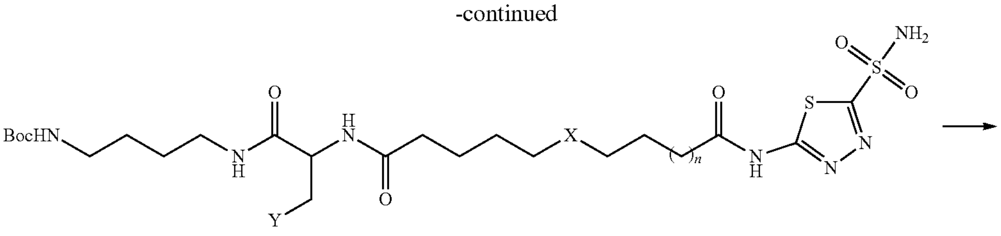

n = 1 or 2

(6')

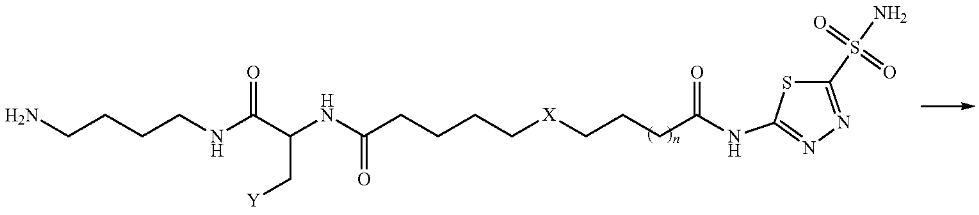

n = 1 or 2

(7')

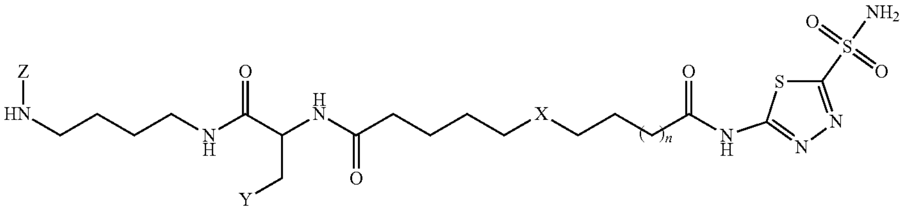

n = 1 or 2

(I)

First, acetazolamide (1') was hydrolyzed under acidic conditions to obtain compound (2'). Compound (2') was subjected to an amide condensation reaction with fatty carboxylic acid (3') to generate compound (4'). Subsequently, $R_3$ functional group in the structure of compound (4') was subjected to an amide condensation reaction or a [3+2] cycloaddition reaction with $R_4$ functional group in the structure of compound (5) to generate compound (6'), $R_3$ being terminal acetenyl or carboxyl, and $R_4$ being azido or amino group. Compound (6') was subjected to removal of Boc protecting group under suitable strong acidic conditions to obtain compound (7'). Finally, compound (7') was subjected to a condensation reaction with carboxyl group on a chelating group or a fluorescent group, or an active ester thereof, to obtain the target compound (I).

Example 2: Preparation Process of NYM005 Molecule

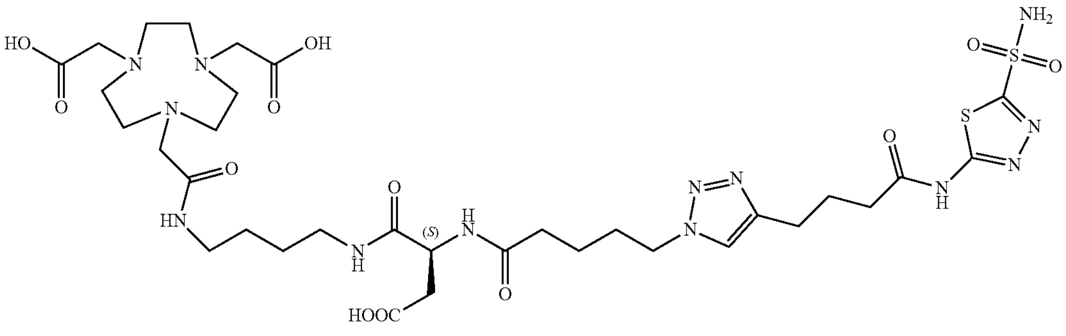

Structure of NYM005 molecule

Figure 2:
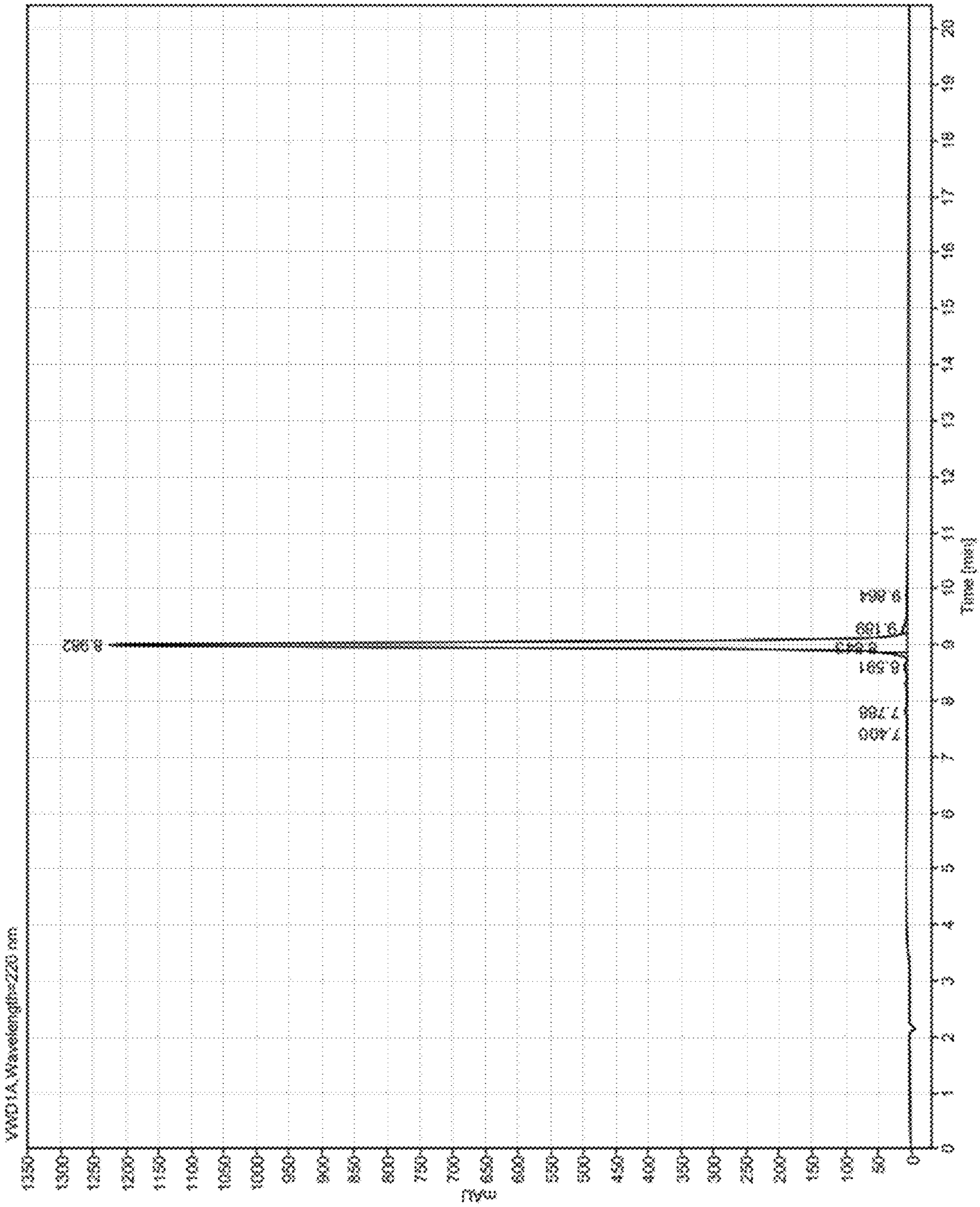
FIG. 2 is a High Performance Liquid Chromatography (HPLC) diagram of NYM005 molecule according to an embodiment of the present disclosure.

LC-MS spectrum of NYM005 molecule can refer to FIG. 1, and HPLC spectrum of NYM005 molecule can refer to FIG. 2.

Synthetic Scheme:

Step 1:

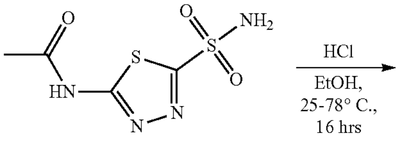

1b

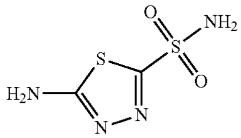

2b

Compound (1b) (5.00 g, 22.5 mmol, 1.00 eq) was added to 50 mL of EtOH solvent, and hydrochloric acid (12.0 M, 7.50 mL, 4.00 eq) was added at 25° C. The mixture was refluxed at 78° C. for 16 hours. When the results of thin layer chromatography (TLC) (volume ratio: dichloromethane: methanol=5:1) indicated that a new compound was generated, the reaction solution was cooled to 25° C., and the reaction mixture was poured into water (30.0 mL). Saturated sodium bicarbonate was added to adjust pH to 7, and the system was extracted with ethyl acetate for three times, using 30 mL of ethyl acetate each time (30.0 mL*3). The organic layer after extraction was washed with 30 mL of saturated brine, and then dried over anhydrous sodium sulfate. The solvent was evaporated under reduced pressure to obtain a residue. The residue was a yellow oil (2b) (12.0 g, 35.0 mmol).

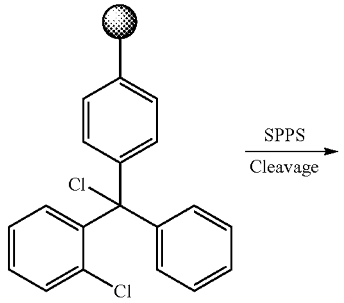

4b

Step 2:

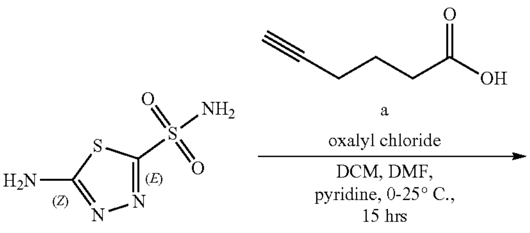

2b a

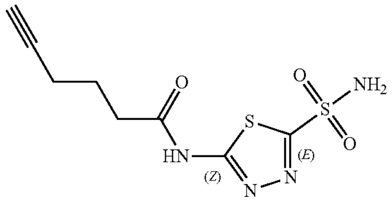

3b

Compound (a) (2.00 g, 17.8 mmol, 1.94 mL, 1.00 mL) was added to DCM solvent (20.0 mL), and DMF (65.1 mg, 891 μmol, 68.6 μL, 0.05 eq) was added to the solution. The solution was cooled to 0° C., oxalyl dichloride (2.15 g, 16.9 mmol, 1.48 mL, 0.95 eq) was added dropwise, and the mixture was stirred at 20° C. for 3 hours. The reaction mixture was concentrated under pressure to obtain hex-5-ynoyl chloride (2.03 g, 15.5 mmol) as a yellow oil.

Compound (2b) (2.70 g, 14.9 mmol, 1.00 eq) and pyridine (2.37 g, 29.9 mmol, 2.42 mL, 2.00 eq) were added to DMF solvent (28.0 mL) to form a mixture, and the mixture was cooled to 0° C. Hex-5-ynoyl chloride (1.96 g, 14.9 mmol, 1.00 eq) was dissolved in DCM solvent (20.0 mL) and added dropwise to the previous mixture at 0° C., and stirred at 25° C. for 12 hours. The reaction mixture was concentrated under reduced pressure, and the solvent was removed to obtain a residue. The residue was purified by preparative HPLC to obtain a white solid compound (3b) (2.75 g, 9.95 mmol).

Step 3:

Synthesis of Polypeptide: Polypeptide was Synthesized Using a Fmoc Synthesis Method.

-continued

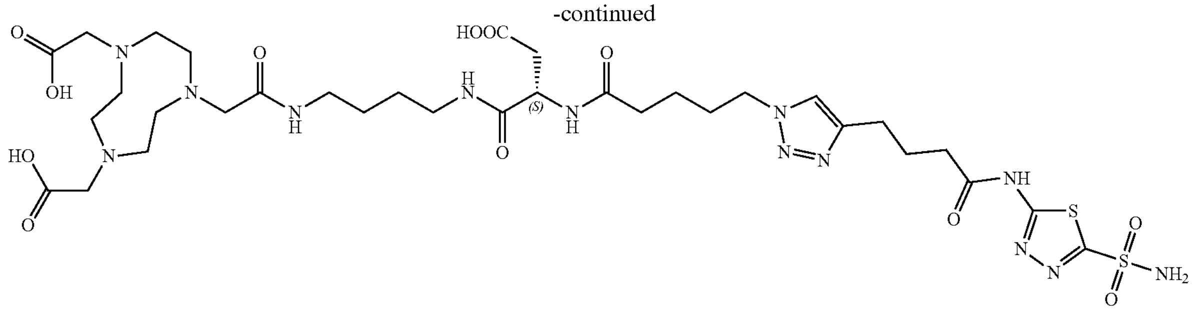

NYM005

1. Preparation of resin: 20.0 mL of DCM solution containing Fmoc-Asp-OAll (1.00 mmol, 1.00 eq) and DIEA (4.00 mmol, 4.00 eq) was added to 2-CTC resin (1.00 mmol, 1.00 eq), and the mixture was purged with nitrogen at 20° C. and stirred for 2 hours for reaction. MeOH (1.00 mL) was added, and the mixture was further stirred for 30.0 minutes. The resin was then washed with DMF for five times, using 20.0 mL of DMF each time (20.0 mL*5).

2. Deprotection: DMF solution (20.0 mL) containing 20% (v/v) piperidine was added to the resin, and the mixture was stirred for 30.0 minutes under nitrogen purge. The resin was washed and filtered with DMF for five times, using 20.0 mL of DMF each time (20.0 mL*5).

3. Coupling: 5-azidopentanoic acid (3.00 mmol, 3.00 eq) was added into DMF solvent (10.0 mL), and HATU (3.00 mmol, 3.00 eq) and DIEA (6.00 mmol, 6.00 eq) were added. The mixture was added into the resin and stirred for 30 minutes at 20° C. under nitrogen purge. The resin was washed with DMF for five times, using 20.0 mL of DMF each time (20.0 mL*5).

4. Compound (3b) (3.00 mmol, 3.00 eq), CuI (0.50 mmol, 0.50 eq), and DIEA (4.00 mmol, 4.00 eq) were added into DMF solvent (20.0 mL), and the mixture was stirred for 16 hours at 20° C. under nitrogen purge. Then, the resin was washed with DMF for five times, using 20.0 mL of DMF each time (20.0 mL*5).

5. Deprotection: $PhSiH_3$ (10.0 mmol, 10.0 eq) and $Pd(PPh_3)_4$ (0.10 mmol, 0.10 eq) were added to the resin, and the mixture was stirred under nitrogen purge for 3 times, 15 minutes each time. The resin was washed and filtered with DMF for five times, using 20.0 mL of DMF each time (20.0 mL*5).

6. The above steps 2 to 3 were repeated to couple amino acids in Table 1.

TABLE 1

| Amino acid to be fed | Coupling reagent |
|---|---|
| N-Fmoc-1,4-Diaminobutane HCl (3.00 eq) | HOAT (3.00 eq), DIC (3.00 eq) |
| NOTA-bis(tBu)ester (1.50 eq) | HOAT (1.50 eq), DIC (1.50 eq) |

7. The resin was washed with DMF for five times, using 20.0 mL of DMF each time (20.0 mL*5), and filtered to obtain the polypeptide (4b).

8. Cleavage and purification of polypeptide:

The resin was washed with MeOH for three times, using 20.0 mL of MeOH each time (20.0 mL*3), and dried under vacuum to obtain 2.0 g of polypeptide resin (4b). Polypeptide with side chain protecting groups was added into a flask, and 20 mL of lysis buffer (92.5% TFA/2.5% TIS/2.5% $H_2O$/2.5% MPR) was added. The mixture was stirred at 20° C. for 2 hours for deprotection, precipitated with tert-butyl methyl ether (100 mL), and centrifuged (3.00 min, 3000 rpm). Peptide precipitate was washed twice with tert-butyl methyl ether (100.0 ml). The obtained product was dried under vacuum for 2 hours to obtain 0.821 g of crude product.

The crude product was purified by preparative HPLC (TFA conditions: A: 0.075% TFA in $H_2O$ solution, B: ACN) to obtain the target product NYM005 (105 mg, 101 μmol, purity 96.30%) as a white solid.

Example 3: Preparation Process of $^{68}$Ga-NYM005

The synthesized NYM005 precursor was subjected to a chelation reaction with radioactive nuclide gallium [$^{68}$Ga] to further obtain a $^{68}$Ga-NYM005 tracer approved for clinical PET/CT tracing. The labeling technology was mature, and a radiochemical purity of the labeled product radioactive compound may usually reach 99%.

The labeling process is shown below. The entire labeling process can be completed within 20 minutes, and yield of the radioactive compound can reach 70%.

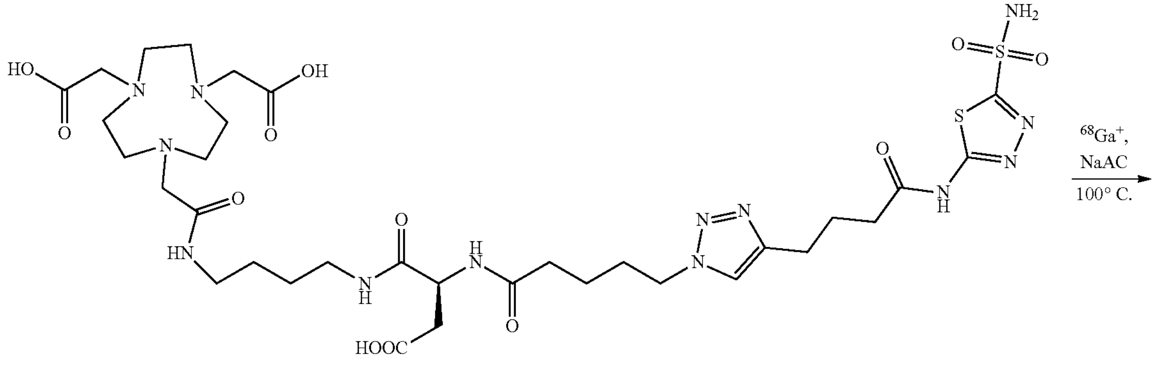

-continued

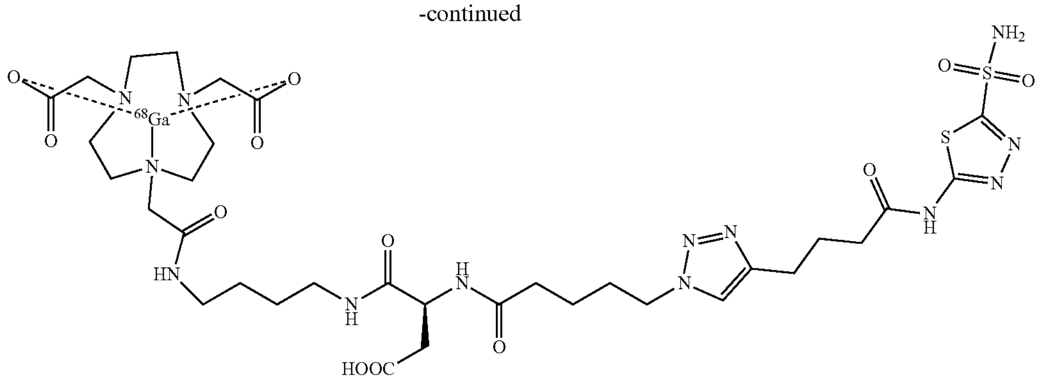

The method for labeling NYM005 with $^{68}Ga$ in Example 3 included the following specific steps. $^{68}Ga$ nuclide was obtained by eluting a germanium gallium generator with a 0.05M hydrochloric acid solution. 1 mL of the $^{68}Ga$ nuclide (20 mCi) solution was added to a reaction bottle, then 1 mL of 0.3 mol/L acetic acid/sodium acetate buffer solution was added to the reaction bottle, allowing a volume ratio of $^{68}Ga$ nuclide to the buffer solution was 1:1, and pH value was adjusted to 4.0. An appropriate amount of NYM005 precursor compound was taken and added to sterilized water for injection to prepare a 1 mg/mL precursor solution. Then, 45 nmol (40 μg) of the precursor solution was taken and added to the reaction bottle, and the mixture reacted for 6 minutes at 105° C. After the reaction was completed, the reaction mixture was cooled for 1 minute. 5 mL of sterilized water for injection was taken using a 10 mL sterile syringe and added to the reaction bottle to dilute the reaction solution while lowering the temperature of the reaction solution. Then, all the liquid in the reaction bottle was sucked into the syringe. Pre-activated Sep-Pak C-18 column was taken and connected to an outlet of the syringe. The reaction dilution was pushed to flow through the Sep-Pak C-18 column, and the target product $^{68}Ga$-NYM005 was adsorbed by the C-18 column. Then, the C-18 column was eluted with 1 mL of 70% medical grade anhydrous ethanol solution, and the eluted solution was filtered through a 0.22 μm sterile filter membrane and flowed into a sterile vacuum bottle. Then, 4 mL of physiological saline solution was added to obtain a $^{68}Ga$-NYM005 sterile injection solution.

Figure 3:
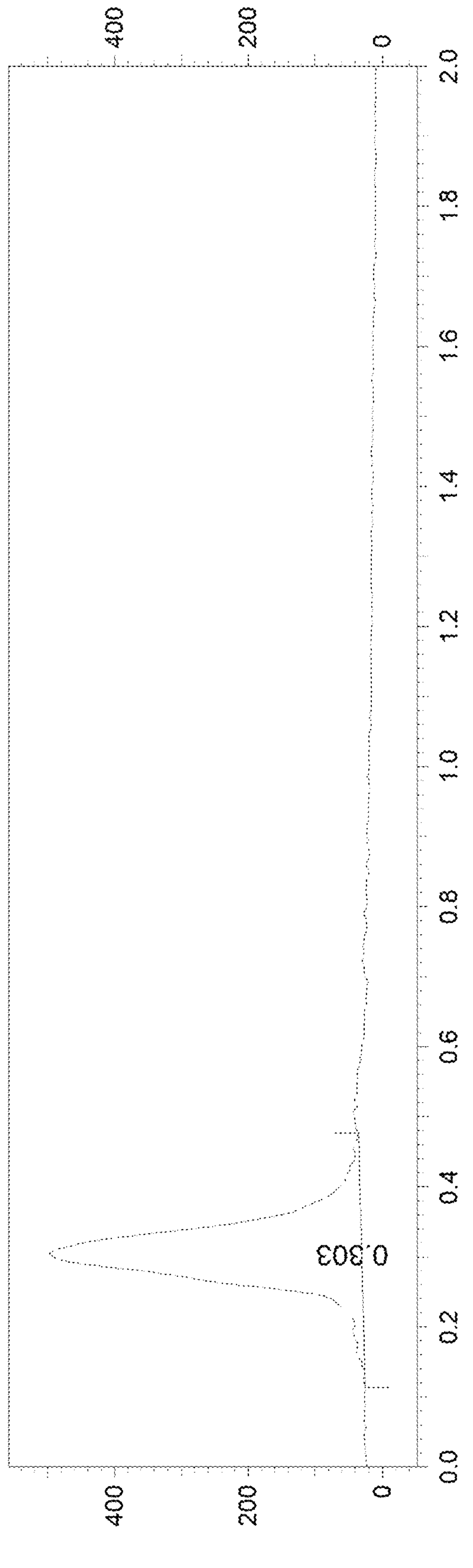
FIG. 3 is a graph of results of radioactive thin layer chromatography scanning purity analysis of $^{68}$Ga-NYM005 molecule according to an embodiment of the present disclosure.

Radioactive thin layer chromatography was used for quality control of the above products, using a carrier of glass fiber paper and a developing agent of 0.5 M citric acid/sodium citrate buffer (pH=5). The glass fiber paper was taken and the sample was transferred using a pipette and tapped gently on the glass fiber paper at a position 1.5 cm from the bottom. Then, the glass fiber paper was put into a tube with 500 μL of 0.5 M citric acid/sodium citrate buffer (pH=5) added in advance, expanded to a position 2.5 cm from the top of the chromatography paper, and the paper was taken out and dried, and detected with a Radio-TLC thin layer scanner. In 0.5 M citric acid/sodium citrate buffer (pH=5) system, Rf value of the product ranges from 0.3 to 0.6. As shown in FIG. 3, according to the results of radioactive thin layer chromatography scanning purity analysis of $^{68}Ga$-NYM005 molecule, the radioactive compound had a radiochemical purity of 100%.

Example 4: Preparation Process of $^{18}F$-NYM005

Figure 25:
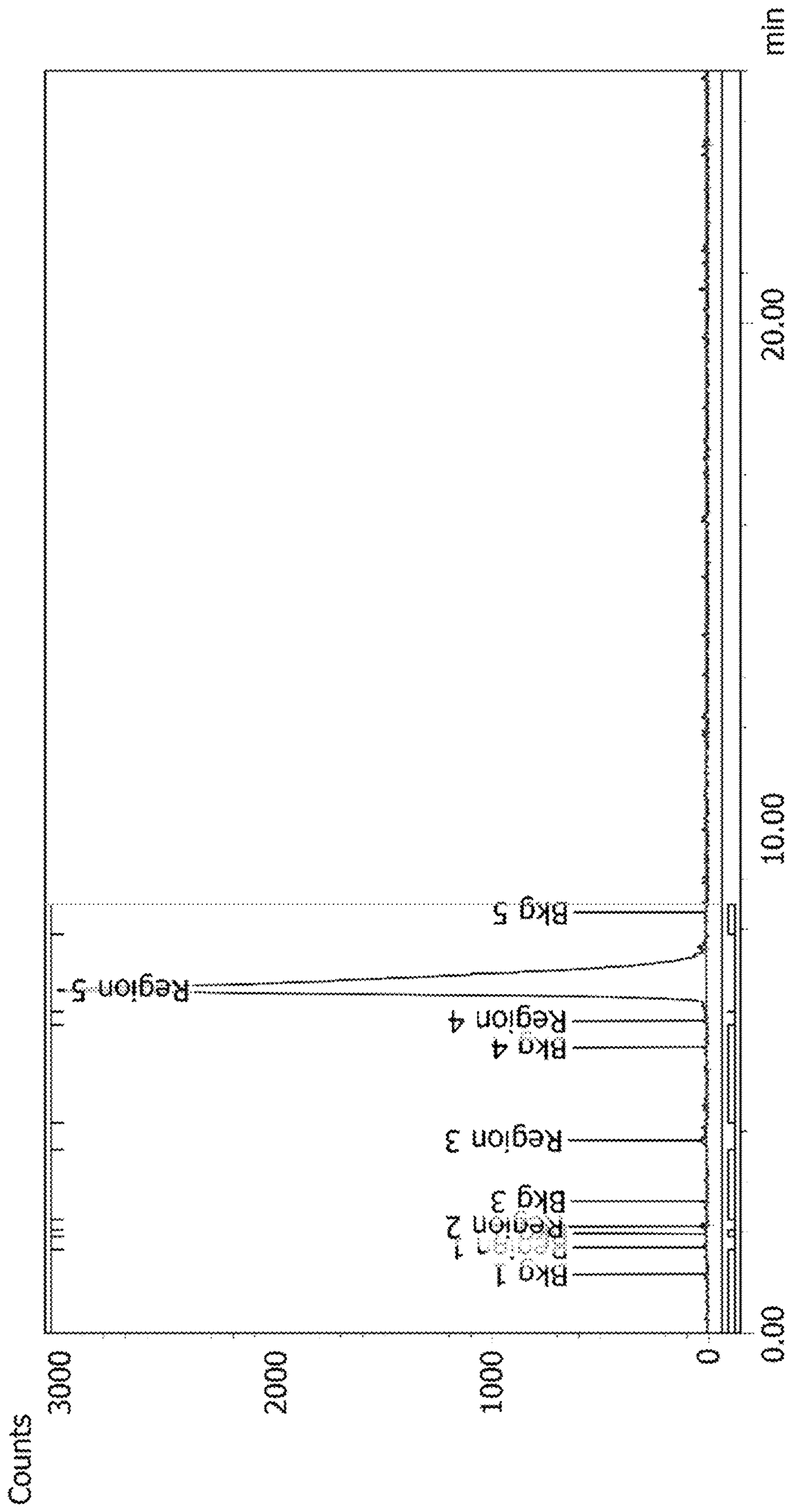
FIG. 25 is a High Performance Liquid Chromatography (HPLC) diagram of $^{18}$F-NYM005 according to an embodiment of the present disclosure.

2.5 mL of acetonitrile, 24 μL of an aqueous solution containing the precursor NYM005 (10 mg/ml), 45 μL of $AlCl_3$ (2 mM, aqueous solution), and 45 μL of acetic acid were added to a reaction bottle. An aqueous solution of 180 containing $^{18}F$ produced by a particle accelerator was loaded onto an activated QMA column, and then eluted with 0.5 mL of normal saline. The eluate entered the reaction bottle, and the reaction bottle was then sealed and capped. The mixture reacted at 75° C. for 15 minutes. After the reaction was completed, the reaction bottle was cooled to room temperature. 6 mL of sterile water for injection was added to the reaction bottle to dilute the reaction solution. 3 mL of the diluted reaction solution and 7 mL of sterile water for injection were extracted and mixed, and then loaded onto an activated C18 column, which was repeated three times till the column loading was completed. The C18 column was rinsed with 10 mL of sterile water for injection twice, and then eluted with 1 mL of ethanol solution. The eluate was collected in a product bottle and sent for sample detection. As shown in FIG. 25, the results of HPLC indicated that $^{18}F$-NYM005 radioactive compound had a radiochemical purity of greater than 95%.

Example 5: 68Ga-NYM005 Radioactive Autoradiography Experiment

Figure 4:
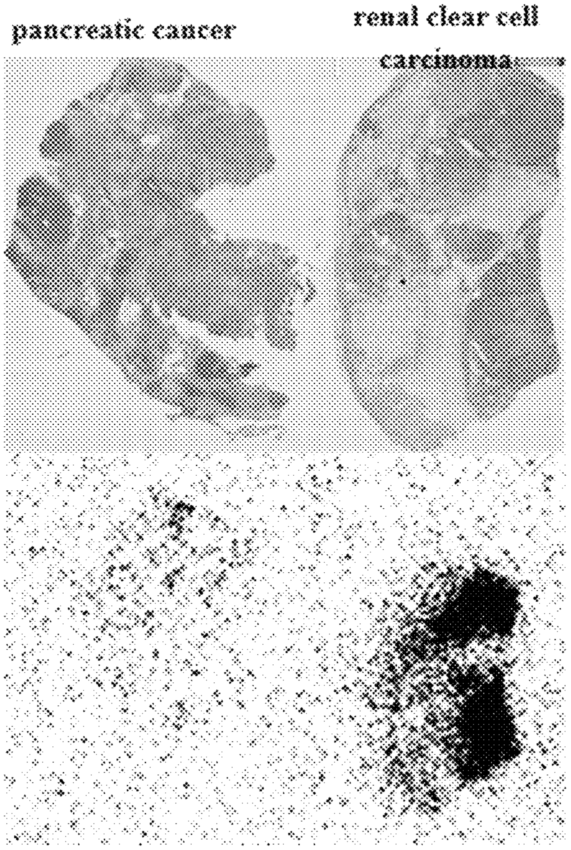
FIG. 4 is a pathological section image according to an embodiment of the present disclosure, wherein the upper image being an image of HE pathological section lesion, and the lower image being an image of the section using autoradioimaging.

Paraffin sections of pancreatic cancer and renal clear cell carcinoma were baked, dewaxed, and hydrated. $^{68}Ga$-NYM005 medicament was prepared to a required concentration. Each section was incubated with radioactive medicament $^{68}Ga$-NYM005 at a volume ranging from 0.3 ml to 0.4 ml for 35 minutes at room temperature. After the incubation was completed, the sections were subjected elution and drying, and then imaged on a phosphor screen. The imaging results of pancreatic cancer sections were shown in FIG. 4, which indicates no obvious radioactive accumulation. The imaging results of renal cell carcinoma sections indicated high radioactive accumulation and were consistent with lesion site in the HE pathological section.

Figure 5:
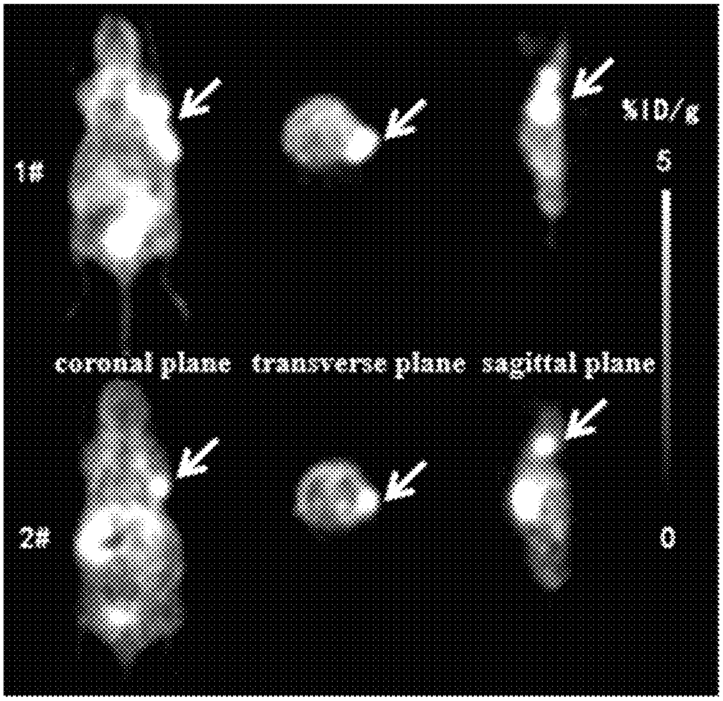
FIG. 5 is an image of Positron Emission Tomography/Computed Tomography (PET/CT) imaging results of $^{68}$Ga-NYM005 medicament in a tumor-bearing 786-O mouse model according to an embodiment of the present disclosure, arrows indicating positions of tumors.

Example 6: Imaging Results of $^{68}Ga$-NYM005 Medicament in Tumor-Bearing 786-O Mouse Model The experimental 786-O animal model was provided by Hengjia Biotechnology (Suzhou) Co., Ltd. The model was a 786-O tumor subcutaneous heterotopic transplant tumor model established based on BALB/c nude mice. This model was a mouse model constructed for human renal clear cell adenocarcinoma cells. Two animal models were randomly selected, and each was administrated with 100 μCi of the above-mentioned $^{68}Ga$-NYM005 medicament. After pre-anesthesia with an appropriate concentration of isoflurane/oxygen mixed gas prior to the scanning, the animals were placed on a Inveon small animal PET/CT scanning bed (Siemens) and continuously anesthetized with isoflurane/oxygen mixed gas. 10-min PET scan was performed 1 hour after the administration. The scanned images were obtained after automatic data reconstruction by means of the device software, and the scanned images were analyzed using PMOD software. As shown in FIG. 5 (in which the arrow indicates the tumor), through analysis of the scanning data, $^{68}$Ga-NYM005 medicament was highly enriched at the tumor site, indicating that the medicament had good tumor targeting performance, and that the medicament not taken by the tumor was quickly excreted from the body through the kidney-bladder.

Figure 6:
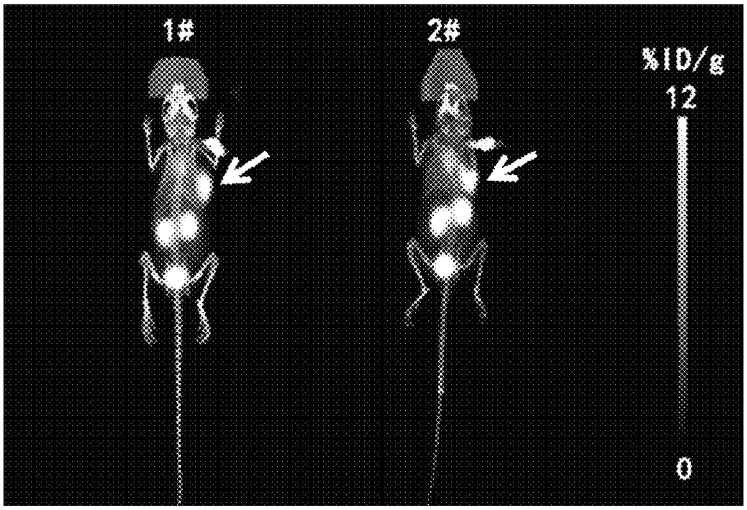
FIG. 6 is an image of PET/CT imaging results of $^{68}$Ga-NYM005 medicament in a tumor-bearing OS-RC-2 mouse model according to an embodiment of the present disclosure, arrows indicating positions of tumors.

Example 7: Imaging Results of $^{68}$Ga-NYM005 Medicament in Tumor-Bearing OS-RC-2 Mouse Model The experimental OS-RC-2 animal model was provided by Hengjia Biotechnology (Suzhou) Co., Ltd. The model was an OS-RC-2 tumor subcutaneous heterotopic transplant tumor model established based on BALB/c nude mice. This model was a mouse model constructed for human renal cancer cells. Two animal models were randomly selected, and each was administrated with 100 μCi of the above-mentioned $^{68}$Ga-NYM005 medicament. After pre-anesthesia with an appropriate concentration of isoflurane/oxygen mixed gas prior to scanning, the animals were placed in a MicroPET/CT imaging cabin (SNPC-303 SuperNova, Pingsheng Medical Technology (Kunshan) Co., Ltd.), and anesthesia was maintained with isoflurane/air mixed gas. A MicroPET/CT scan was performed 1 hour after the administration of the medicament. The scanned images were obtained after reconstruction by means of the device software, and the scanned images were analyzed using PMOD software. As shown in FIG. 6 (in which the arrow indicates the tumor), the $^{68}$Ga-NYM005 medicament was highly enriched at the tumor site, indicating that the medicament had good tumor targeting, and that the medicament not taken by the tumor was quickly excreted from the body through the kidney-bladder.

Figure 7:
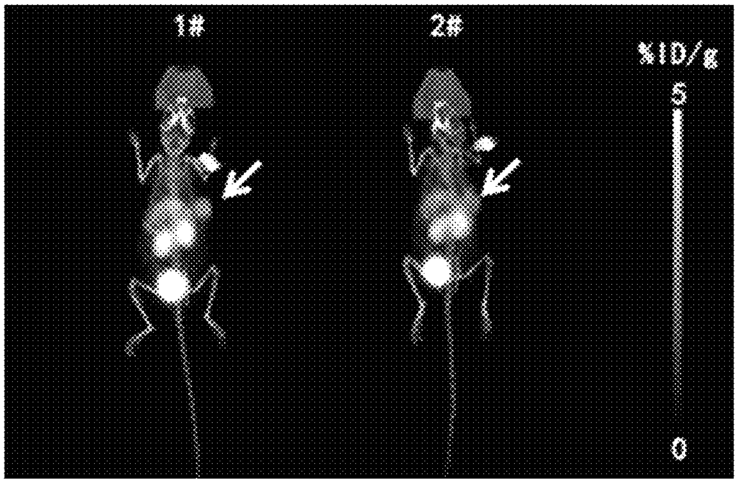
FIG. 7 is an image of PET/CT imaging results of tissue distribution and targeted imaging of $^{68}$Ga-NYM005 medicament in a tumor-bearing 786-O mouse model according to an embodiment of the present disclosure, arrows indicating positions of tumors.

Example 8: PET/CT Scanning Tissue Distribution and Targeting Experiment of $^{68}$Ga-NYM005 Medicament in Tumor-Bearing 786-O Mouse Model The experimental 786-O animal model was provided by Biaodu Baiao Biotechnology (Shanghai) Co., Ltd. The model was a 786-O tumor subcutaneous heterotopic transplant tumor model established based on NOD-SCID mice. This model was a mouse model constructed for human renal clear cell adenocarcinoma cells. Two animal models were randomly selected, and each was administrated with 100 μCi of the above-mentioned $^{68}$Ga-NYM005 medicament. After pre-anesthesia with an appropriate concentration of isoflurane/oxygen mixed gas prior to scanning, the animals were placed in a MicroPET/CT imaging cabin (SNPC-303 SuperNova, Pingsheng Medical Technology (Kunshan) Co., Ltd.), and anesthesia was maintained with isoflurane/air mixed gas. A MicroPET/CT scan was performed 1 hour after the administration of the medicament. The scanned images were obtained after reconstruction by means of the device software, and the scanned images were analyzed using PMOD software. As shown in FIG. 7 (in which the arrow indicates the tumor), biodistribution of $^{68}$Ga-NYM005 medicament in 786-O tumor model mice indicates that the medicament was excreted from the body mainly through the kidney-bladder, and that the medicament had high radioactive concentration in the tumor tissue and low uptake in other tissues.

Figure 8:
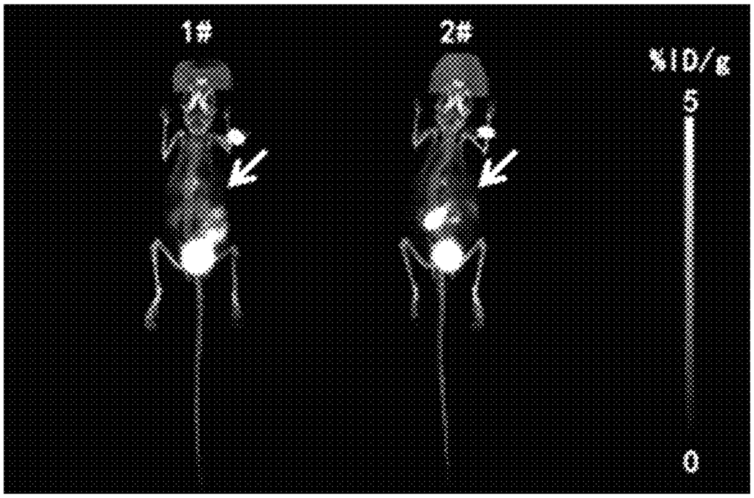
FIG. 8 is an image of competitive inhibition results of $^{68}$Ga-NYM005 medicament in a tumor-bearing 786-0 mouse model according to an embodiment of the present disclosure, arrows indicating positions of tumors.

Example 9: Competitive Inhibition Assay of $^{68}$Ga-NYM005 Medicament in 786-O Mouse Model The experimental 786-O animal model was provided by Biaodu Baiao Biotechnology (Shanghai) Co., Ltd. The model was a 786-O tumor subcutaneous heterotopic transplant tumor model established based on NOD-SCID mice. This model was a mouse model constructed for human renal clear cell adenocarcinoma cells. Two animal models were randomly selected and injected with cold medicament NYM0005 through tail vein. The injection dose was 40 times the mass of the injected hot medicament ($^{68}$Ga-NYM0005). The order of administration was as follow: injecting the hot medicament $^{68}$Ga-NYM0005 30 minutes after the administration of the cold medicament. After pre-anesthesia with an appropriate concentration of isoflurane/oxygen mixed gas prior to scanning, the animals were placed in a MicroPET/CT imaging cabin (SNPC-303 SuperNova, Pingsheng Medical Technology (Kunshan) Co., Ltd.), and anesthesia was maintained with isoflurane/air mixed gas. A MicroPET/CT scan was performed 1 hour after the administration of the hot medicament. The scanned images were obtained after reconstruction by means of the device software, and the scanned images were analyzed using PMOD software. As shown in FIG. 8 (in which the arrow indicates the tumor), the addition of the cold medicament can significantly block the $^{68}$Ga-NYM005 uptake of the tumor, demonstrating that the $^{68}$Ga-NYM005 uptake of the tumor was specific targeted uptake.

Figure 9:
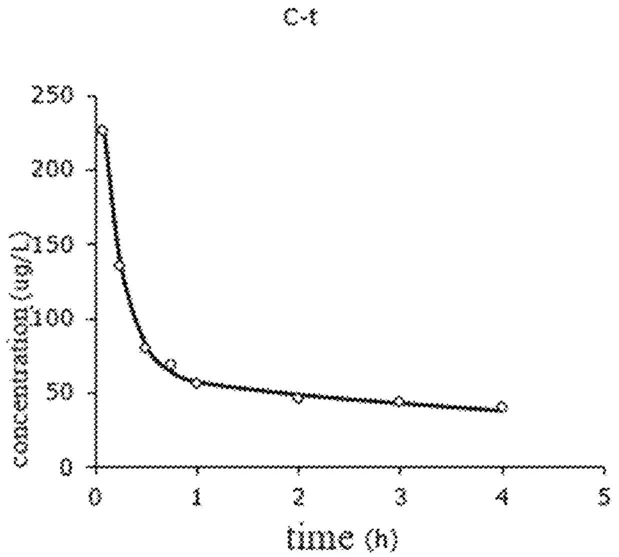
FIG. 9 is a plasma concentration-time profile in mice according to an embodiment of the present disclosure.

Example 10: Tissue Distribution Experiment and Pharmacokinetic Experiment of ICR Mouse Female ICR mice aged 4 to 6 weeks were purchased from Hengjia Biotechnology (Suzhou) Co., Ltd. Four ICR mice were randomly selected therefrom, and each was administrated with 50 Ci of the $^{68}$Ga-NYM005 medicament. Submandibular blood was collected at 5 min, 15 min, 30 min, 45 min, 60 min, 2 h, 3 h, and 4 h after the administration for measuring Gamma counts. The plasma concentrations at different time points were calculated, and then pharmacogenetic parameters of non-compartmental model were calculated using pharmacokinetic counting software DAS (see Table 2). The results were shown in FIG. 9. The pharmacokinetic calculation results demonstrate a good pharmacokinetic activity with an elimination half-life t1/2z=5.81 h, a peak time Tmax of about 0.0833 h, and a peak concentration Cmax of about 225.6 μg/L.

TABLE 2

Pharmacogenetic parameters of non-compartmental model calculated based on pharmacokinetic counting software DAS

| Statistical moment parameters | Unit | Value of parameters |
|---|---|---|
| AUC(0-t) | ug/L*h | 250.408 |
| AUC(0-∞) | ug/L*h | 581.348 |
| AUMC(0-t) | | 372.384 |
| AUMC(0-∞) | | 4470.84 |
| MRT(0-t) | h | 1.487 |

TABLE 2-continued

| Pharmacogenetic parameters of non-compartmental model calculated based on pharmacokinetic counting software DAS | | |
|---|---|---|
| Statistical moment parameters | Unit | Value of parameters |
| MRT(0-∞) | h | 7.69 |
| VRT(0-t) | h^2 | 1.593 |
| VRT(0-∞) | h^2 | 69.821 |
| Zeta | 1/h | 0.119 |
| Zeta regression tail spot | | 124 |
| Cz (tail spot regression value) | ug/L | 39.471 |
| t½z | h | 5.81 |
| Tmax | h | 0.0833333 |
| Vz | L/kg | 0.588 |
| CLz | L/h/kg | 0.07 |
| Cmax | ug/L | 225.6085 |

Figure 10:
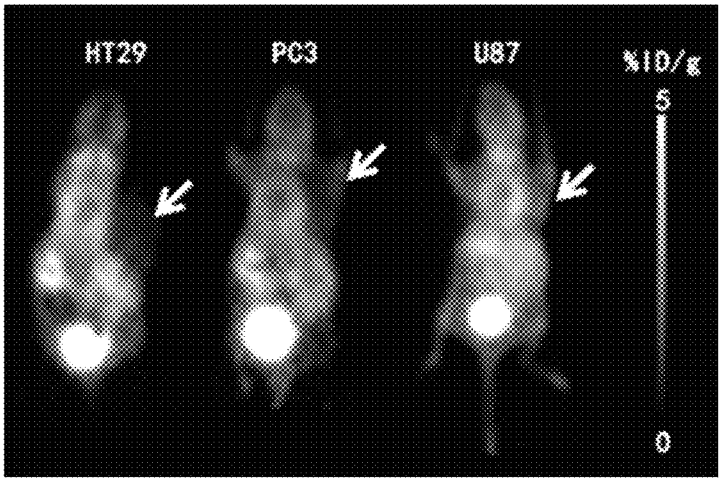
FIG. 10 is an image of PET/CT imaging results of $^{68}$Ga-NYM005 in tumor-bearing HT29, PC3, and U87 mouse models according to an embodiment of the present disclosure, wherein arrows indicating positions of tumors.

Example 11: PET Scanning Tissue Distribution and Targeting Experiment of $^{68}$Ga-NYM005 in HT29, PC3, and U87 Models The experimental HT29, PC3, and U87 animal models were provided by Hengjia Biotechnology (Suzhou) Co., Ltd. The models were HT29, PC3, and U87 tumor subcutaneous heterotopic transplant tumor models established based on BALB/c nude mice. These models were mouse models constructed for human colon cancer cells, human prostate cancer cells, and human brain gliomas, respectively. One animal model from each of the above animal models was randomly selected, and each was administrated with 80 μCi of the above-mentioned $^{68}$Ga-NYM005 medicament. After pre-anesthesia with an appropriate concentration of isoflurane/oxygen mixed gas prior to scanning, the animals were placed in a small animal PET/CT scanning cabin (Super Nova, Pingsheng Medical Technology (Kunshan) Co., Ltd.), and anesthesia was maintained with isoflurane/air mixed gas. A MicroPET/CT scan was performed 1 hour after the administration of the medicament. The scanned images were obtained after reconstruction by means of the device software, and the scanned images were analyzed using PMOD software. As shown in FIG. 10 (in which the arrow indicates the tumor), there was no significantly high uptake of $^{68}$Ga-NYM005 medicament at the tumor site, indicating that the $^{68}$Ga-NYM005 medicament has no targeting performance in tumors such as HT29, PC3, and U87.

Figure 11:
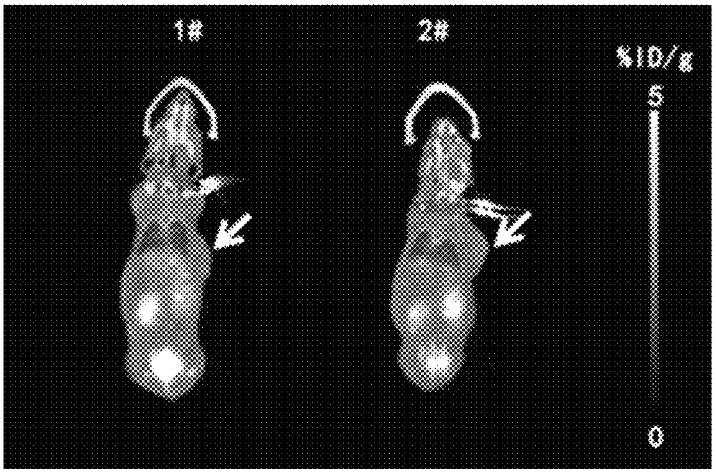
FIG. 11 is an image of PET/CT imaging results of $^{68}$Ga-NYM005 in a tumor-bearing HCT116 mouse model according to an embodiment of the present disclosure, wherein arrows indicating positions of tumors.

Example 12: PET/CT Scanning Tissue Distribution and Targeting Experiment of $^{68}$Ga-NYM005 in HCT116 Model The experimental HCT116 animal model was provided by Hengjia Biotechnology (Suzhou) Co., Ltd. The model was a HCT116 tumor subcutaneous heterotopic transplant tumor model established based on BALB/c nude mice. This model was a mouse model constructed for human colon cancer cells. Two animal models were randomly selected, and each was administrated with 100 μCi of the above-mentioned $^{68}$Ga-NYM005 medicament. After pre-anesthesia with an appropriate concentration of isoflurane/oxygen mixed gas prior to scanning, the animals were placed in a MicroPET/CT imaging cabin (SNPC-303 SuperNova, Pingsheng Medical Technology (Kunshan) Co., Ltd.), and anesthesia was maintained with isoflurane/air mixed gas. A MicroPET/CT scan was performed 1 hour after the administration of the medicament. The scanned images were obtained after reconstruction by means of the device software, and the scanned images were analyzed using PMOD software. As shown in FIG. 11 (in which the arrow indicates the tumor), there was no obvious high uptake of the $^{68}$Ga-NYM005 medicament at the tumor site, indicating that the $^{68}$Ga-NYM005 medicament has no targeting effect in the HCT116 tumor.

Example 13: Safety Evaluation Experiment

Figure 12:
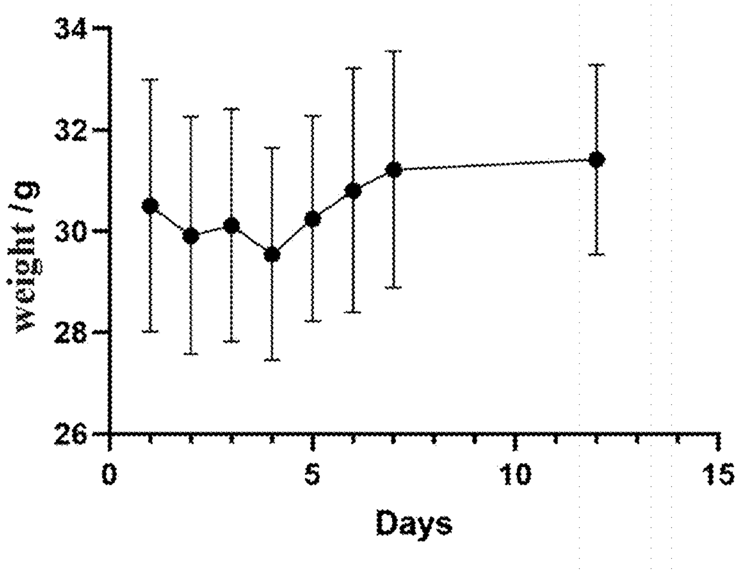
FIG. 12 is a weight change graph of mice according to an embodiment of the present disclosure.

Six ICR mice were selected as experimental animals, supplied by Miracles (Suzhou) Science and Technology Service Co., Ltd. Each animal was administrated with 300 μCi of $^{68}$Ga-NYM005 sterile injection and observed for 7 consecutive days after the administration. The results were shown in FIG. 12, during the 7-day observation, no mice died or had abnormal reactions, and all mice gained weight after the experiment. The $^{68}$Ga-NYM005 molecule has good safety and meet the needs of scientific research and clinical medicament use.

Example 14: Estimation of Radiation Dose for $^{68}$Ga-NYM005 in Human Body

Three ICR mice were taken, each was administrated with 100 μCi of radioactive medicament $^{68}$Ga-NYM005. Thereafter, the mice were subjected to a dynamic scan for 30 minutes, and then a static scan for 10 minutes at time points of 1 h, 2 h, 3 h, and 4 h. The tissue distribution data at different time points in normal mice were obtained according to the scanning data, and further retention time in each organ in the mouse was calculated based on PMOD software. Next, a retention time in human organs was derived from the retention time in each organ in the mouse, and radiation dose in the human body was calculated using OLINDA software. The calculation result was overall effective dose of the human body ED-0.011mSv/MBq. Based on the clinical administration dose of 111 MBq (3mCi)/person, total radiation effective dose was 1.221 mSv/person, which was much lower than that of conventional CT chest and abdomen scans of 10 mSv to 15 mSv, thereby falling within the safe range. Estimation table of the radiation dose is shown in Table 3 below.

TABLE 3

| Calculation of radiation dose in respective tissues and organs of patients in clinical research | | | | | |
|---|---|---|---|---|---|
| Target Organ | Alpha | Beta | Gamma | Total | ICRP-103 ED |
| Adrenals | 0.00E+00 | 1.04E−02 | 6.13E−03 | 1.65E−02 | 1.53E−04 |
| Brain | 0.00E+00 | 1.60E−03 | 2.00E−03 | 3.60E−03 | 3.60E−05 |
| Esophagus | 0.00E+00 | 8.91E−03 | 4.54E−03 | 1.35E−02 | 5.38E−04 |
| Eyes | 0.00E+00 | 8.89E−03 | 3.26E−03 | 1.21E−02 | 0.00E+00 |
| Gallbladder Wall | 0.00E+00 | 9.25E−03 | 6.00E−03 | 1.53E−02 | 1.41E−04 |
| Left colon | 0.00E+00 | 8.90E−03 | 5.80E−03 | 1.47E−02 | 7.13E−04 |
| Small Intestine | 0.00E+00 | 8.89E−03 | 5.93E−03 | 1.48E−02 | 1.37E−04 |

TABLE 3-continued

| Calculation of radiation dose in respective tissues and organs of patients in clinical research | | | | | |
|---|---|---|---|---|---|
| Target Organ | Alpha | Beta | Gamma | Total | ICRP-103 ED |
| Stomach Wall | 0.00E+00 | 1.23E−02 | 5.15E−03 | 1.75E−02 | 2.10E−03 |
| Right colon | 0.00E+00 | 1.15E−02 | 5.61E−03 | 1.71E−02 | 8.31E−04 |
| Rectum | 0.00E+00 | 8.89E−03 | 5.74E−03 | 1.46E−02 | 3.37E−04 |
| Heart Wall | 0.00E+00 | 7.96E−03 | 5.12E−03 | 1.31E−02 | 1.21E−04 |
| Kidneys | 0.00E+00 | 2.36E−02 | 6.65E−03 | 3.03E−02 | 2.79E−04 |
| Liver | 0.00E+00 | 1.02E−02 | 5.30E−03 | 1.55E−02 | 6.19E−04 |
| Lungs | 0.00E+00 | 7.20E−03 | 4.24E−03 | 1.14E−02 | 1.37E−03 |
| Pancreas | 0.00E+00 | 8.89E−03 | 5.87E−03 | 1.48E−02 | 1.36E−04 |
| Prostate | 0.00E+00 | 8.89E−03 | 5.66E−03 | 1.45E−02 | 6.72E−05 |
| Salivary Glands | 0.00E+00 | 8.89E−03 | 4.26E−03 | 1.31E−02 | 1.31E−04 |
| Red Marrow | 0.00E+00 | 6.32E−03 | 4.75E−03 | 1.11E−02 | 1.33E−03 |
| Osteogenic Cells | 0.00E+00 | 5.33E−03 | 5.05E−03 | 1.04E−02 | 1.04E−04 |
| Spleen | 0.00E+00 | 8.97E−03 | 5.26E−03 | 1.42E−02 | 1.31E−04 |
| Testes | 0.00E+00 | 8.89E−03 | 4.30E−03 | 1.32E−02 | 5.27E−04 |
| Thymus | 0.00E+00 | 8.99E−03 | 4.55E−03 | 1.35E−02 | 1.25E−04 |
| Thyroid | 0.00E+00 | 8.89E−03 | 4.55E−03 | 1.34E−02 | 5.38E−04 |
| Urinary Bladder Wall | 0.00E+00 | 8.89E−03 | 5.64E−03 | 1.45E−02 | 5.81E−04 |
| Total Body | 0.00E+00 | 9.48E−03 | 4.29E−03 | 1.38E−02 | 1.10E−02 |

Example 15: Imaging Results of $^{68}$Ga-NYM005 Clinical Research Experiment

Figure 13:
FIG. 13 is an image of clinical PET/CT imaging results of $^{68}$Ga-NYM005 according to an embodiment of the present disclosure.

The currently commonly used early tumor screening tracer $^{18}$F-FDG PEC/CT imaging indicated that the patient had an abnormal mass in right kidney and metastasis to both lungs and mediastinal lymph nodes. A right kidney puncture biopsy was performed, and the pathological examination indicated clear cell carcinoma, WHO/ISUP nuclear grade 2, Vimentin9+, PAX-8+, P504S+, and Ki6710%. After the patient was recommended by a clinician for enrollment and signed the informed consent form, the patient was administrated with 5 mCi of $^{68}$Ga-NYM005 sterile injection via dorsal vein of a hand, and then waited for 1 hour to perform a PET/CT scan. The imaging results were shown in FIG. 13.

Analysis of examination results: a soft tissue density mass in the right kidney was observed, approximately 9.2 cm in size, with abnormally increased radioactive uptake, SUVmax 14.6. A strip-shaped focus of increased radioactive uptake was observed in the inferior vena cava, which was approximately 4.7 cm long and had a SUVmax of 12.7. Increased radioactive uptake was observed in some pulmonary vessels, with a SUVmax of 3.4. Multiple lymph nodes with increased radioactive uptake were observed in the left retroperitoneum, left hilum, main pulmonary artery window, and left supraclavicular region. The largest one was about 1.8 cm in size, with a SUVmax of 12.5. Multiple soft tissue density nodules were seen in the lungs, the largest of which was approximately 2.5 cm in size, with increased radioactive uptake and SUVmax of 11.6. A focus of increased radioactive uptake was observed in the left femoral head, approximately 1.4 cm in size, with SUVmax of 11.1.

Conclusion of clinical diagnosis: the lesion with high expression of $^{68}$Ga-NYM005 in the right kidney may be consistent with the manifestation of renal clear cell carcinoma, accompanied by multiple lymph node metastases in the left retroperitoneum, left hilum, aortopulmonary window, and left supraclavicular lymph nodes, multiple metastases in the lungs, metastasis to the left femoral head, and tumor thrombosis in the inferior vena cava and pulmonary artery.

Through this clinical verification, the $^{68}$Ga-NYM005 molecule can detect more tumor metastases in the clinical application of renal cancer diagnosis than the currently commonly used $^{18}$F-FDG tracer, thereby having higher clinical application value.

Example 16: Preparation Process of NYM034 Molecule

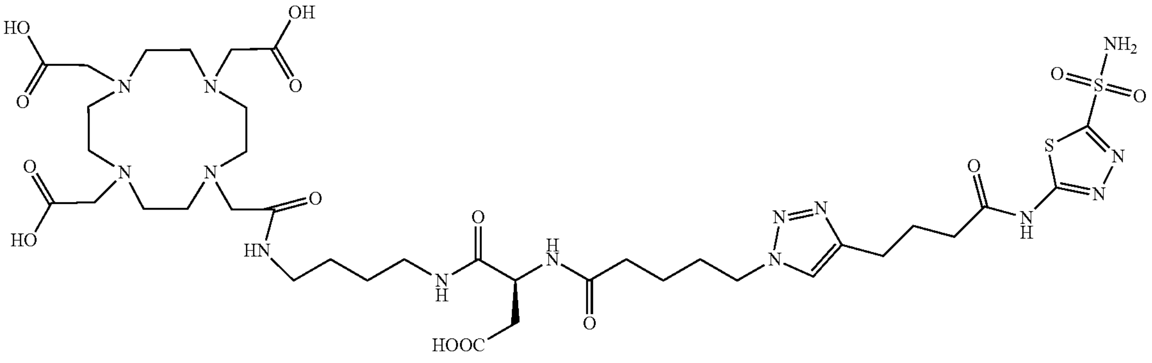

Structure formula of NYM034

Figure 14:
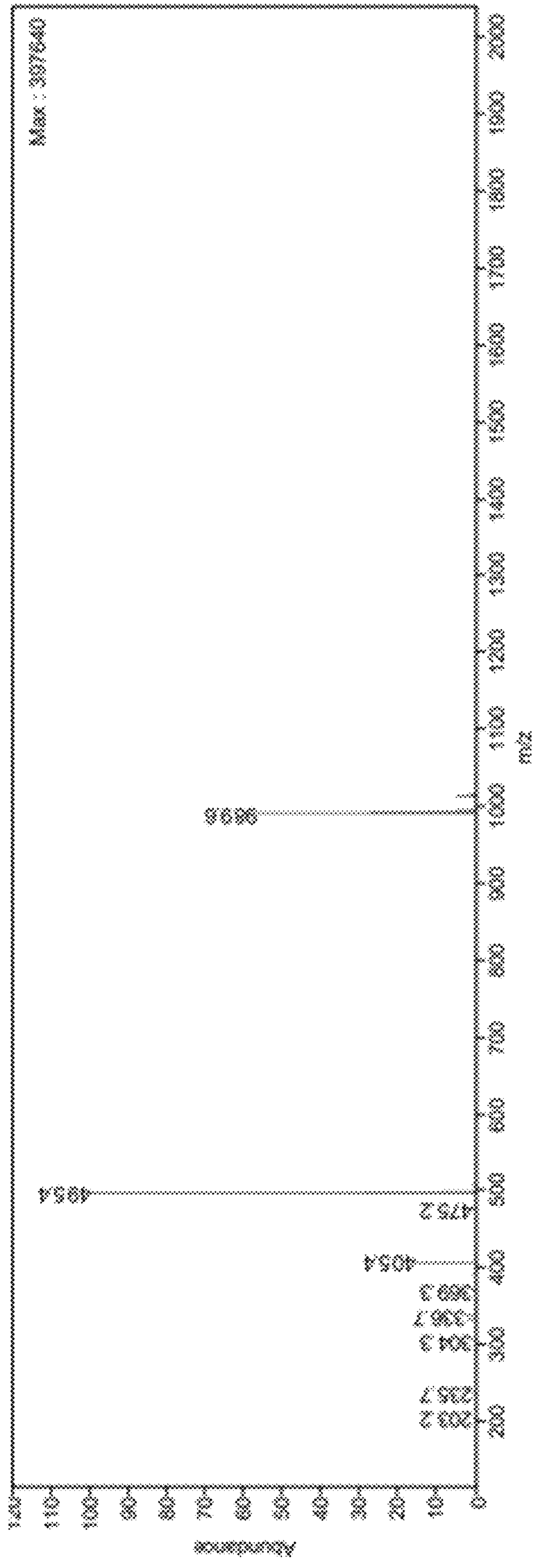
FIG. 14 is an LC-MS spectrum of NYM034 molecule according to an embodiment of the present disclosure.
Figure 15:
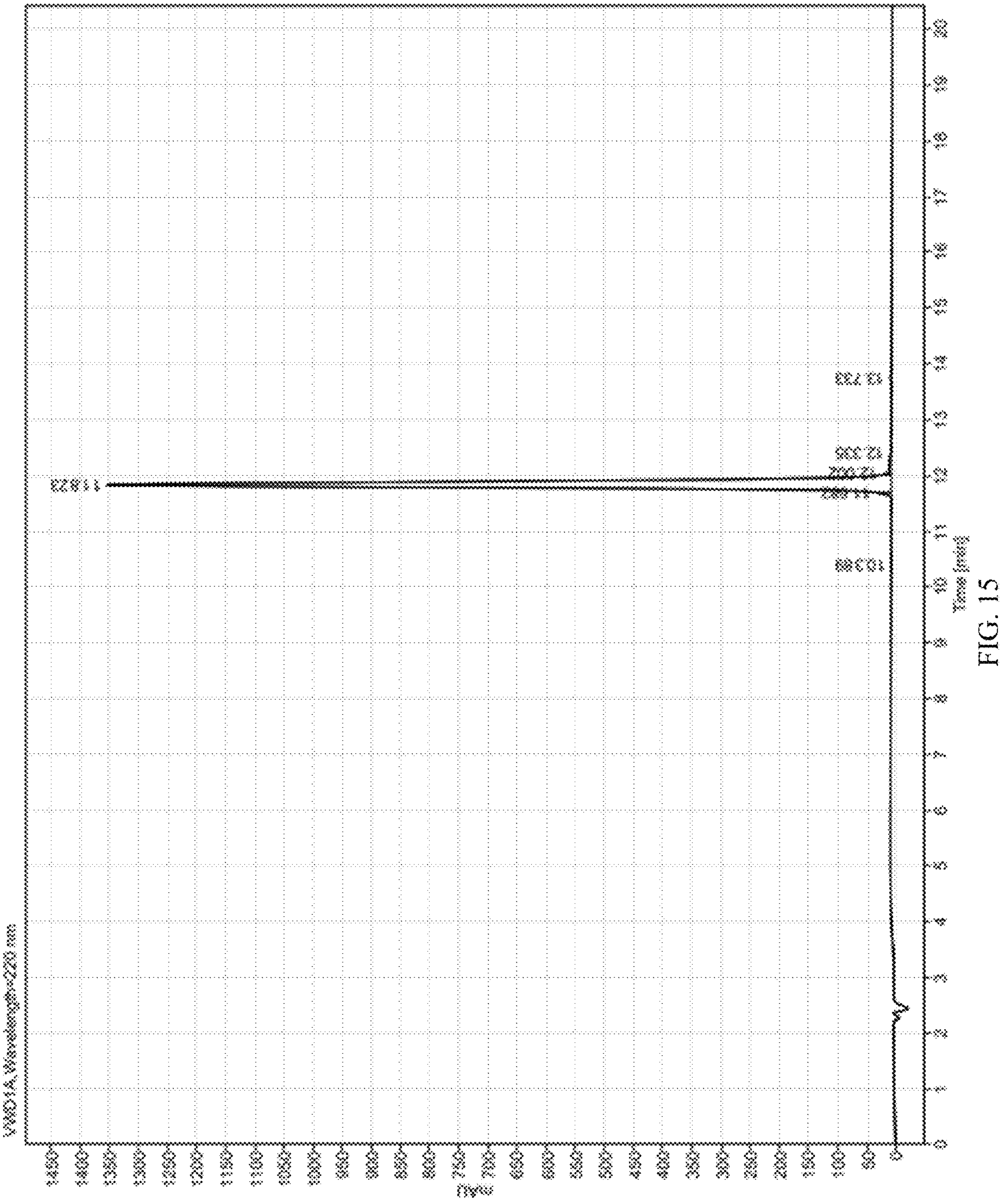
FIG. 15 is an HPLC diagram of NYM034 according to an embodiment of the present disclosure.

LC-MS spectrum of NYM034 molecule can refer to FIG. 14, and HPLC spectrum of NYM034 molecule can refer to FIG. 15.

Synthetic Scheme:

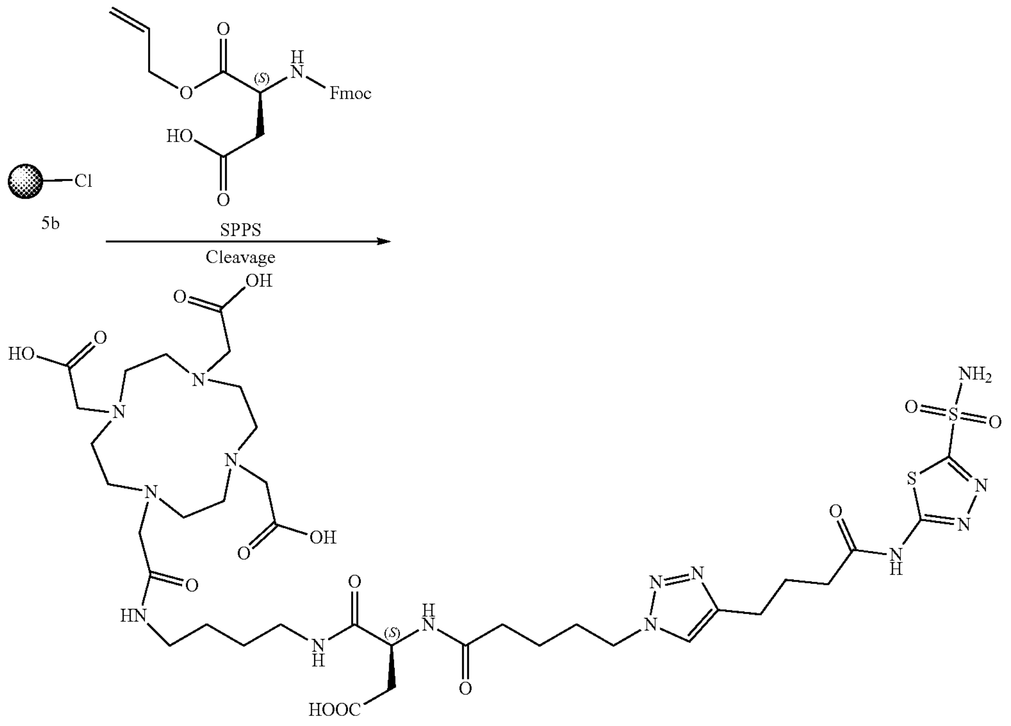

NYM034

Synthesis of polypeptide: polypeptide was synthesized using a Fmoc synthesis method.

1. Preparation of resin: 10.0 mL of DCM solution containing Fmoc-Asp-OAll (500 μmol, 1.00 eq) and DIEA (2.00 mmol, 4.00 eq) was added to 2-CTC resin (500 μmol, 1.00 eq), and the mixture was purged with nitrogen at 20° C. and stirred for 2 hours for reaction. MeOH (500 μL) was added, and the mixture was further stirred for 30.0 minutes. The resin was then washed with DMF for five times, using 20.0 mL of DMF each time (20.0 mL*5).

2. Deprotection: DMF solution (20.0 mL) containing 20% (v/v) piperidine was added to the resin, and the mixture was stirred for 30.0 minutes under nitrogen purge. The resin was washed and filtered with DMF for five times, using 20.0 mL of DMF each time (20.0 mL*5).

3. Coupling: 5-azidopentanoic acid (1.50 mmol, 3.00 eq) was added into DMF solvent (20.0 mL), and HATU (1.50 mmol, 3.00 eq) and DIEA (3.00 mmol, 6.00 eq) were added. The mixture was added into the resin and stirred for 30 minutes at 20° C. under nitrogen purge. The resin was washed with DMF for five times, using 20.0 mL of DMF each time (20.0 mL*5).

4. The above steps 2 to 3 were repeated to couple amino acids in Table 4 in sequence.

TABLE 4

| Amino acid to be fed | Coupling reagent |
|---|---|
| Compound 3b (1.50 eq) | CuI (0.50 eq), DIEA (2.00 eq) |
| N-Fmoc-1,4-diaminobutane HCL (3.00 eq) | HOAt (3.00 eq), DIC (3.00 eq) |
| DOTA-$(COOt\text{-}Bu)_3$ (1.50 eq) | HOAt (1.50 eq), DIC (1.50 eq) |

5. The resin was washed with DMF for five times, using 20.0 mL of DMF each time (20.0 mL*5), and filtered to obtain the polypeptide resin (5b).

6. Cleavage and purification of the polypeptide:

The resin from the previous step was washed with MeOH for three times, using 20.0 mL of MeOH each time (20.0 mL*3), and dried under vacuum to obtain the polypeptide resin (5b).

Polypeptide with side chain protecting groups was added into a flask, and 20 mL of lysis buffer (92.5% TFA/2.5% TIS/2.5% $H_2O$/2.5% MPR) was added. The mixture was stirred at 20° C. for 2 hours for deprotection, precipitated with tert-butyl methyl ether (50.0 mL), and centrifuged (3.00 min, 3000 rpm). The precipitate was washed twice with tert-butyl methyl ether (50.0 ml).

The obtained crude polypeptide was dried under vacuum for 2 hours to obtain 400 mg of crude product.

The crude product was purified by preparative HPLC (TFA conditions: A: 0.075% TFA in $H_2O$ solution, B: ACN) to obtain the target product NYM034 (62.0 mg, 55.3 μmol, yield 11.1%, purity 98.45%, TFA) as a white solid.

Example 17: Preparation Process of $^{68}$Ga-NYM034

The synthesized NYM034 precursor was subjected to a chelation reaction with radioactive nuclide gallium [$^{68}$Ga] to further obtain a $^{68}$Ga-NYM034 tracer approved for clinical PET/CT tracing. The labeling technology was mature, and a radiochemical purity of the labeled product radioactive compound may usually reach 99%.

The labeling process was shown below. The entire labeling process can be completed within 20 minutes, and yield of the radioactive compound can reach 70%.

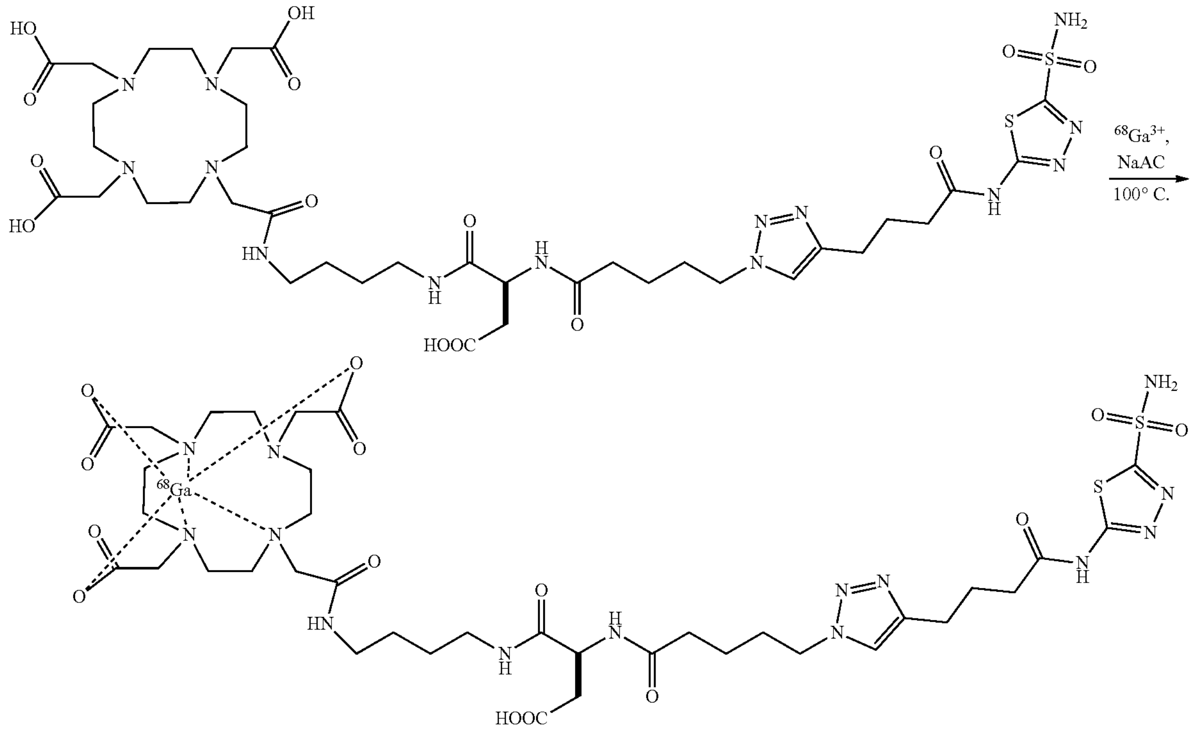

$^{68}$Ga nuclide was obtained by eluting a germanium gallium generator with a 0.05M hydrochloric acid solution. 1 mL of the $^{68}$Ga nuclide (20 mCi) solution was added to a reaction bottle, then 1 mL of 0.3 mol/L acetic acid/sodium acetate buffer solution was added to the reaction bottle, allowing a volume ratio of $^{68}$Ga nuclide to the buffer solution was 1:1, and pH value was adjusted to 4.0. An appropriate amount of NYM034 precursor compound was taken and added to sterilized water for injection to prepare a 1 mg/mL precursor solution. Then, 45 nmol (44.5 μg) of the precursor solution was taken and added to the reaction bottle, and the mixture reacted for 6 minutes at 105° C. After the reaction was completed, the reaction mixture was cooled for 1 minute. 5 mL of sterilized water for injection was taken using a 10 mL sterile syringe and added to the reaction bottle to dilute the reaction solution while lowering the temperature of the reaction solution. Then, all the liquid in the reaction bottle was sucked into the syringe. Pre-activated Sep-Pak C-18 column was taken and connected to an outlet of the syringe. The reaction dilution was pushed to flow through the Sep-Pak C-18 column, and the target product $^{68}$Ga-NYM034 was adsorbed by the C-18 column. Then, the C-18 column was eluted with 1 mL of 70% medical grade anhydrous ethanol solution, and the eluted solution was filtered through a 0.22 μm sterile filter membrane and flowed into a sterile vacuum bottle. Then, 4 mL of physiological saline solution was added to obtain a $^{68}$Ga-NYM034 sterile injection solution.

Figure 16:
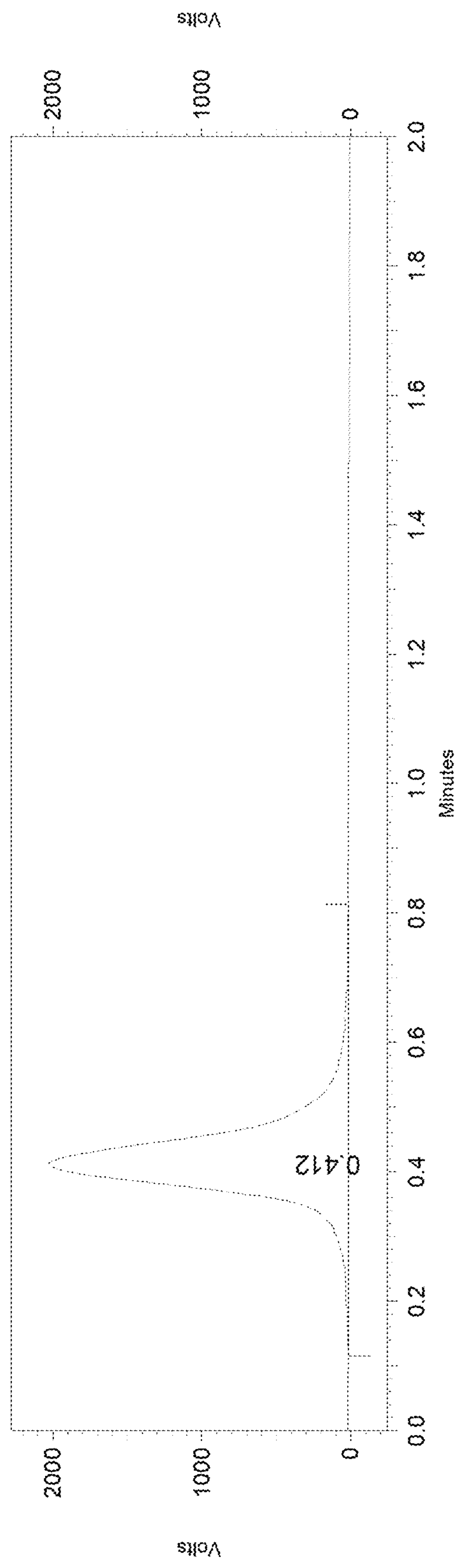
FIG. 16 is a graph of results of radioactive thin layer chromatography scanning purity analysis of $^{68}$Ga-NYM034 according to an embodiment of the present disclosure.

Radioactive thin layer chromatography was used for quality control of the above products, using a carrier of glass fiber paper and a developing agent of 0.5 M citric acid/sodium citrate buffer (pH=5). The glass fiber paper was taken and the sample was transferred using a pipette and tapped gently on the glass fiber paper at a position 1.5 cm from the bottom. Then, the glass fiber paper was put into a tube with 500 μL of 0.5 M citric acid/sodium citrate buffer (pH=5) added in advance, expanded to a position 2.5 cm from the top of the chromatography paper, and the paper was taken out and dried, and detected with a Radio-TLC thin layer scanner. In 0.5 M citric acid/sodium citrate buffer (pH=5) system, Rf value of the product ranges from 0.3 to 0.6. As shown in FIG. 16, according to the results of radioactive thin layer chromatography scanning purity analysis of the $^{68}$Ga-NYM034 molecule, the radioactive compound had a radiochemical purity of 100%.

Figure 17:
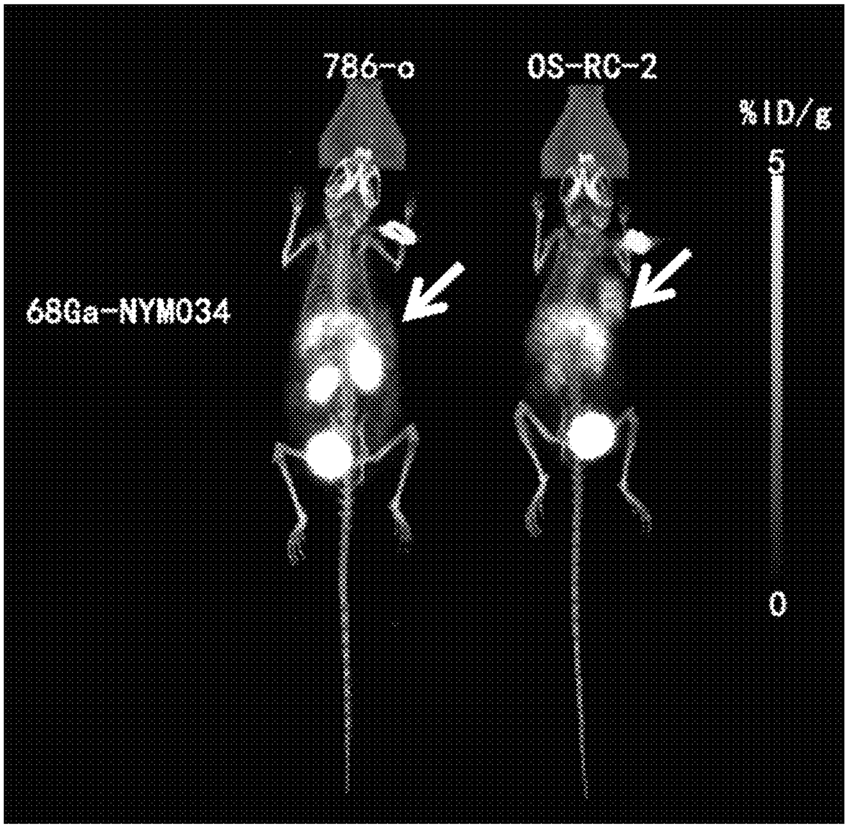
FIG. 17 is an image of PET/CT imaging results of $^{68}$Ga-NYM034 in tumor-bearing 786-O and OS-RC-2 mouse models according to an embodiment of the present disclosure, arrows indicating positions of tumors.

Example 18: PET Scanning Tissue Distribution and Targeting Experiment of $^{68}$Ga-NYM034 in 786-O and OS-RC-2 Model The experimental 786-O animal model was provided by Hengjia Biotechnology (Suzhou) Co., Ltd. The model was a 786-O tumor subcutaneous heterotopic transplant tumor model established based on BALB/c nude mice. This model was a mouse model constructed for human renal clear cell adenocarcinoma cells. The experimental OS-RC-2 animal model was provided by Hengjia Biotechnology (Suzhou) Co., Ltd. The model was an OS-RC-2 tumor subcutaneous heterotopic transplant tumor model established based on BALB/c nude mice. This model was a mouse model constructed for human renal cancer cells. One animal from each of the two animal models was selected, and each was administrated with 100 μCi of the above-mentioned $^{68}$Ga-NYM034 medicament. After pre-anesthesia with an appropriate concentration of isoflurane/oxygen mixed gas prior to scanning, the animals were placed in a MicroPET/CT imaging cabin (SNPC-303 Super Nova, Pingsheng Medical Technology (Kunshan) Co., Ltd.), and anesthesia was maintained with isoflurane/air mixed gas. A MicroPET/CT scan was performed 1 hour after the administration of the medicament. The scanned images were obtained after reconstruction by means of the device software, and the scanned images were analyzed using PMOD software. As shown in FIG. 17 (in which the arrow indicates the tumor), the $^{68}$Ga-NYM034 medicament was highly enriched in the tumor site of the OS-RC-2 model, while the medicament was less absorbed by the tumor in the 786-0 model, indicating that the medicament had good tumor targeting effect in the OS-RC-2 model.

Example 19: Preparation Process of NYM035 Molecule

NYM035

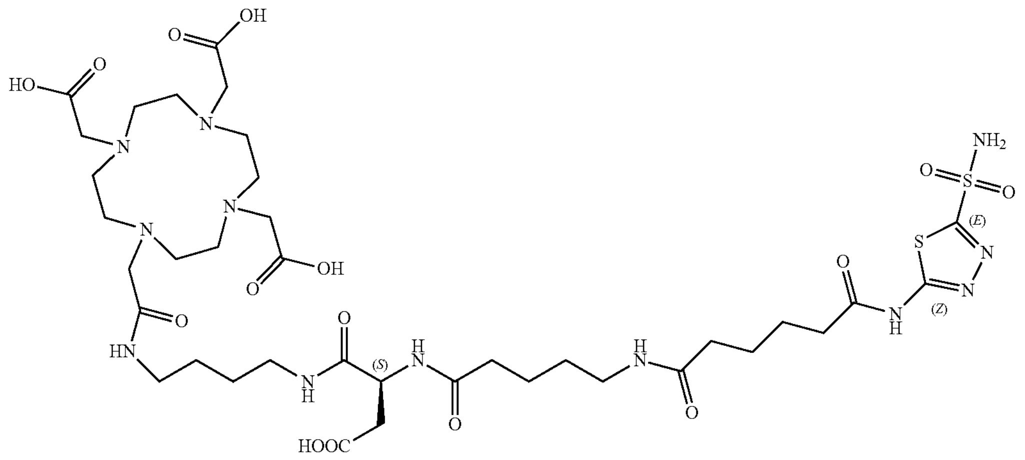

Structure formula of NYM035

Figure 18:
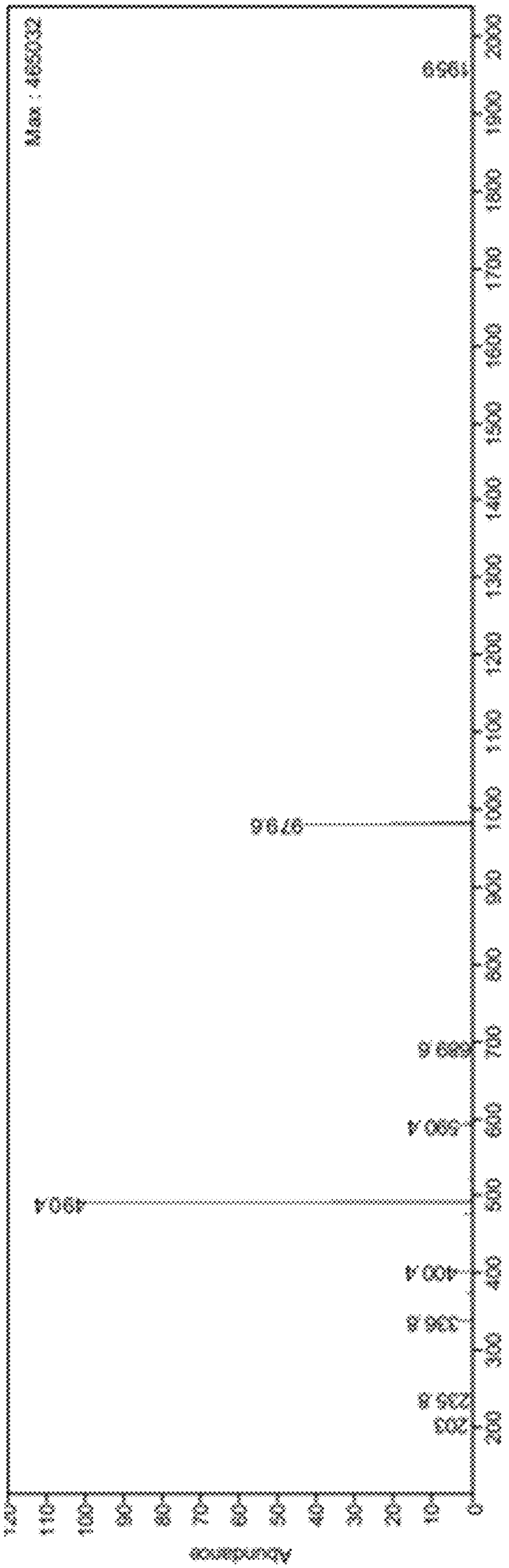
FIG. 18 is an LC-MS spectrum of NYM035 according to an embodiment of the present disclosure.
Figure 19:
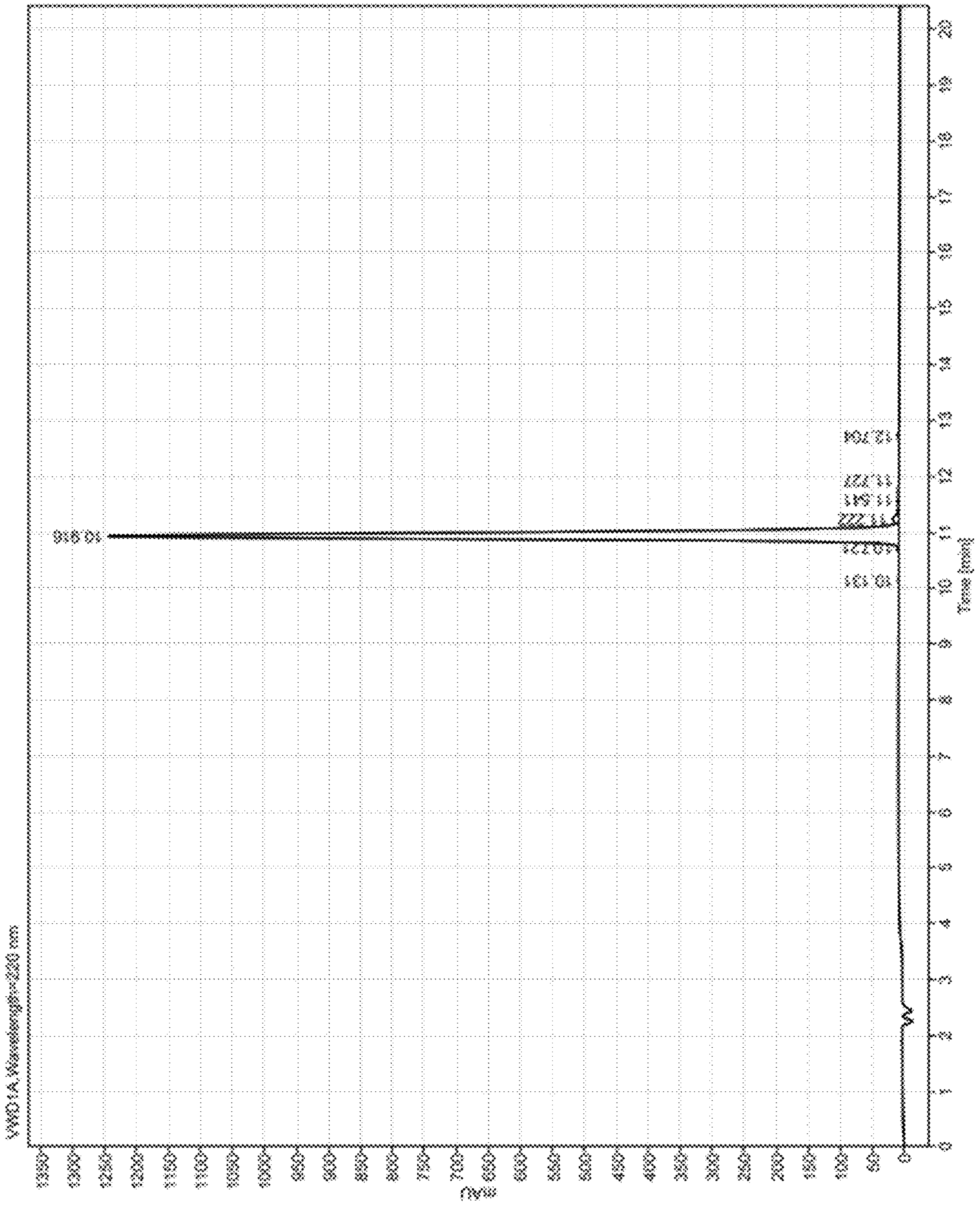
FIG. 19 is an HPLC diagram of NYM035 according to an embodiment of the present disclosure.

LC-MS spectrum of NYM035 molecule can refer to FIG. 18, and HPLC spectrum of NYM035 molecule can refer to FIG. 19.

Synthetic Scheme:

Step 1:

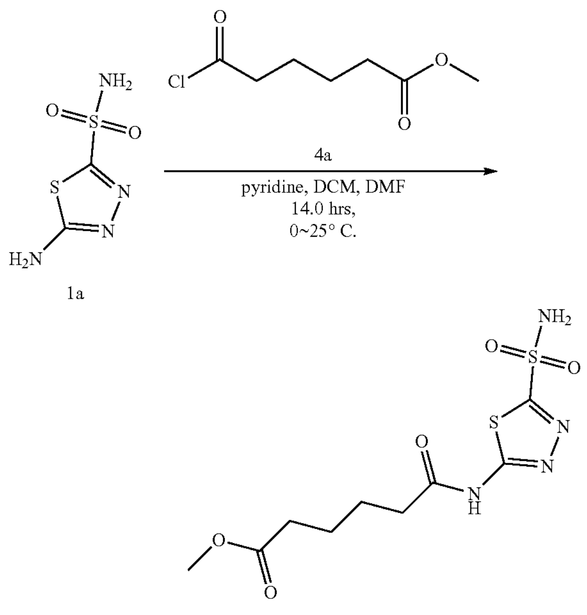

2a

Compound (1a) (3.00 g, 16.7 mmol, 1.00 eq) and pyridine (2.63 g, 33.3 mmol, 2.69 mL, 2.00 eq) were dissolved in 30.0 mL of DMF solvent, and the solution was cooled to 0° C.

Compound (4a) (2.97 g, 16.65 mmol, 1.00 eq) was dissolved in 20.0 mL of DMF solvent, this solution was added dropwise to the above solution, and the mixture was stirred at 25° C. for 14.0 hours. The reaction solution was concentrated under reduced pressure to remove the solvent. The residue was diluted with 45.0 mL of water and 45.0 mL of saturated $NaHCO_3$, and filtered to obtain compound (2a) (5.00 g, 15.0 mmol) as a white solid.

Step 2:

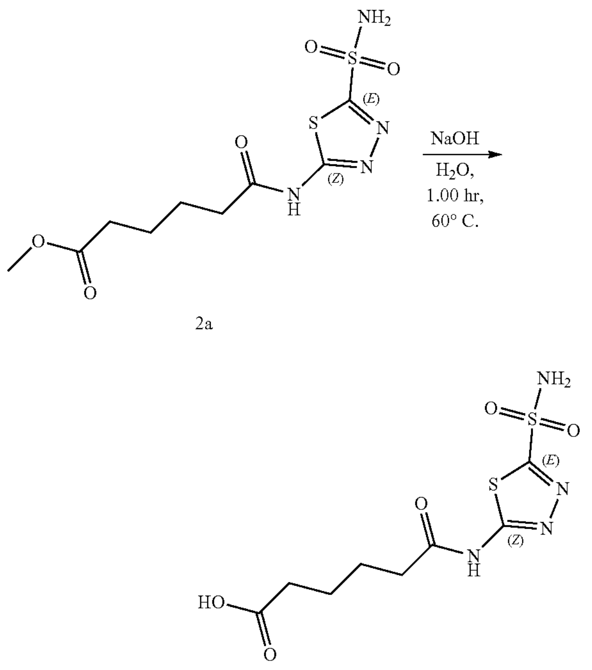

3a

Compound (2a) (5.00 g, 15.0 mmol, 1.00 eq) and NaOH (3.45 g, 86.3 mmol, 5.76 eq) were dissolved in 70.0 mL of water, and the mixture was stirred and heated for 1 hour until the temperature was 60° C. After the reaction solution was cooled, pH was adjusted to 4 with 1 mol/L HCl solution. The obtained solid was filtered and washed with water to obtain compound (3a) (2.00 g, 6.22 mmol) as a white solid.

Step 3:

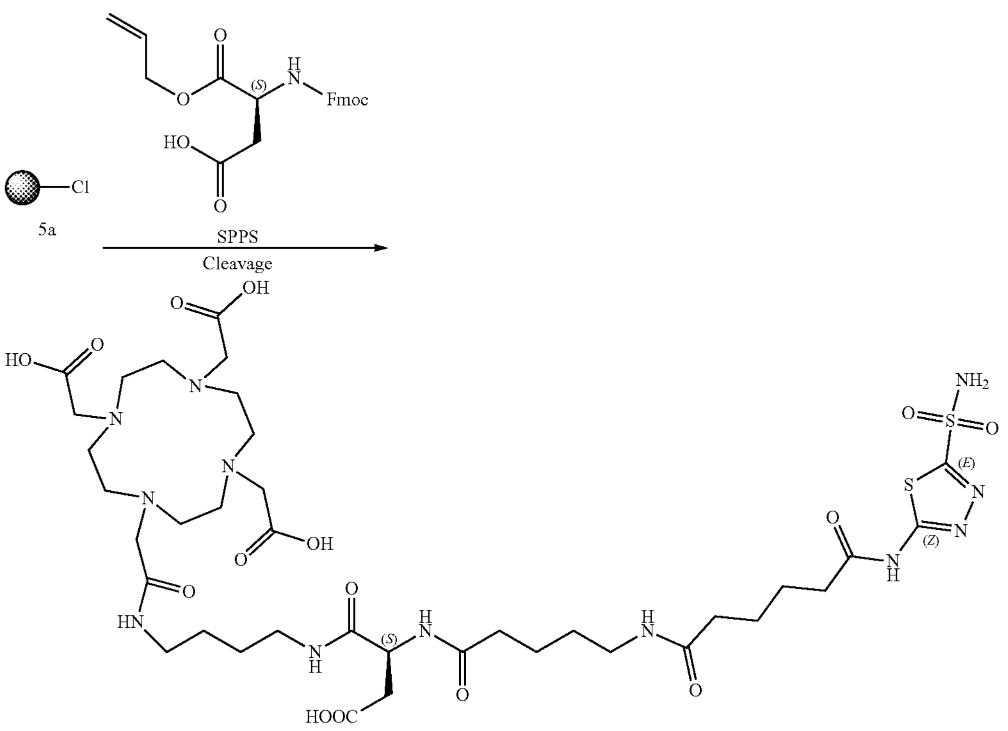

5a

NYM035

Synthesis of polypeptide: polypeptide was synthesized using a Fmoc synthesis method.

1. Preparation of resin: Fmoc-Asp-Alloc (500 μmol, 1.00 eq) and DIEA (2.00 mmol, 4.00 eq) were dissolved in 10.0 mL of DCM solvent, and the mixed solution was added to 2-CTC resin. The mixture was purged with nitrogen at 20° C. and stirred for 2 hours for reaction. Then, MeOH (500 μL) was added and the mixture was stirred for 30.0 minutes. The resin was then washed with DMF for five times, using 20.0 mL of DMF each time (20.0 mL*5).

2. Deprotection: DMF solution (20.0 mL) containing 20% piperidine was added to the resin, and the mixture was stirred for 30.0 minutes under nitrogen purge. The resin was washed and filtered with DMF for five times, using 20.0 mL of DMF each time (20.0 mL*5).

3. Coupling: Fmoc-5-Ava-OH (0.75 mmol, 1.50 eq) was dissolved in 20.0 mL of DMF solvent, and HOAt (0.75 mmol, 1.50 eq) and DIC(0.75 mmol, 1.50 eq) were added. The mixture was added to the resin and stirred for 2 hours at 20° C. under nitrogen purge. The resin was washed with DMF for five times, using 20.0 mL of DMF each time (20.0 mL*5).

4. The above steps 2 to 3 were repeated to couple amino acids in Table 5.

TABLE 5

| Amino acid to be fed | Coupling reagent |
| --- | --- |
| Compound (3a) (1.50 eq) | HOAt (1.50 eq) and DIC (1.50 eq) |
| Fmoc-Dab•HCl (3.00 eq) | HOAt (3.00 eq) and DIC (3.00 eq) |
| DOTA-(COOt-Bu)$_3$ (1.50 eq) | HOAt (1.50 eq) and DIC (1.50 eq) |

5. The resin was washed with DMF for five times, using 20.0 mL of DMF each time (20.0 mL*5), and filtered to obtain the polypeptide resin (5a).

6. Cleavage and purification of the polypeptide:

The resin was washed with MeOH for three times, using 20.0 mL of MeOH each time (20.0 mL*3), and dried under vacuum to obtain the polypeptide resin (5a).

Polypeptide (5a) with side chain protecting groups was added into a flask, and 20 mL of lysis buffer (92.5% TFA/2.5% TIS/2.5% $H_2O$/2.5% MPR) was added. The mixture was stirred at 20° C. for 2 hours for deprotection, precipitated with tert-butyl methyl ether (50.0 mL), and centrifuged (3.00 min, 3000 rpm). The precipitate was washed twice with tert-butyl methyl ether (50.0 ml).

The obtained crude peptide was dried under vacuum for 2 hours to obtain 400 g of crude product.

The crude product was purified by preparative HPLC (TFA conditions: A: 0.075% TFA in $H_2O$ solution, B: ACN) to obtain the target product NYM035 (80.0 mg, 72.2 μmol, yield 14.4%, purity 98.68%) as a white solid.

Example 20: Preparation Process of $^{68}$Ga-NYM035 Molecule

The synthesized NYM035 precursor was subjected to a chelation reaction with radioactive nuclide gallium [$^{68}$Ga] to further obtain a $^{68}$Ga-NYM035 tracer approved for clinical PET/CT tracing. The labeling technology was mature, and a radiochemical purity of the labeled product radioactive compound may usually reach 99%.

The labeling process was shown below. The entire labeling process can be completed within 20 minutes, and yield of the radioactive compound can reach 70%.

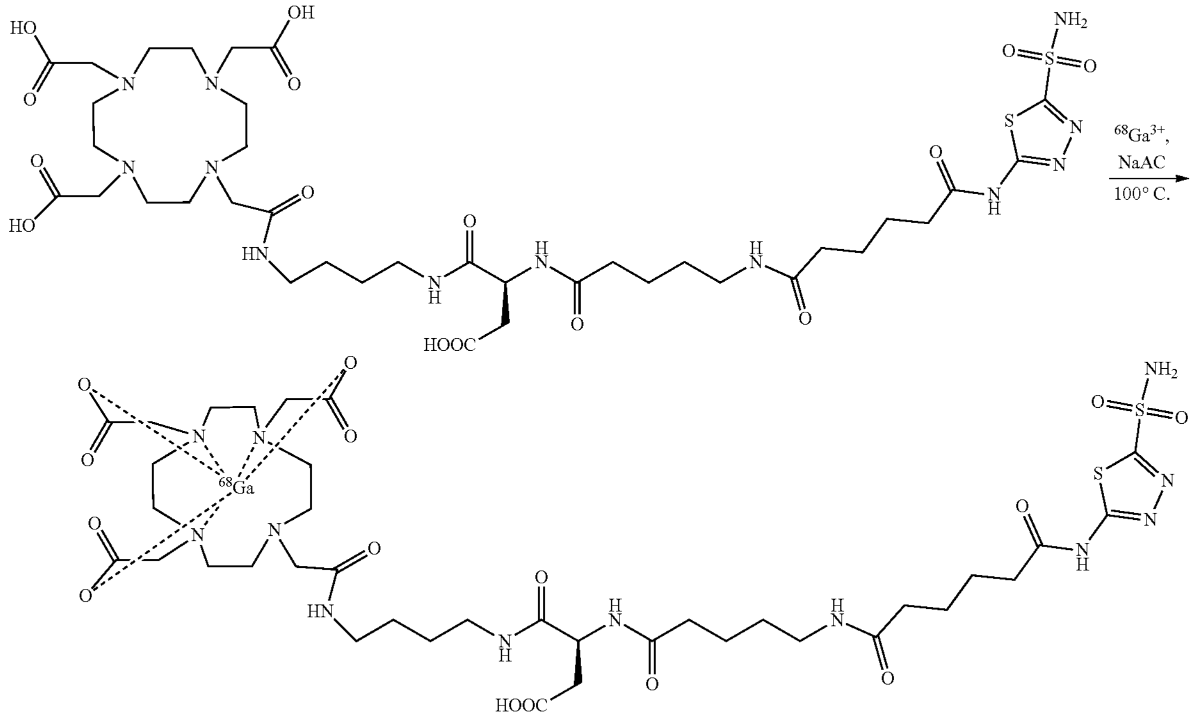

The method for labeling NYM035 with $^{68}Ga$ in Example 20 included the following specific steps. $^{68}Ga$ nuclide was obtained by eluting a germanium gallium generator with a 0.05M hydrochloric acid solution. 1 mL of the $^{68}Ga$ nuclide (20 mCi) solution was added to a reaction bottle, then 1 mL of 0.3 mol/L acetic acid/sodium acetate buffer solution was added to the reaction bottle, allowing a volume ratio of $^{68}Ga$ nuclide to the buffer solution was 1:1, and pH value was adjusted to 4.0. An appropriate amount of NYM035 precursor compound was taken and added to sterilized water for injection to prepare a 1 mg/mL precursor solution. Then, 45 nmol (44 μg) of the precursor solution was taken and added to the reaction bottle, and the mixture reacted for 6 minutes at 105° C. After the reaction was completed, the reaction mixture was cooled for 1 minute. 5 mL of sterilized water for injection was taken using a 10 mL sterile syringe and added to the reaction bottle to dilute the reaction solution while lowering the temperature of the reaction solution. Then, all the liquid in the reaction bottle was sucked into the syringe. Pre-activated Sep-Pak C-18 column was taken out and connected to an outlet of the syringe. The reaction dilution was pushed to flow through the Sep-Pak C-18 column, and the target product $^{68}Ga$-NYM035 was adsorbed by the C-18 column. Then, the C-18 column was eluted with 1 mL of 70% medical grade anhydrous ethanol solution, and the eluted solution was filtered through a 0.22 μm sterile filter membrane and flowed into a sterile vacuum bottle. Then, 4 mL of physiological saline solution was added to obtain a $^{68}Ga$-NYM035 sterile injection solution.

Figure 20:
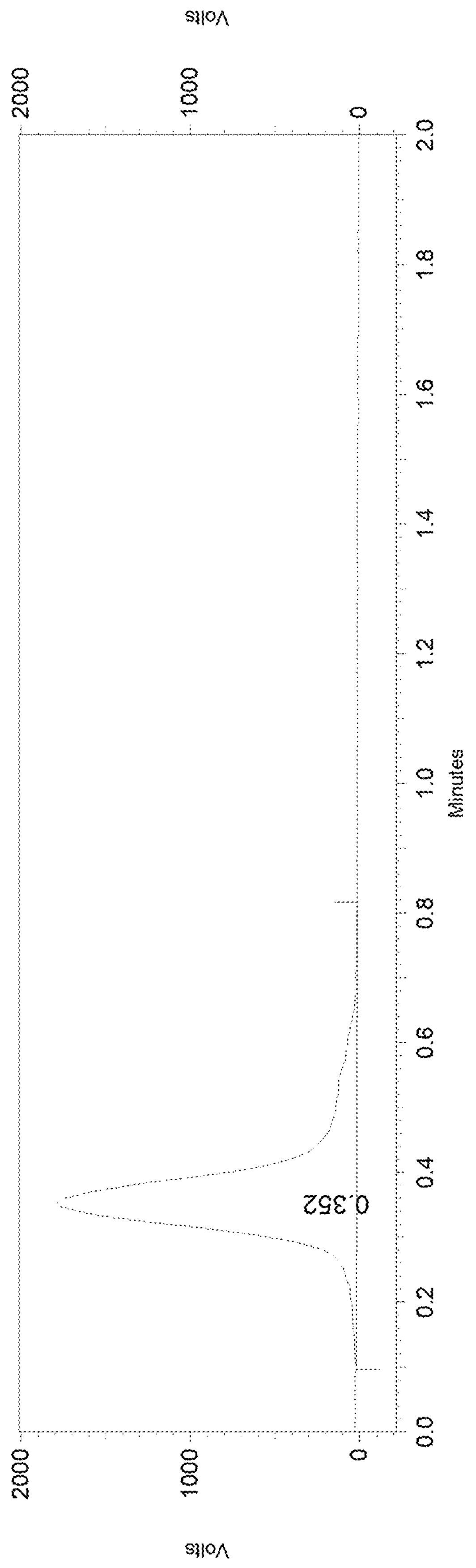
FIG. 20 is a graph of results of radioactive thin layer chromatography scanning purity analysis of $^{68}$Ga-NYM035 according to an embodiment of the present disclosure.

Radioactive thin layer chromatography was used for quality control of the above products, using a carrier of glass fiber paper and a developing agent of 0.5 M citric acid/sodium citrate buffer (pH=5). The glass fiber paper was taken and the sample was transferred using a pipette and tapped gently on the glass fiber paper at a position 1.5 cm from the bottom. Then, the glass fiber paper was put into a tube with 500 μL of 0.5 M citric acid/sodium citrate buffer (pH=5) added in advance, expanded to at a position 2.5 cm from the top of the chromatography paper, and the paper was taken out and dried, and detected with a Radio-TLC thin layer scanner. In 0.5 M citric acid/sodium citrate buffer (pH=5) system, Rf value of the product ranges from 0.3 to 0.6. As shown in FIG. 20, according to the results of radioactive thin layer chromatography scanning purity analysis of the $^{68}Ga$-NYM035 molecule, the radioactive compound had a radiochemical purity of 100%.

Figure 21:
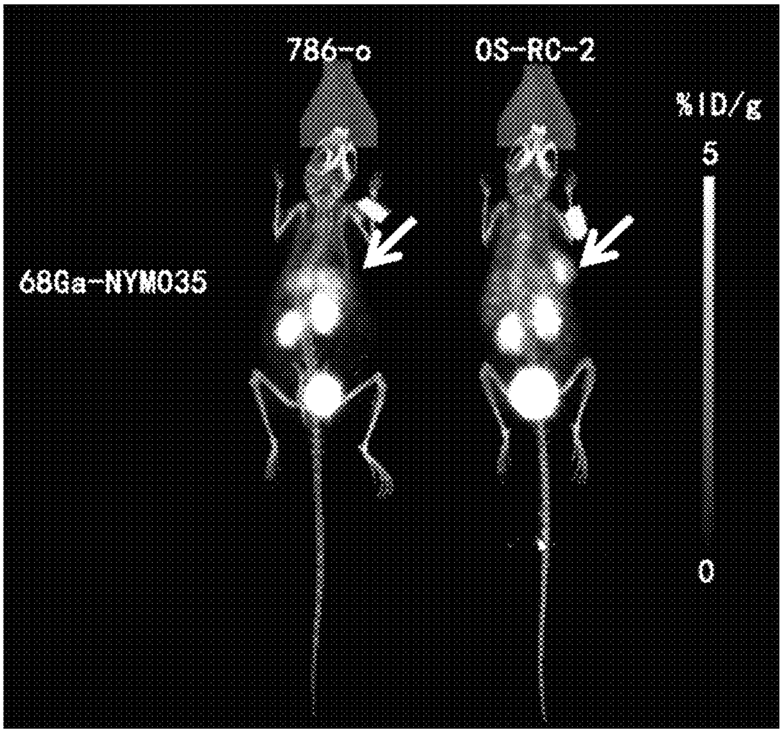
FIG. 21 is an image of PET/CT imaging results of $^{68}$Ga-NYM035 in tumor-bearing 786-O and OS-RC-2 mouse models according to an embodiment of the present disclosure, arrows indicating positions of tumors.

Example 21: PET Scanning Tissue Distribution and Targeting Experiment of $^{68}Ga$-NYM035 in 786-0 and OS-RC-2 Model The experimental 786-O animal model was provided by Hengjia Biotechnology (Suzhou) Co., Ltd. The model was a 786-O tumor subcutaneous heterotopic transplant tumor model established based on BALB/c nude mice. This model was a mouse model constructed for human renal clear cell adenocarcinoma cells. The experimental OS-RC-2 animal model was provided by Hengjia Biotechnology (Suzhou) Co., Ltd. The model was an OS-RC-2 tumor subcutaneous heterotopic transplant tumor model established based on BALB/c nude mice. This model was a mouse model constructed for human renal cancer cells. One animal from each of the two animal models was selected, and each was administrated with 100 μCi of the above-mentioned $^{68}Ga$-NYM035 medicament. After pre-anesthesia with an appropriate concentration of isoflurane/oxygen mixed gas prior to scanning, the animals were placed in a MicroPET/CT imaging cabin (SNPC-303 Super Nova, Pingsheng Medical Technology (Kunshan) Co., Ltd.), and anesthesia was maintained with isoflurane/air mixed gas. A MicroPET/CT scan was performed 1 hour after the administration of the medicament. The scanned images were obtained after reconstruction by means of the device software, and the scanned images were analyzed using PMOD software. As shown in FIG. 21 (in which the arrow indicates the tumor), the $^{68}$Ga-NYM035 medicament was highly enriched in the tumor site of the OS-RC-2 model, while the medicament was less absorbed by the tumor in the 786-0 model, indicating that the medicament had good tumor targeting effect in the OS-RC-2 model.

Example 22: Fluorescence Scanning Experiment and Fluorescence Navigation Anatomy Experiment Human renal clear cell adenocarcinoma cells were selected to construct a mouse model and establish a heterotopic transplant tumor model. The animal model was randomly selected and administrated with a certain amount of molecular medicament compounds (6) to (11) and compounds (15) to (18) with fluorescent groups according to the present disclosure. The animal model was administrated with the corresponding compound and then subjected to in vivo fluorescence scanning imaging in 30 minutes to 120 hours after administration. During the scanning, an appropriate concentration of isoflurane/air mixed gas was used for pre-anesthesia and maintenance of anesthesia. The molecular medicament with fluorescent groups had high fluorescence concentration in the tumor tissue and low fluorescence concentration in other tissues of the tumor model mouse.

The selected mouse model was administered with the drug, and approximately 24 hours later, a routine organ dissection was performed under fluorescence observation. The biodistribution of the drug in the tumor-bearing mice indicated that it was primarily excreted through the kidneys, showing high fluorescence accumulation in the tumor tissue, while the fluorescence accumulation was relatively low in other tissues.

Figure 22:
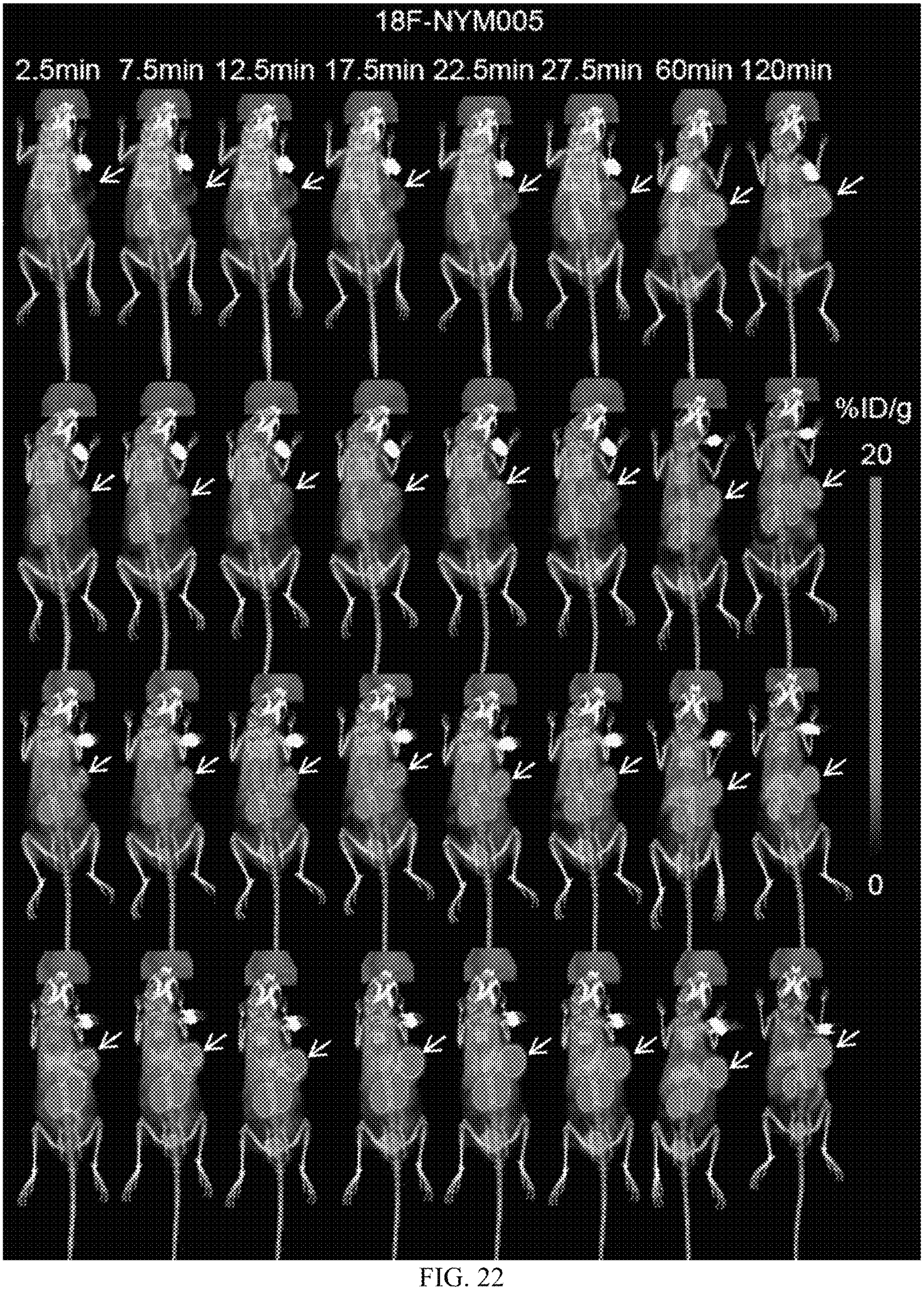
FIG. 22 is an image of PET/CT imaging results of $^{18}$F-NYM005 in a tumor-bearing OS-RC-2 mouse model according to an embodiment of the present disclosure, arrows indicating positions of tumors.
Figure 23:
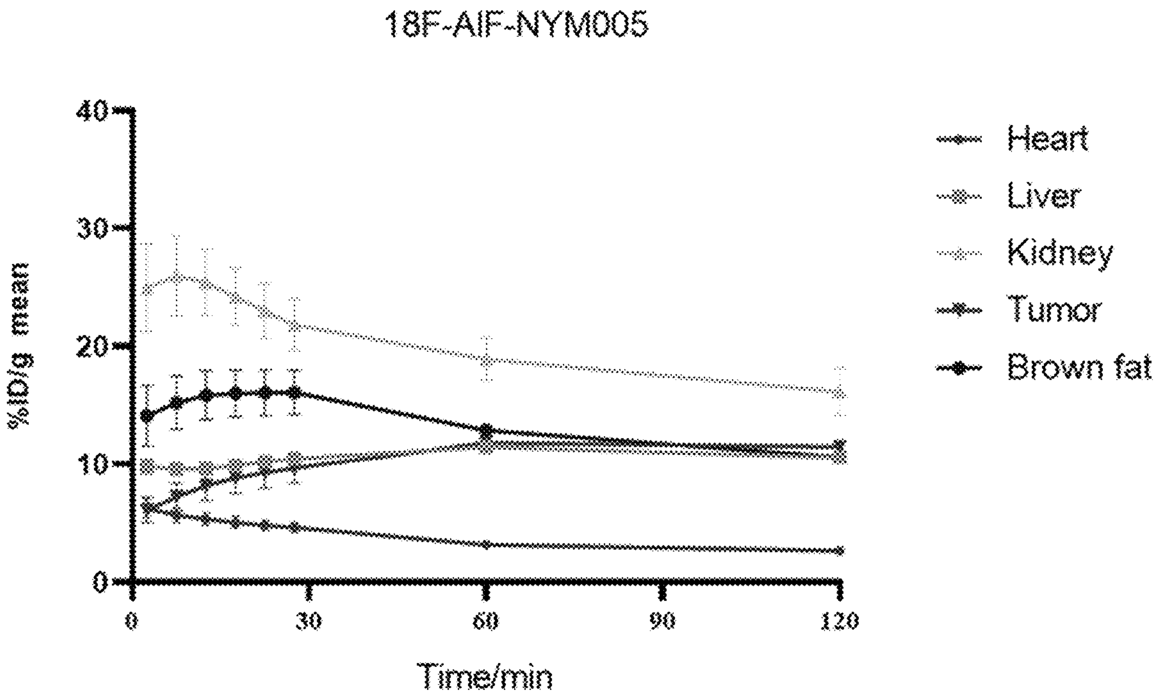
FIG. 23 is a graph of results of $^{18}$F-NYM005 radioactive uptake of tumor in a tumor-bearing OS-RC-2 mouse model according to an embodiment of the present disclosure.

Example 23: PET Scanning Tissue Distribution and Targeting Experiment of $^{18}$F-NYM005 in OS-RC-2 Model The experimental OS-RC-2 animal model was provided by Hengjia Biotechnology (Suzhou) Co., Ltd. The model was an OS-RC-2 tumor subcutaneous heterotopic transplant tumor model established based on BALB/c nude mice. This model was a mouse model constructed for human renal cancer cells. Four animal models were randomly selected, and each was injected with 80 μCi of the above-mentioned $^{18}$F-NYM005 medicament. The animals were placed in a MicroPET/CT imaging cabin (SNPC-303 Super Nova, Pingsheng Medical Technology (Kunshan) Co., Ltd.). A MicroPET/CT scan dynamics was performed 30 minutes after the administration of the drug, and a MicroPET/CT scan was performed 1 h and 2 h after the administration to obtain scanning images. As shown in FIG. 22 and FIG. 23, 1 hour after the administration, the $^{18}$F-NYM005 medicament was highly enriched at the tumor site, and no obvious change was observed until 2 hours after administration, indicating that the $^{18}$F-NYM005 medicament had good tumor targeting effect.

Figure 24:
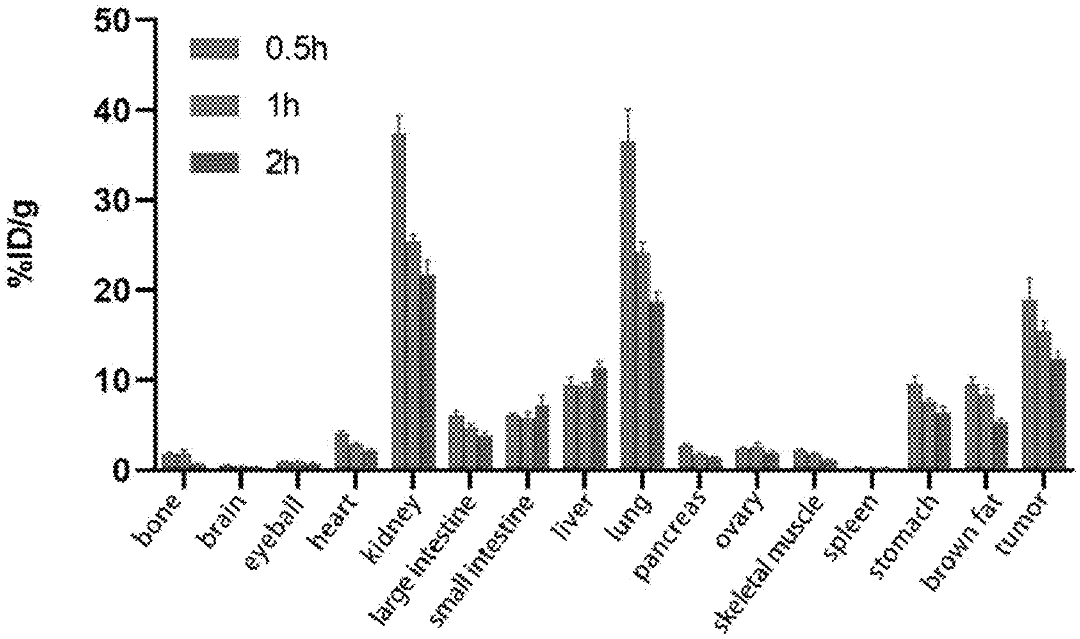
FIG. 24 is a graph of results of tissue distribution of $^{18}$F-NYM005 in an OS-RC-2 mouse model.

Example 24: Tissue Distribution Experiment of $^{18}$F-NYM005 in OS-RC-2 Model The experimental OS-RC-2 animal model was provided by Hengjia Biotechnology (Suzhou) Co., Ltd. The model was an OS-RC-2 tumor subcutaneous heterotopic transplant tumor model established based on BALB/c nude mice. This model was a mouse model constructed for human renal cancer cells. Eighteen animal models were randomly selected, and each animal was injected with 30 μCi of the above-mentioned $^{18}$F-NYM005 drug through tail vein. The animals were dissected at 0.5 h, 1 h, and 2 h after the administration (6 animals were dissected at each of the above-mentioned time points), and 16 organs in total, including bone, brain, eyeball, heart, kidney, large intestine, small intestine, liver, lung, pancreas, ovary, skeletal muscle, spleen, stomach, brown fat, and tumor, were obtained and weighed for y counting. The radioactive uptake values (% ID/g) in the tissues of the animals were calculated using the results of the y counting. As revealed in FIG. 24, in the OS-RC-2 tumor model, uptake of the tumor for $^{18}$F-NYM005 was relatively high and lasted relatively long.

The above-mentioned mouse model was selected and administered with the corresponding compound, and routine organ dissection was performed under fluorescence observation about 24 hours after the administration. The biodistribution of the medicament in tumor model mice indicated that the medicament was mainly excreted through the kidney, and that fluorescence concentration of the medicament was high in tumor tissues and low in other tissues.

In the specification, the description of the reference terms such as "one embodiment", "some embodiments", "example", "specific example", or "some example" means that the specific features, structures, materials, or characteristics described with reference to the embodiment or example are included in at least an embodiment or example of the present disclosure. In this specification, exemplary descriptions of the foregoing terms do not necessarily refer to the same embodiment or example. Moreover, the specific features, structures, materials, or characteristics described may be combined in any one or more embodiments or examples in a suitable manner. Furthermore, those skilled in the art may combine different embodiments or examples and features of different embodiments or examples described in this specification, unless they are contradictory to each other. Although embodiments of the present disclosure are illustrated and described above, it can be understood that the above embodiments are illustrative and should not be construed as limitations of the present disclosure. Those skilled in the art can make changes, modifications, substitutions, and variations to the above embodiments within the scope of the present disclosure.

What is claimed is:

1. A compound, or a pharmaceutically acceptable salt, ester, or solvate thereof, the compound having a structure selected from any one of the following:

(1)

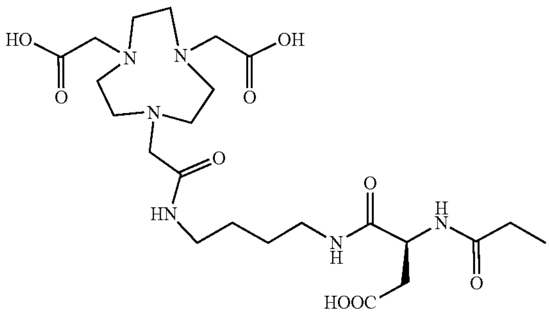

-continued
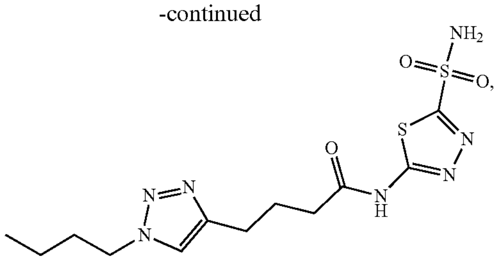
(2)
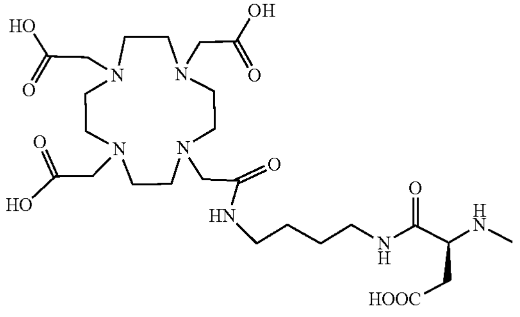
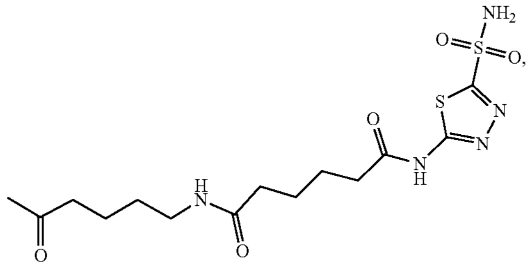
-continued
(3)
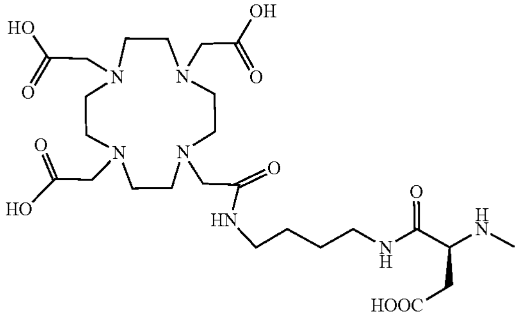
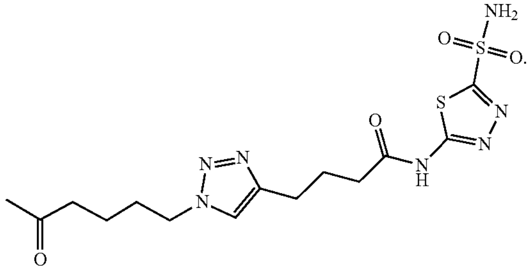
2. A compound, formed by binding the compound, or the pharmaceutically acceptable salt, ester, or solvate thereof according to claim 1 to a radioactive nuclide or a non-radioactive element, wherein the compound has a structure selected from one of the following:
(13)
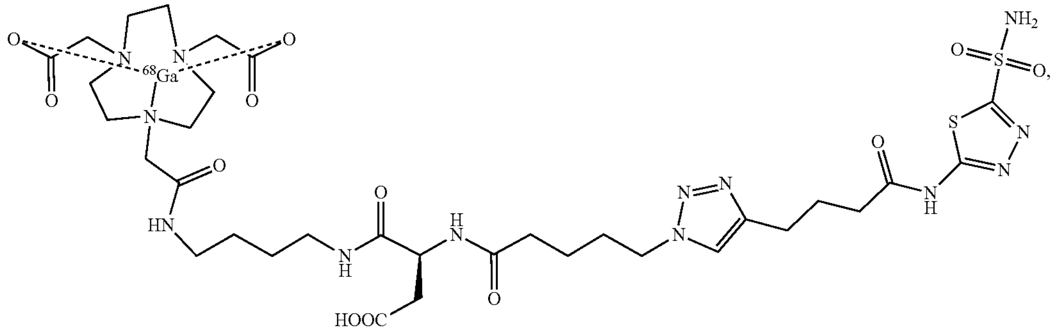
(14)
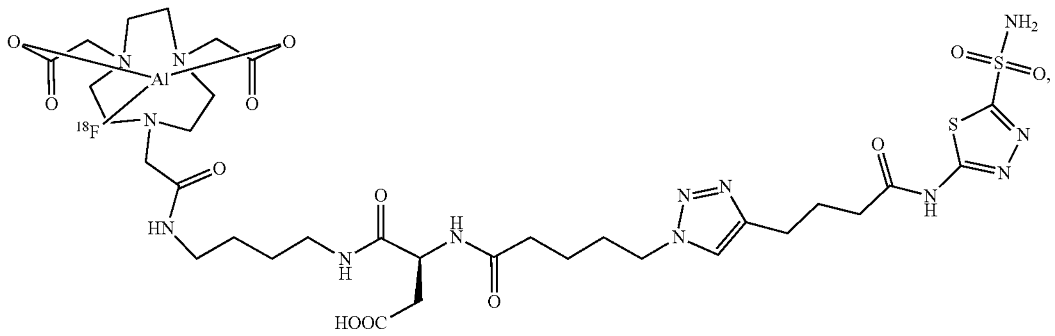

-continued (24)

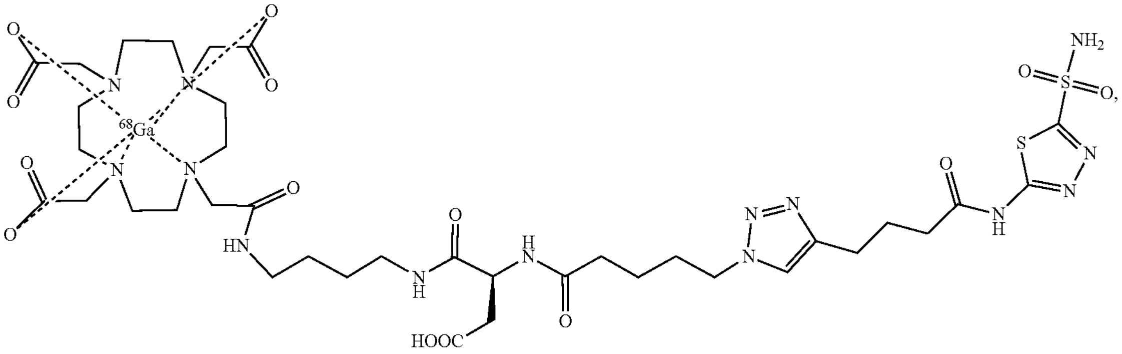

, and (27)

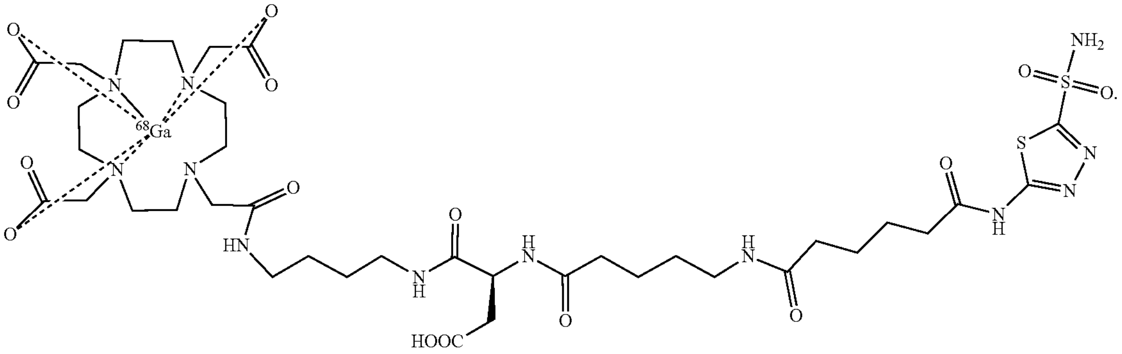

.

3. A pharmaceutical composition, comprising:

the compound, or the pharmaceutically acceptable salt, ester, or solvate thereof according to claim 1; and a pharmaceutically acceptable carrier and excipient.

4. A method for diagnosing and/or treating an associated disease expressing carbonic anhydrase IX, the method comprising:

administering a pharmaceutically acceptable dose of the compound, or the pharmaceutically acceptable salt, ester, or solvate thereof according to claim 2 to a patient.

5. The method according to claim 4, wherein the associated disease expressing carbonic anhydrase IX is kidney cancer, brain glioma, and other solid tumors, and/or metastatic lesions thereof.

6. The method according to claim 4, wherein said diagnosing is performed in a form of PET imaging.

7. A kit, comprising the compound, or the pharmaceutically acceptable salt, ester, or solvate thereof according to claim 1.

* * * * *